United States Patent
Mahon

(10) Patent No.: US 10,918,502 B2
(45) Date of Patent: Feb. 16, 2021

(54) ADJUSTABLE PROSTHETIC INTERFACES AND RELATED SYSTEMS AND METHODS

(71) Applicant: Click Holdings, LLC, Steamboat Springs, CO (US)

(72) Inventor: Joseph A. Mahon, Salt Lake City, UT (US)

(73) Assignee: Click Holdings, LLC, Steamboat Springs, CO (US)

( * ) Notice: Subject to any disclaimer, the term of this patent is extended or adjusted under 35 U.S.C. 154(b) by 0 days.

(21) Appl. No.: 15/938,907

(22) Filed: Mar. 28, 2018

(65) Prior Publication Data

US 2019/0000650 A1 Jan. 3, 2019

Related U.S. Application Data

(60) Continuation of application No. 13/898,248, filed on May 20, 2013, now Pat. No. 9,956,094, which is a division of application No. 12/886,348, filed on Sep. 20, 2010, now Pat. No. 8,443,501.

(60) Provisional application No. 61/243,868, filed on Sep. 18, 2009.

(51) Int. Cl.
*A61F 2/80* (2006.01)
*A61F 2/76* (2006.01)
*A61F 2/50* (2006.01)

(52) U.S. Cl.
CPC .............. *A61F 2/76* (2013.01); *A61F 2/5046* (2013.01); *A61F 2/80* (2013.01); *A61F 2002/503* (2013.01); *A61F 2002/5026* (2013.01); *A61F 2002/5027* (2013.01); *A61F 2002/5035* (2013.01); *Y10T 29/49826* (2015.01); *Y10T 29/49861* (2015.01); *Y10T 29/53* (2015.01); *Y10T 29/53796* (2015.01); *Y10T 29/53913* (2015.01)

(58) Field of Classification Search
CPC combination set(s) only.
See application file for complete search history.

(56) References Cited

U.S. PATENT DOCUMENTS

| 2,500,622 | A | | 3/1950 | Aho |
| 3,545,009 | A | * | 12/1970 | Colley ................. A61F 2/80 |
| | | | | 623/33 |
| 4,161,042 | A | | 7/1979 | Cottingham et al. |
| 4,268,922 | A | | 5/1981 | Marsh et al. |

(Continued)

FOREIGN PATENT DOCUMENTS

| DE | 323671 | 7/1920 |
| DE | 3229812 | 8/1981 |

(Continued)

OTHER PUBLICATIONS

International Search Report and Written Opinion dated Nov. 2, 2010 in international application PCT/US2010/049516.

(Continued)

*Primary Examiner* — Jun S Yoo
(74) *Attorney, Agent, or Firm* — Stoel Rives LLP; Jordan B. Olsen

(57) ABSTRACT

Prosthesis devices can include sockets having adjustable features. In one example, a socket includes one or more panels that can move outwardly or inwardly relative to a receptacle portion of the socket. The panels can be moved by tightening a tensioning line.

16 Claims, 46 Drawing Sheets

(56) References Cited

U.S. PATENT DOCUMENTS

| | | | |
|---|---|---|---|
| 4,653,204 A | 3/1987 | Morell et al. | |
| 4,842,608 A | 6/1989 | Marx et al. | |
| 4,872,879 A | 10/1989 | Shamp | |
| 4,921,502 A | 5/1990 | Shamp | |
| 5,108,455 A | 4/1992 | Telikicheria | |
| 5,529,575 A | 6/1996 | Klotz | |
| 5,571,209 A | 11/1996 | Brown, Sr. | |
| 5,653,766 A | 8/1997 | Naser | |
| 5,800,572 A | 9/1998 | Loveall | |
| 6,202,953 B1 | 3/2001 | Hammerslag | |
| 6,267,390 B1 * | 7/2001 | Maravetz | A43B 5/0401 280/14.21 |
| 6,289,558 B1 | 9/2001 | Hammerslag | |
| 6,329,493 B1 | 12/2001 | El-Hibri | |
| 6,368,357 B1 | 4/2002 | Schon et al. | |
| 6,991,657 B1 | 1/2006 | Price, Jr. | |
| 7,105,122 B2 | 9/2006 | Karason | |
| 7,293,373 B2 | 11/2007 | Reagan et al. | |
| 7,431,738 B2 | 10/2008 | Perkins et al. | |
| 7,488,349 B2 | 2/2009 | Einarsson | |
| 7,947,085 B2 | 5/2011 | Haines et al. | |
| 2002/0095750 A1 | 7/2002 | Hammerslag | |
| 2006/0009860 A1 | 1/2006 | Price, Jr. | |
| 2006/0179935 A1 | 8/2006 | Warila | |
| 2007/0078523 A1 | 4/2007 | Kholwadwala et al. | |
| 2007/0168045 A1 | 7/2007 | Slemker | |
| 2007/0169378 A1 | 7/2007 | Soderberg et al. | |
| 2007/0225824 A1 | 9/2007 | Einarsson | |
| 2007/0278911 A1 | 12/2007 | Vallance et al. | |
| 2008/0066272 A1 | 3/2008 | Hammerslag et al. | |
| 2009/0082877 A1 * | 3/2009 | Einarsson | A61F 2/78 623/33 |
| 2009/0184189 A1 | 7/2009 | Soderberg et al. | |
| 2009/0287128 A1 * | 11/2009 | Ingimundarson | A61H 3/00 602/27 |
| 2010/0139057 A1 | 6/2010 | Soderberg et al. | |
| 2010/0191348 A1 * | 7/2010 | Kettwig | A61F 2/78 623/33 |
| 2010/0274364 A1 * | 10/2010 | Pacanowsky | A61F 2/60 623/36 |
| 2011/0071647 A1 | 3/2011 | Mahon | |
| 2011/0320010 A1 | 3/2011 | Vo | |
| 2012/0101597 A1 * | 4/2012 | Bache | A61F 2/80 623/33 |
| 2012/0271433 A1 * | 10/2012 | Galea | A61F 2/7812 623/37 |
| 2014/0243996 A1 * | 8/2014 | Forster | A61F 2/7812 623/33 |

FOREIGN PATENT DOCUMENTS

| | | |
|---|---|---|
| EP | 1656911 | 5/2006 |
| GB | 2435216 | 8/2007 |
| WO | 2009029191 | 3/2009 |

OTHER PUBLICATIONS

Alley, et al.,Biomechanical Discussion of Current and Emergent Upper-Limb Prosthetic Interface Designs, American Academy of Orthotists and Prosthetists, vol. 5, pp. 1-8 (Jun. 2009).

Boa Technology, et al.,The Boa Lacing System—Dialed in Performance, http://www.boatechnology.com/technology/Overview, Aug. 3, 2009.

Mahon,Joseph A. et al., Non-Final Office Action dated Jul. 11, 2017 for U.S. Appl. No. 13/898,248.

Mahon,Joseph A. et al., Non-Final Office Action dated Sep. 20, 2012 for U.S. Appl. No. 12/886,348.

Mahon,Joseph A. et al., Non-Final Office Action dated Sep. 27, 2016 for U.S. Appl. No. 13/898,248.

Mahon, et al., Notice of Allowance dated Dec. 29, 2017 for U.S. Appl. No. 13/898,248.

Mahon,Joseph A. et al., Notice of Allowance dated Jan. 23, 2013 for U.S. Appl. No. 12/886,348.

Mahon, et al., Notice of Allowance dated Nov. 2, 2017 for U.S. Appl. No. 13/898,248.

Tingleff, et al.,A Newly Developed Socket Design for a Knee Disarticulation Amputee Who is an Active Athlete, Prosthetics and Orthotics International, vol. 26, pp. 72-75 (2002).

* cited by examiner

ADJUSTABLE PROSTHETIC INTERFACES AND RELATED SYSTEMS AND METHODS

CROSS-REFERENCE TO RELATED APPLICATIONS

This application is continuation of U.S. patent application Ser. No. 13/898,248, titled ADJUSTABLE PROSTHETIC INTERFACES AND RELATED SYSTEMS AND METHODS, filed on May 20, 2013, which is a divisional of U.S. patent application Ser. No. 12/886,348, titled ADJUSTABLE PROSTHETIC INTERFACES AND RELATED SYSTEMS AND METHODS, filed on Sep. 20, 2010, which claims the benefit under 35 U.S.C. § 119(e) of U.S. Provisional Patent Application No. 61/243,898, titled ADJUSTABLE PROSTHETIC INTERFACE AND METHODS, filed on Sep. 18, 2009, the entire contents of each of which are hereby incorporated by reference herein.

TECHNICAL FIELD

The present disclosure relates to prosthetic devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
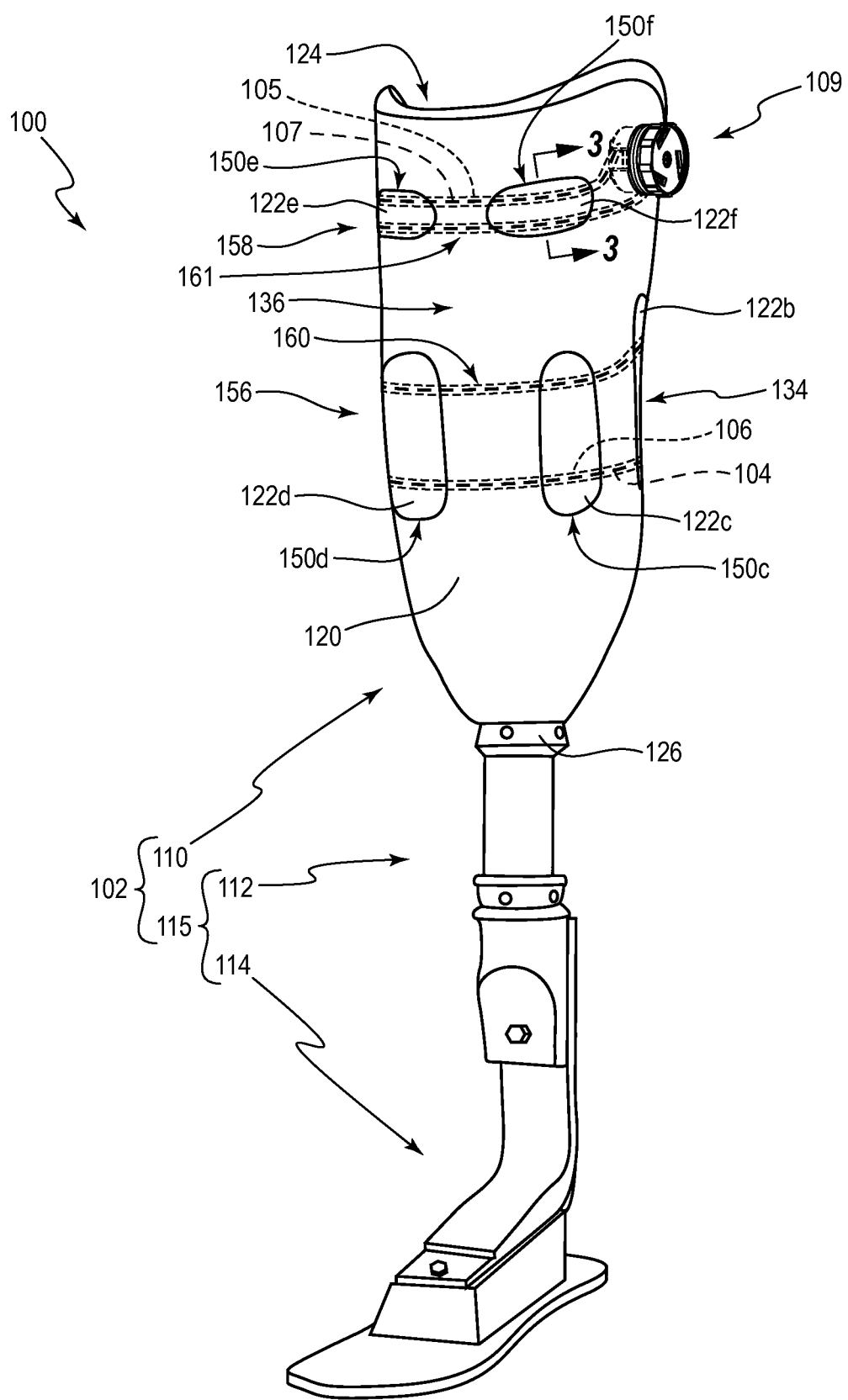
FIG. 1 is a front perspective view of an embodiment of an adjustable prosthetic system that includes a socket and adjustable panels.
Figure 2:
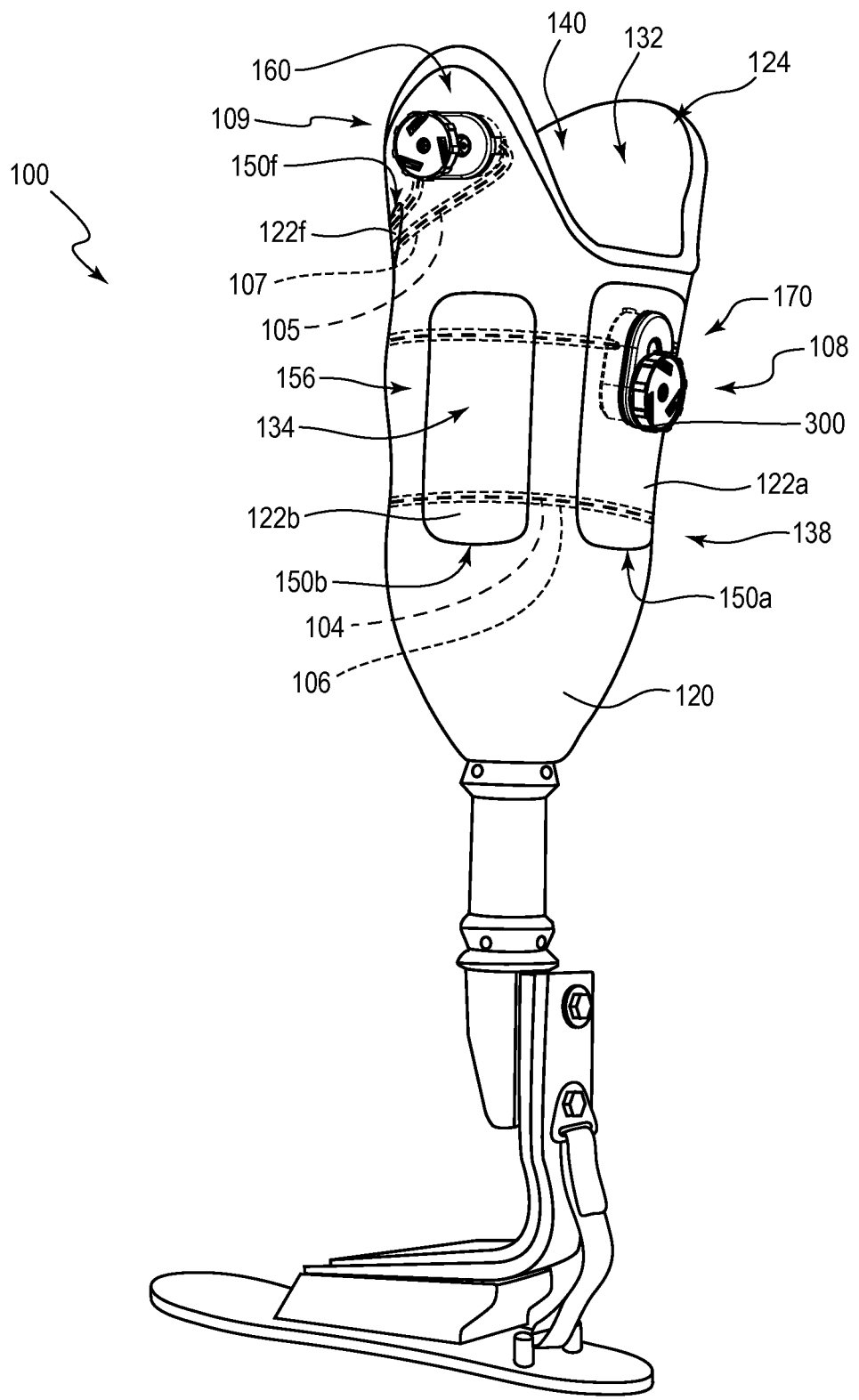
FIG. 2 is a rear perspective view of the adjustable prosthetic system of FIG. 1.

Various embodiments of prosthetic devices that are configured to be adjustable relative to a residual limb (or "residuum") of an amputee are described herein. An example of one such embodiment is depicted in FIGS. 1 and 2, which is discussed in detail below. Related systems and methods are also disclosed. In certain embodiments, a prosthetic device includes a socket that has adjustable portions. The adjustable portions can be configured to move relative to a substantially rigid portion of the socket that substantially maintains its shape during movement of the adjustable portions. Accordingly, in some embodiments, the socket substantially maintains its general shape, while only portions thereof are moved so as to contact specific regions of the residuum. Such systems can enhance the comfort of a wearer of the prosthetic device, and can otherwise improve the operation of the device, as compared with standard prosthetic devices. Other features and advantages of the various embodiments described herein will be evident from the disclosure that follows.

For the sake of convenience, much of the following disclosure is directed to prosthetic devices that are configured for use with residual portions of an amputated leg, such as a leg that has undergone a transfemoral (i.e., above-knee) or transtibial (i.e., below-knee) amputation. It should be appreciated that the disclosure is also applicable to other prosthetic devices, such as those configured for use with the residuum of an amputated arm (e.g., after an above-elbow or below-elbow amputation).

The use of transtibial prostheses by transtibial amputees is generally well known. Transtibial prostheses can include a socket, a shank, and a foot-ankle system. A variety of sockets, shanks, and foot-ankle systems are available, which can be combined in any suitable manner to produce a transtibial prosthesis that is tailored to meet the individual needs of different transtibial amputees. The socket generally acts as an interface between the amputee and the prosthesis. The socket can be instrumental in transferring the weight of a transtibial amputee to the ground by the way of the prosthesis. The shank can transfer vertical loads (e.g., at least a portion of the weight of the amputee) to the foot-ankle system, which interfaces with the ground.

The general use of a socket to fit a transtibial prosthesis to a residuum is well known. Some sockets have total contact with the residuum, and may contact the residuum substantially about a full periphery thereof. Other or further sockets can define four walls, and each wall of a socket can have a specific function relative to the residuum. The four walls can include an anterior wall, a posterior wall, a medial wall, and a lateral wall.

Whether the prosthesis is a transtibial or transfemoral prosthesis, or even an upper limb prosthesis (such as for upper or lower arm amputees), the interface between the prosthesis and the person's residuum is of great importance. The socket portion of the prosthesis typically defines the primary interface between the prosthesis and the residuum. Several factors can be weighed in the design of a socket, including whether the socket satisfactory transmits the desired load, provides satisfactory stability, provides efficient control for mobility, is easily fitted, and/or is comfortable.

The residuum typically changes size not only over months or years as the amputee's body ages or recovers from the initial amputation, but also on daily basis, and even throughout a given day. The daily or short-term fluctuations in residuum size often are a result of water retention or loss. The more active an amputee is throughout the day, the greater the water loss in the residuum may be. This change in size can have an effect on the fit between the residuum and the prosthesis socket. Amputees often account for such a reduction in limb size by adding a sock to the limb. Adding the sock often requires a person to remove an article of clothing, remove and then replace the prosthesis, and then put back on the removed article of clothing. This process not only can be time consuming, but it can also require a certain amount of privacy. In many instances, a number of socks (e.g., 3, 5, 10, or more) may be added to the residuum throughout the day in order to maintain adequate fit between the residuum and socket for the amputee to avoid the pain and discomfort that can result from an improper fit.

The addition of socks to the residuum can negatively affect a fit between the prosthesis and the residuum. As socks are added to the residuum, a gap between the residuum and the socket in the lateral direction may be filled, as desired, but the entire limb may also concurrently change position relative to the socket in an axial direction. This axial shift can displace the limb from specifically contoured features of the socket that typically serve as the interface between the socket and the residuum such that the complementary portions of the residuum no longer correspond with their socket counterparts. Furthermore, an entirety of a residuum may not decrease in size as a result of water retention or loss. Rather, size reduction may generally be isolated to areas of soft tissue and muscle. Accordingly, adding layers of socks over areas of bony anatomy that has not lost any volume can increase pressure on those bony areas, thus creating pressure sores. Also, additional of one or more socks to a residuum can become uncomfortably hot for the wearer due to the insulating properties of the socks, and may lead to perspiration that can result in a painful or ineffective fit. One or more of the drawbacks or limitations of known prosthetic devices and systems and/or methods for their use, such as those just described, may advantageously be reduced or eliminated by embodiments disclosed herein.

Figure 3:
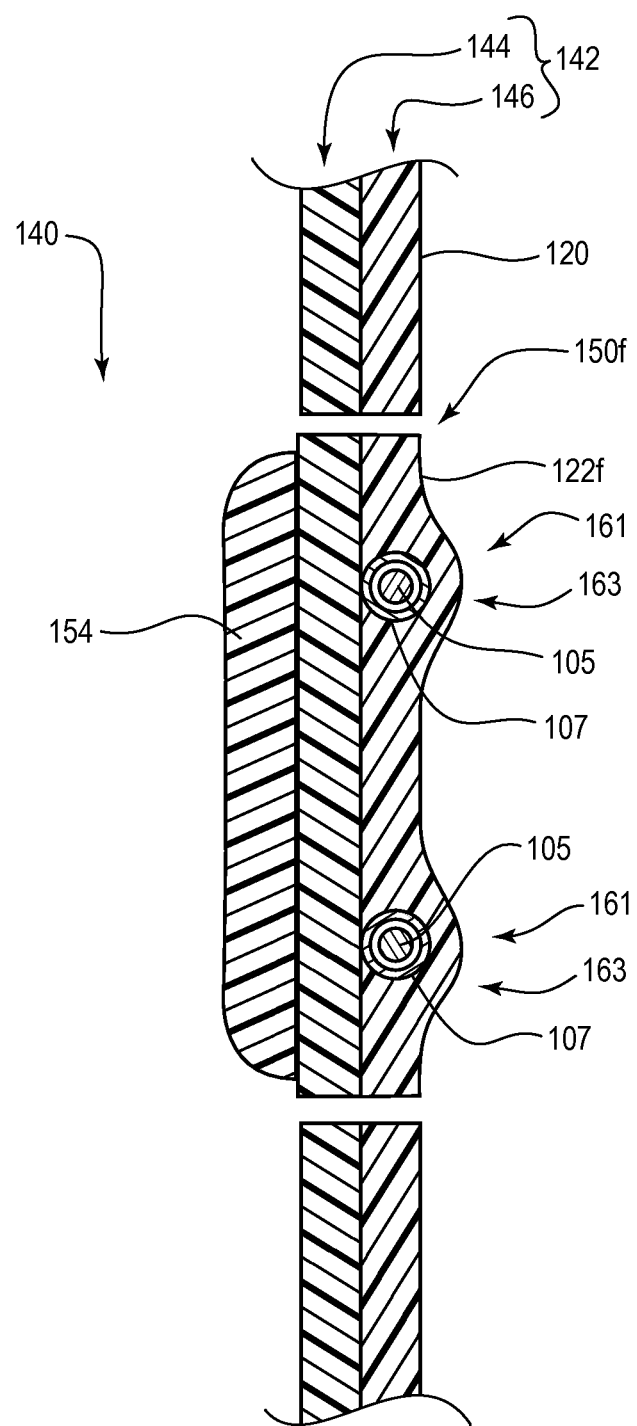
FIG. 3 is a cross-sectional view of a portion of the adjustable prosthetic system of FIG. 1 taken along the view line 3-3 in FIG. 1.

FIGS. 1-3 illustrate an embodiment of an adjustable prosthetic system 100. As shown in FIGS. 1 and 2, the system 100 includes a prosthetic device 102, distal and proximal tensioning lines 104, 105, distal and proximal guide members 106, 107, and distal and proximal tightening mechanisms 108, 109. In the illustrated embodiment, the prosthetic device 102 is configured as a substitute for a portion of a right leg of an amputee. The prosthetic device 102 includes a socket 110, a support or pylon 112, and an ankle-foot structure 114. As described further below, the socket 110 can be configured to receive a residuum of a leg therein. The pylon and/or the ankle-foot structure may be termed more generally as a prosthetic extremity 115, such that the socket 110 can be said to serve as an interface between the residuum and the prosthetic extremity 115. Any suitable arrangement of the prosthetic extremity 115 is possible.

The socket 110 includes a receptacle region 120, also referred there herein simply as a receptacle, and further includes a plurality of panels 122a-122f that are configured to move relative to the receptacle 120. The socket 110 can be configured to provide a high amount of surface contact with the limb to achieve a close fit therewith, which can correlate with the high amount of comfort for the user. In the illustrated embodiment, the receptacle 120 is shaped substantially as an elongated cup that is sized to receive the residuum of a transtibial amputation therein. The receptacle 120 defines an opening 124 at an upper end thereof and narrows toward a lower end thereof. The receptacle 120 can include a support attachment 126 to which the pylon 112 is mounted.

The receptacle 120 can include four general sides, portions, or regions 132, 134, 136, 138. As the receptacle 120 is configured for use with a right leg of an amputee, the right side may be referred to as a lateral region 132, the left side may be referred to as a medial region 134, a forward side may be referred to as an anterior region 136, and a rearward side may be referred to as a posterior region 138.

The receptacle 120 can define a cavity 140 into which the residuum can be received. The receptacle 120 can be substantially rigid so as to maintain its shape or form when forces are applied thereto, whether from the residuum when it is positioned therein or from compressive forces at an exterior thereof. The term "substantially rigid" is sufficiently broad to cover arrangements where the receptacle 120 is sufficiently rigid, solid, or firm so as to undergo no change in shape or configuration due to stresses applied thereto by the residuum under normal use (i.e., solid), as well as arrangements where the receptacle 120 is very rigid, solid, or firm, but is resilient and may undergo slight, non-permanent deformations due to the standard stresses of use (i.e., flexibly firm).

The receptacle 120 can have a wall structure 142 that includes one or more materials, and may include one or more laminated layers 144, 146 (see FIG. 3). In various embodiments, one or more layers 144, 146 of the wall structure 142 of the receptacle 120 can include one or more hardened plastic resins (e.g., acrylic, epoxy, polyester). In other or further embodiments, one or more layers 144, 146 can comprise one or more reinforcement textiles (e.g., fiberglass, nylon, carbon, Dacron®, Kevlar®). Any other suitable materials may be used.

In the illustrated embodiment, the receptacle 120 defines a series of ports 150a-150f that correspond with the panels 122a-122f. In particular, the ports 150a-150f are sized and shaped so as to permit the panels 122a-122f to move freely therethrough. For one or more of the ports 150a-150f (e.g., the port 150a), edges of the port 150a may substantially define a plane, and the associated panel 122a may be configured to move relative to the port 150a in a direction that is normal to the plane. More generally, the panels 122a-122f can be configured to move outwardly or inwardly relative to the cavity 140. The panels 122a-122f may also be termed to move in a radial direction, but this does not necessarily imply that the panels 122a-122f move along a line that is directed through an axial center of the receptacle 120, nor does it necessarily imply that a cross-sectional perimeter of the receptacle 120 is circular. The illustrated panels 122a-122f are fully separated from the receptacle 120 and are able to move independently of the receptacle 120. The panels 122a-122f may be termed as free floating.

In other embodiments, such as discussed below, the socket 110 can include panels that are connected to the receptacle 120, such as via a hinge. For example, an edge of a panel may be fixedly connected to the receptacle 120, whereas other edges of the panel can be separate from the receptacle 120 so as to move freely relative thereto. In the illustrated embodiment, the panels 122a-122f can be moved relative to the receptacle 120 substantially without changing a shape or configuration of the receptacle 120.

As shown in FIG. 3, the panel 122 may comprise the same material as that of the receptacle 120. For example, at least a portion of the panel 122 can be cut from the wall structure 142 in a manner such as discussed below. However, in other embodiments, the panels 122 may comprise one or more materials that are different from those of which the receptacle 120 is formed.

In the illustrated embodiment, each panel 122a-122f includes a pad 154 at an interior thereof. The pad 154 can be configured to contact the residuum (e.g., directly contact the residuum) or to apply pressure to the residuum. Accordingly, the panels 122a-122f may also be referred to herein as pressure members. The pad 154 can have a thickness such that a total thickness of the panel 122 is thicker than the portion of the receptacle 120 that surrounds the panel 122. The pad 154 can comprise any suitable material. In some applications, the pad 154 may be deformable and resilient, and the pad may have any suitable flexibility or durometer properties.

Due to a thickness of a panel 122, the panel can be forced outwardly relative to the receptacle 120 when the residuum (when it is in a relatively large state), is positioned within the cavity 140 of the receptacle 120. For example, in the embodiment shown in FIG. 3, the pad 154 extends into the cavity 140 when an outer surface of the panel 122 is flush with an outer surface of the receptacle 120. Accordingly, the pad 154 can be moved outwardly to bring an inner surface of the pad 154 into alignment with an inner surface of the receptacle 120 and so as to permit the residuum to fill the cavity 140. As the residuum decreases in volume over time, the panel 122 can be pulled inwardly so as to apply pressure to the residuum, or so as to maintain a desired pressure on the residuum, and thus achieve or maintain a desired fit therewith.

Any suitable number and arrangement of the panels 122a-122f is possible. For example, in various embodiments, the socket 110 can comprise one or more, two or more, three or more, four or more, five or more, or even ten, fifteen, or twenty or more panels. As discussed further below, the position, size, and/or shape of each panel may be specific to a particular residuum for which the socket 110 has been manufactured. Moreover, one or more of the panels 122a-122f may be configured to contact a portion of the residuum that is more prone to change in size, as compared with other portions of the residuum. In the illustrated embodiment, the panels 122a-122f are sized and shaped to interact with specific portions of the residuum as follows: the panel 122a is configured to apply pressure to the gastrocnemius muscle and the soleus muscle, or more generally, to a posterior muscle compartment; the panel 122b is configured to apply pressure to a posterior medial aspect of the tibia, or more generally, to a medial region of the tibia; the panel 122c is configured to apply pressure to an anterior medial aspect of the tibia; the panel 122d is configured to apply pressure to the interosseous membrane; the panel 122e is configured to apply pressure to a patellar tendon region; and the panel 122f is configured to apply pressure to a medial patellar tendon region. Other arrangements are also possible.

In the illustrated embodiment, the panels 122a-122f are arranged generally in either a lower or distal zone 156

(panels 122a-122d) or an upper or proximal zone 158 (panels 122e, 122f). The panels of the distal zone 156 are all coupled with the distal tensioning line 104, and the panels of the proximal zone 158 are both coupled with the proximal tensioning line 105. Each zone of panels is thus interconnected. Stated otherwise, each set of panels is able to move inwardly in tandem and/or apply an increased amount of pressure on the residuum in tandem.

The tensioning lines 104, 105 can comprise any suitable arrangement, such as, for example, a wire, cable, or the like (e.g., a lace), and may be relatively flexible or pliant in transverse direction but relatively inextensible in a longitudinal direction. The tensioning lines 104, 105 can comprise any suitable material, such as, for example, metal, polyester, or Spectra.

The tensioning lines 104, 105 can be positioned within the guides 106, 107, which can define separate guide paths 160, 161. The guides 106, 107 can be configured to protect the wall structure 142 of the receptacle 120 from wearing due to friction from the tensioning lines 104, 105. The guides 106, 107 can also protect the tensioning lines 104, 105 from undue wear. In some embodiments, a guide 106, 107 comprises a tube of any suitable polymeric material (e.g., nylon) through which the corresponding tensioning line 104, 105 is threaded. As shown in FIG. 3, in some embodiments, the guides 106, 107 can extend through an interior of a panel 122. For example, the guide 107 may run substantially parallel to an outer surface of the panel 122f. In the illustrated embodiment, the guides 106, 107 are laminated between two layers of the panel 122, and due to the lamination process employed, protrusions 163 of the outer surface are present along a length of each guide path 160, 161.

As discussed below, the guide paths 160, 161 can define any suitable contour. In the illustrated embodiment, the distal guide path 160 includes two horizontally directed portions that are joined at each end by a substantially C-shaped reversal (not shown). One of the reversals is located within the panel 122a, whereas the other is located within the lateral region 124 of the receptacle 120. Each end of the guide path 160 terminates at an opposing side of the tightening mechanism 108. Similarly, the proximal guide path 161 includes two horizontally directed portions. At one end, the horizontal portions are joined by a C-shaped reversal, whereas at the other end (shown in FIG. 2), the guide path 161 terminates at the proximal tightening mechanism 109. In the illustrated embodiment, each end of the guide path 160 terminates at an opposing end of the tightening mechanism 109. Other patterns for the guide paths 160, 161 are also possible. For example, whereas in the illustrated embodiments the guide paths 160, 161 never cross over themselves and/or each other, in other embodiments they do.

In the illustrated embodiment, each of the guide paths 160, 161 makes two passes through the panels in their respective zones. Moreover, due to the pattern of or course followed by the guide paths 160, 161, separate portions of each of the tensioning lines 104, 105 move through each of the panels 122a-122d and 122e, 122f, respectively, in opposite directions. The upper and lower passes of the guide paths 160, 161 through the panels allow the tensioning lines 104, 105 to provide a balanced or evenly distributed inward force to the panels 122a-122f, which can reduce torquing of the panels. Other arrangements are also possible. For example, in some embodiments, a tensioning line can pass through a panel only once, such as through its center. In other embodiments, a tensioning line can pass through a panel two or more, three or more, or four or more times.

As shown in FIG. 2, the tensioning lines 104, 105 can be connected to the tightening members 108, 109, each of which can be configured to increase or decrease a tension in the tensioning lines 104, 105, respectively. With reference only to the distal tightening member 108 for the sake of convenience, the tightening member can include an actuator 170. In some embodiments, the actuator 170 can be used to selectively and/or incrementally increase the tension in the tensioning line 104. In other or further embodiments, the actuator 170 can be used to selectively and/or incrementally decrease the tension in the tensioning line 104. In the illustrated example, the tightening member 108 comprises a ratcheting device 300, which is described below. The proximal tightening member 109 can be similar to the distal tightening member 108, but may be smaller in some embodiments.

In the illustrated embodiment, the tightening member 108 is fixedly attached to the panel 122a, and thus is configured to move relative to the receptacle 120. In other embodiments, such as that illustrated in FIGS. 4 and 5, the tightening member 108 can be fixed relative to the receptacle 120. In either case, actuating the tightening member 108 can cause the panels 122a-122d to move radially inward. For example in the illustrated embodiment, actuating the tightening member 108 can draw a portion of the tensioning line 104 into the tightening member 108 so as to constrict a perimeter defined by the tensioning line 104. Such constriction can urge the panels 122a-122d inwardly.

Figure 4:
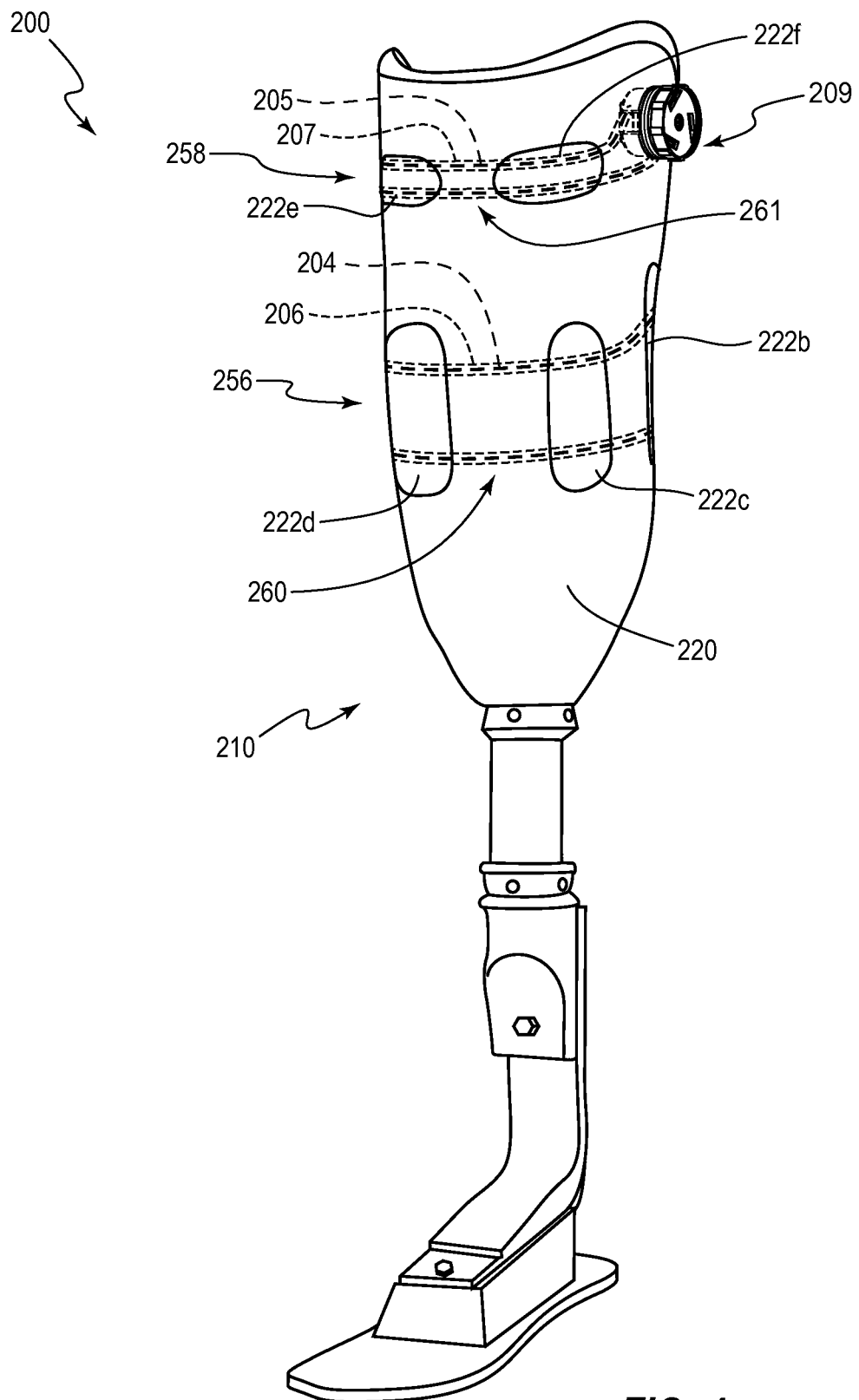
FIG. 4 is a front perspective view of another embodiment of an adjustable prosthetic system that includes a socket and adjustable panels.
Figure 5:
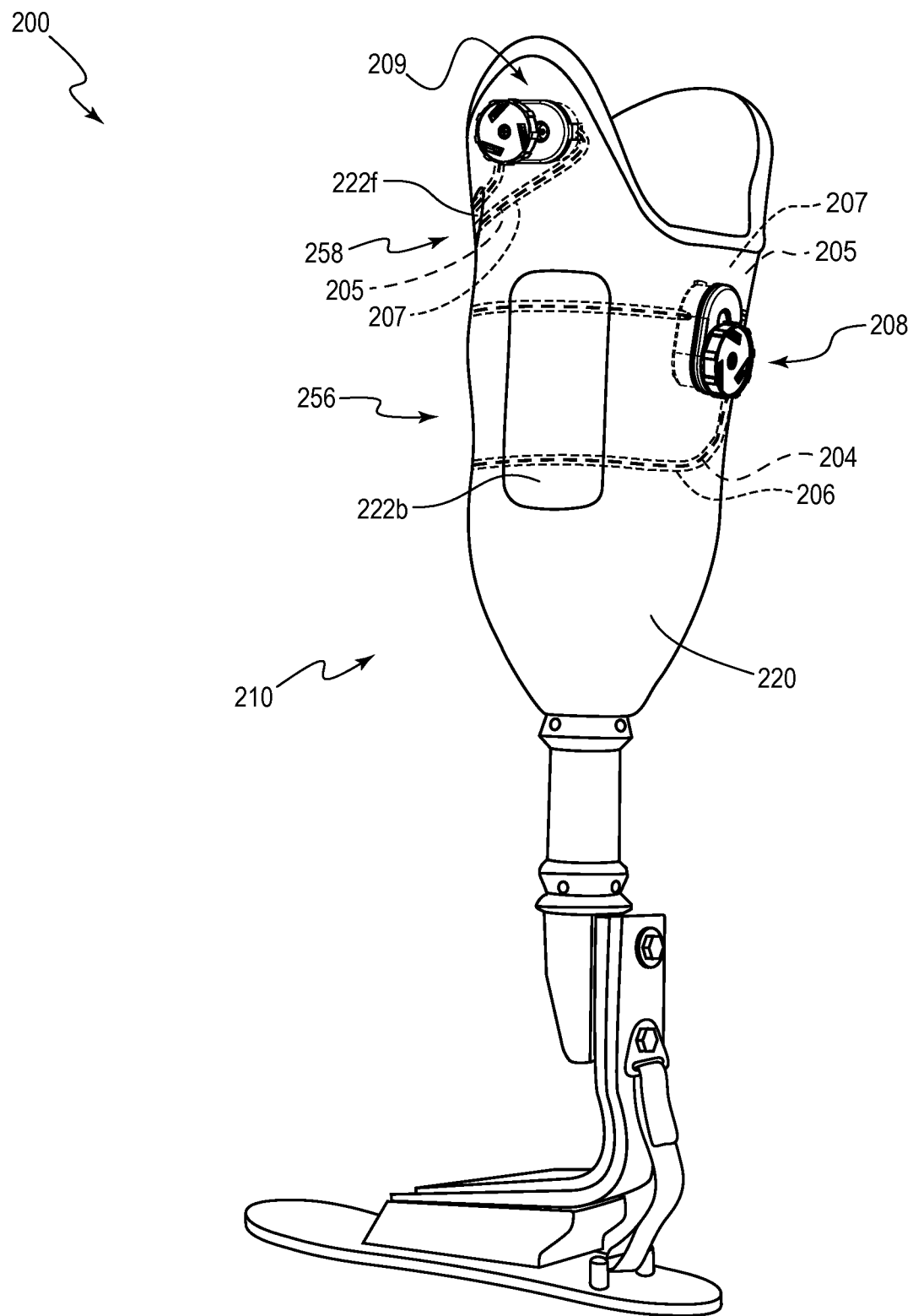
FIG. 5 is a rear perspective view of the adjustable prosthetic system of FIG. 4.

FIGS. 4 and 5 illustrate another embodiment of an adjustable prosthetic system 200, which can resemble the adjustable prosthetic system 200 described above in certain respects. Accordingly, like features are designated with like reference numerals, with the leading digits incremented to "2." Relevant disclosure set forth above regarding similarly identified features thus may not be repeated hereafter. Moreover, specific features of the adjustable prosthetic system 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the adjustable prosthetic system 200. Any suitable combination of the features and variations of the same described with respect to the adjustable prosthetic system 100 can be employed with the adjustable prosthetic system 200, and vice versa. This pattern of disclosure applies equally to further embodiments depicted in subsequent figures and described hereafter.

The adjustable prosthetic system 200 can include a socket 210 that includes a receptacle 220 and a plurality of panels 222b-222f. The panels 222b-222d are positioned within a lower zone 256, and the panels 222e, 222f are positioned within an upper zone 258. The system 200 further comprises a distal tensioning line 204 and a distal guide 206 that pass through the panels 222b-222d, and also comprises an proximal tensioning line 205 and proximal guide 207 that pass through the panels 222e, 222f. The lower tensioning line 204 is connected to a lower tightening member 208, and the upper tensioning line 205 is connected to an upper tightening member 209. Each of the upper and lower tightening members 209, 208 is fixedly secured to the receptacle 220. Each of the tensioning lines 204, 205 follows a guide path 260, 261 that resembles the guide paths 160, 161 described above. However, other arrangements of the guide paths 260, 261 are possible.

Figure 6B:
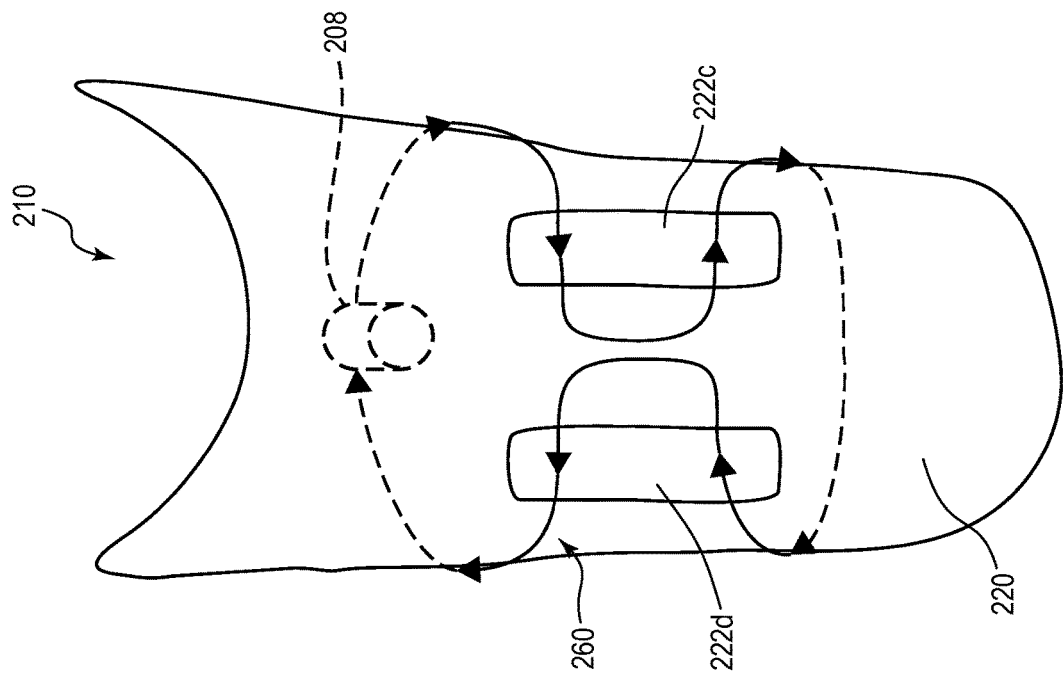
FIG. 6B is a schematic front view of another embodiment of an adjustable prosthetic system showing another routing pattern of a tensioning line.
Figure 6A:
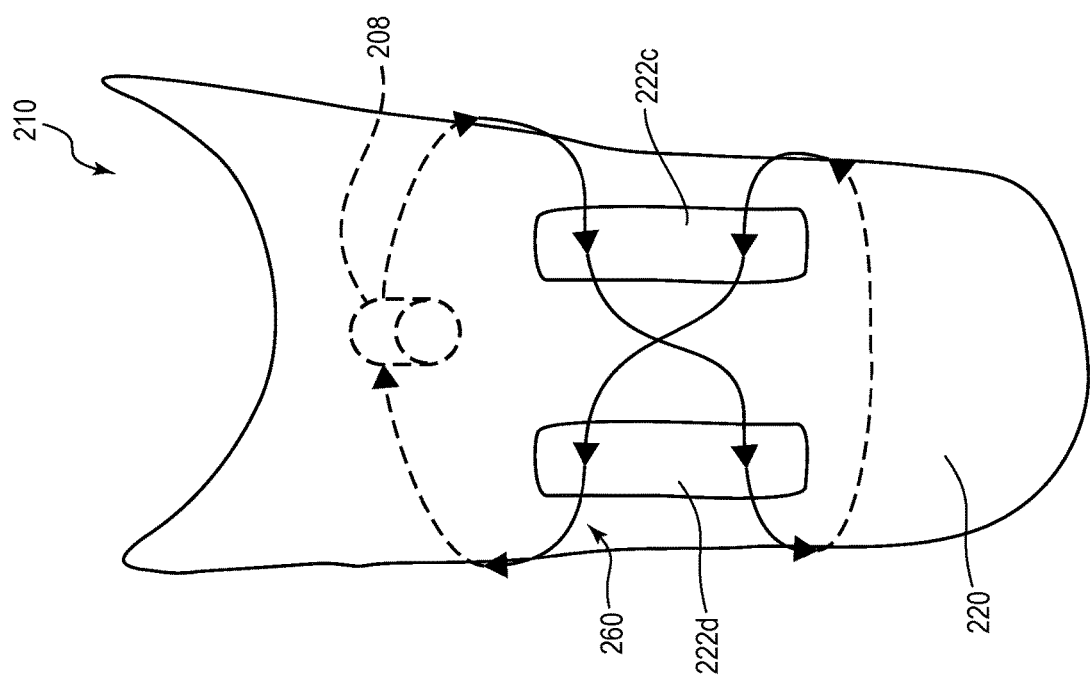
FIG. 6A is a schematic front view of another embodiment of an adjustable prosthetic system showing a routing pattern of a tensioning line.

FIGS. 6A and 6B schematically illustrate two additional patterns that the guide path 260 can take. In FIG. 6A, the guide path 260 proceeds from the tightening mechanism 208 through an upper end of the panel 222c, through a lower end of the panel 222d, circles around the back of the receptacle 220, proceeds through a lower end of the panel 222c, through an upper end of the panel 222d, and then terminates at an opposite side of the tightening mechanism 208. As can be seen, the guide path 260 crosses over itself within the receptacle 220 at a position between the panels 222c, 222d.

In FIG. 6B, the guide path 260 proceeds from the tightening mechanism 208 through an upper end of the panel 222c, defines a C-shaped turn within the receptacle 220 and then proceeds through a lower end of the panel 222c, circles around the back of the receptacle 220, proceeds through a lower end of the panel 222d, defines a C-shaped turn within the receptacle 220 and then proceeds through an upper end of the panel 222d, and then terminates at an opposite side of the tightening mechanism 208. As can be seen, the guide path 260 does not cross over itself at any point.

As previously mentioned, the systems 100, 200 can be used with any suitable tightening mechanism. An illustrative example of an embodiment of a suitable tightening mechanism is provided in FIGS. 7-11. Additional illustrative tightening mechanisms are shown and described further below.

Figure 7:
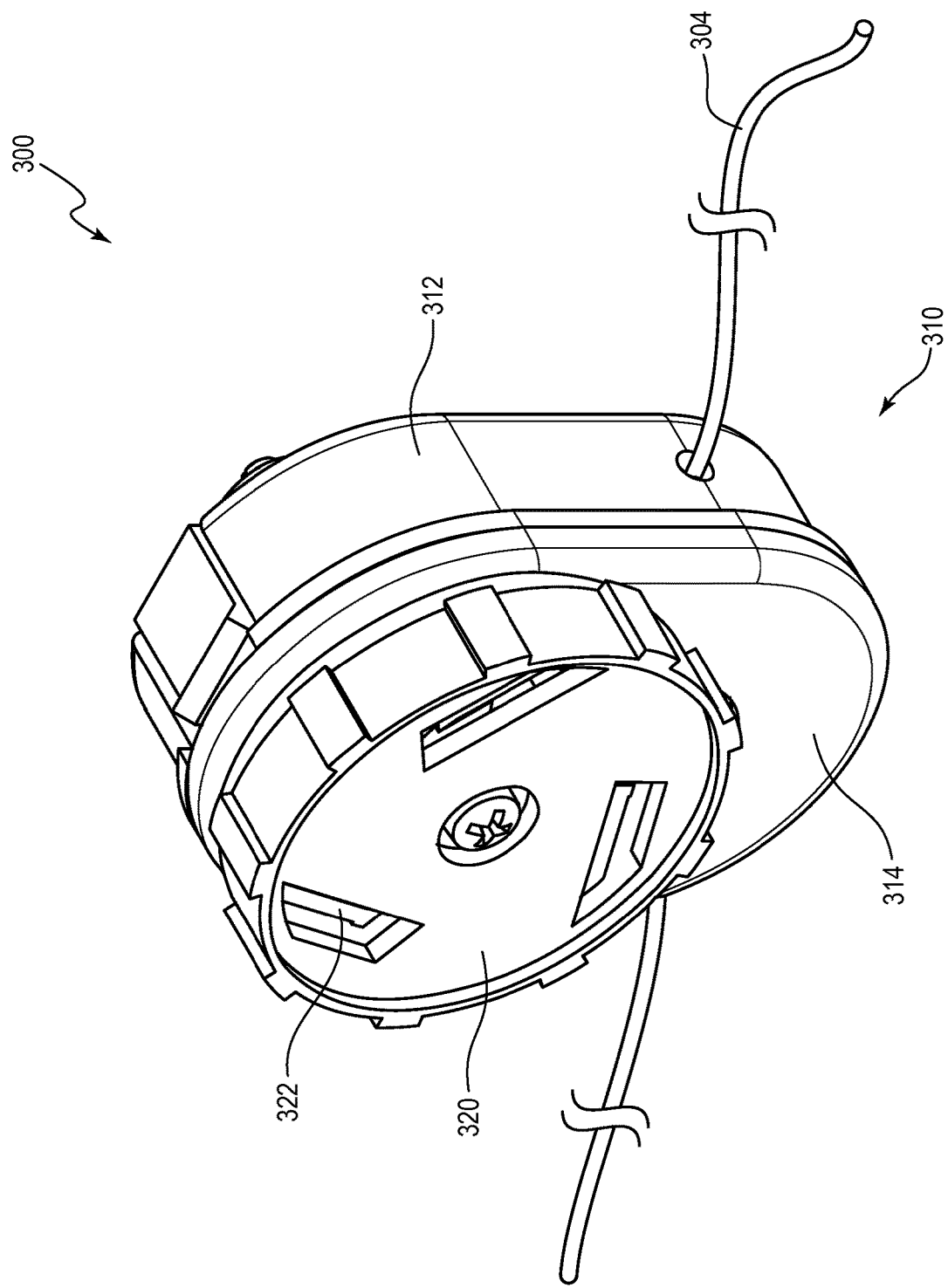
FIG. 7 is a front perspective view of an embodiment of a tightening mechanism coupled with an embodiment of a tensioning line, wherein the tightening mechanism and the tensioning line are suitable for use with the embodiment of an adjustable prosthetic system depicted in FIG. 1.
Figure 8:
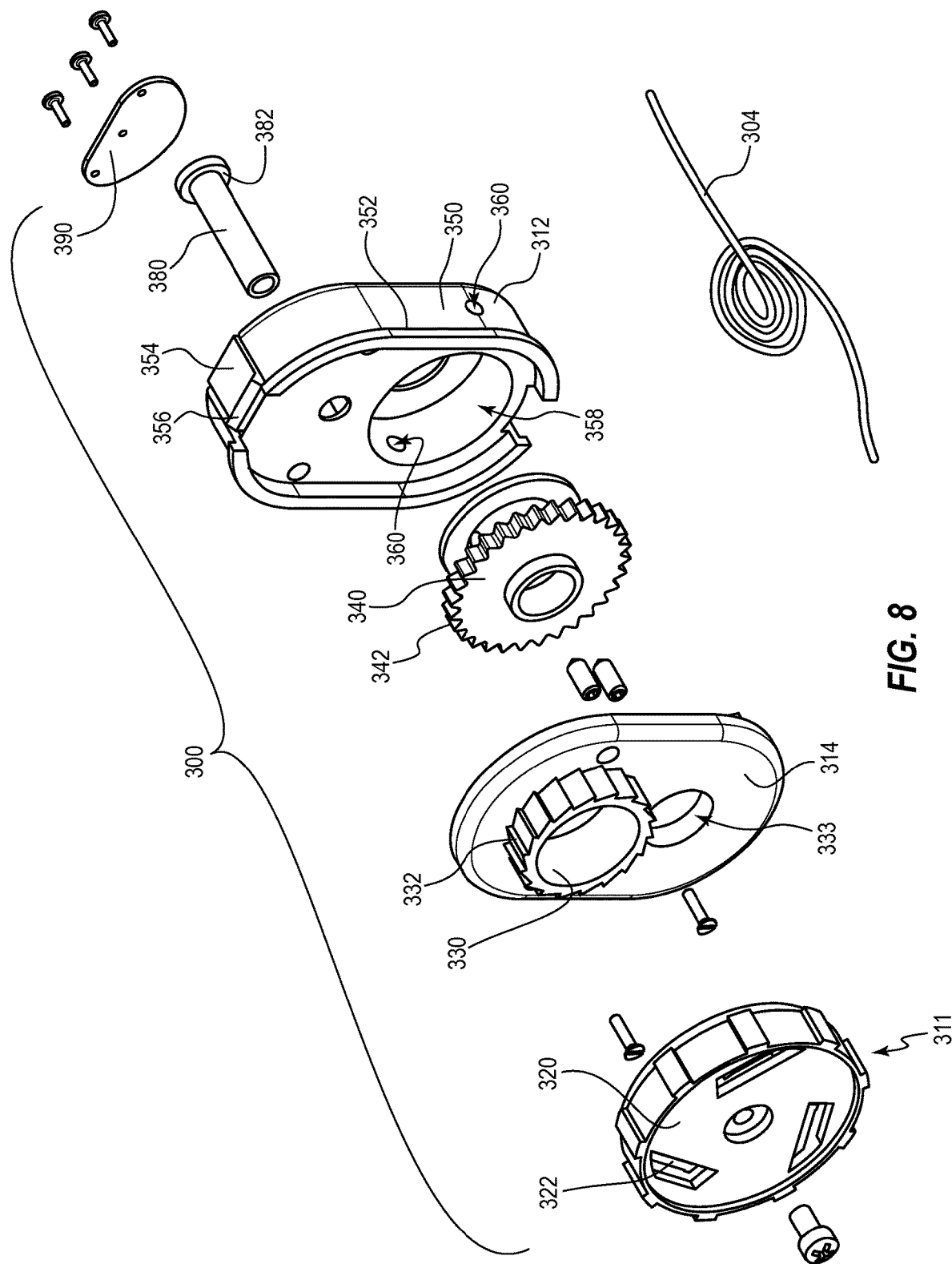
FIG. 8 is an exploded front perspective view of the tightening mechanism and the tensioning line of FIG. 7.

With reference to FIGS. 7-11, a ratcheting device 300 can include a housing 310 and an actuator 311. In FIGS. 7 and 8, the ratcheting device 300 is shown coupled with a tensioning line 304. The actuator 311 is operable to selectively rotate in a first direction (e.g., clockwise) so as to gather the tensioning line 304 within the housing 310 when the actuator is in an engaged state, and is operable to permit a release of tension from the tensioning line 304 (whether full or partial) when the actuator is in a tension-release state.

Figure 9:
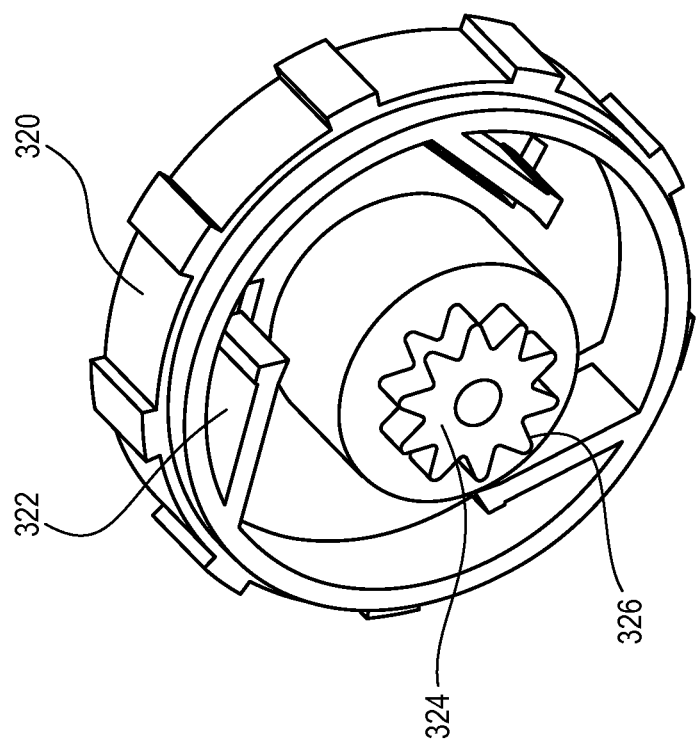
FIG. 9 is a rear perspective view of an embodiment of a knob portion of the tightening mechanism of FIG. 7.
Figure 11:
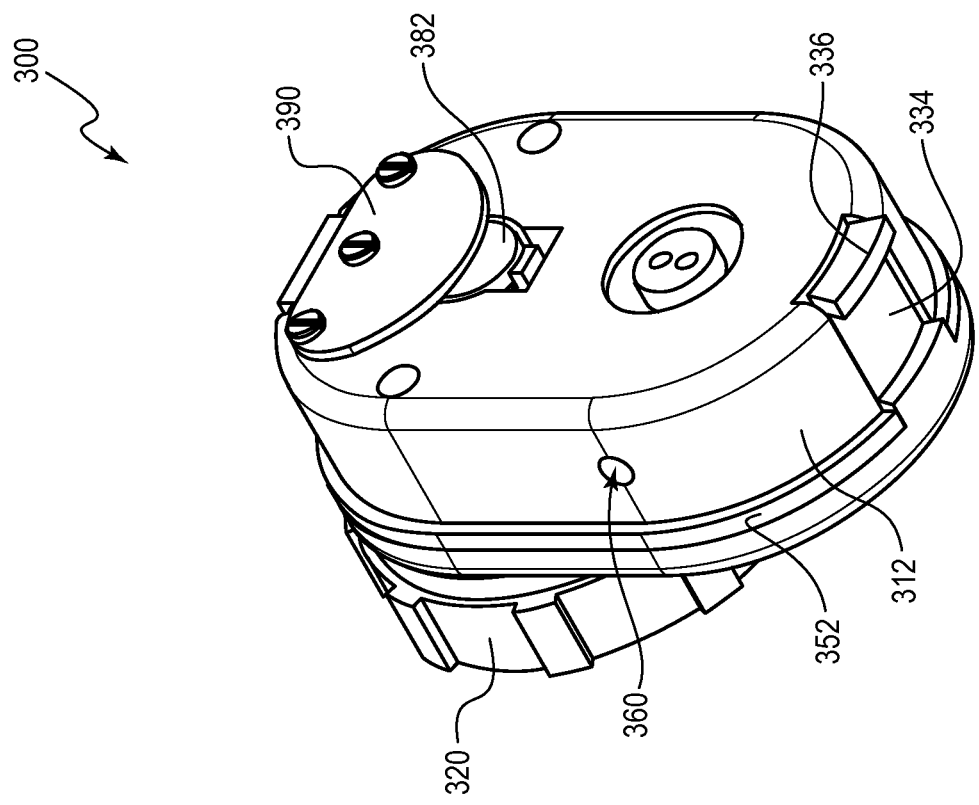
FIG. 11 is a lower rear perspective view of the tightening mechanism of FIG. 7.

The actuator 311 includes a knob 320 that has a plurality of pawls 322. As shown in FIG. 9, the knob 320 includes a gear 324 with teeth 326. The housing 310 includes a cover 314 and a base 312 that cooperate with each other to secure a spool 340 therein. The cover 314 includes an upward protrusion 330 that has a plurality of teeth 332 that are configured to engage with the pawls 322 so as to permit the knob 320 to move in a first direction relative thereto but to prevent movement in a second direction relative thereto. The cover 314 defines an opening 333 that can receive a portion of spool 340 so as to maintain an alignment thereof. The cover 314 further defines a resilient arm 334 that defines a tab 336 at an end thereof (see FIGS. 10 and 11).

The base 312 of the housing 310 defines a cavity 358 for receiving the spool 340. The base 312 defines two openings 360 through which the tensioning line 304 can enter the housing 310 so as to wrap around the spool 340. The spool 340 includes teeth 342 that are configured to engage with the teeth 326 of the knob 322 so as to rotate the spool 340.

The base 312 of the housing 310 includes a base region 350 that is bordered by a flange 352 at an upper end thereof. The base 312 includes a resilient arm 354 that includes a tab 356 at an upper end thereof.

Figure 10:
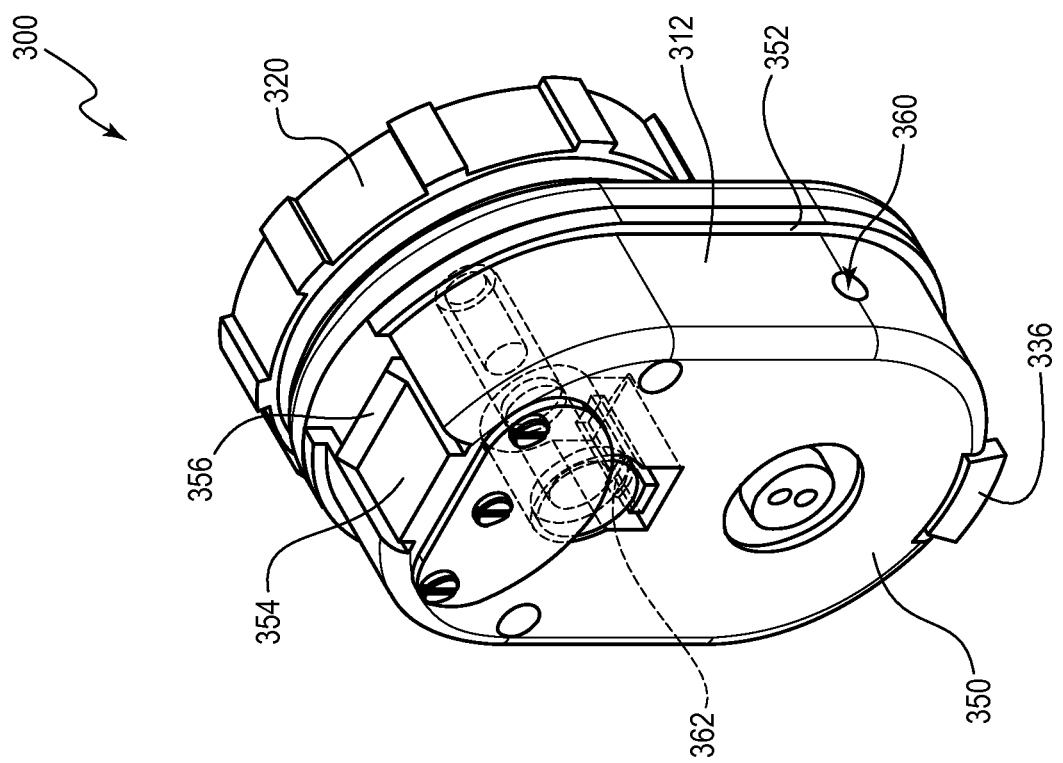
FIG. 10 is an upper rear perspective view of the tightening mechanism of FIG. 7.

A post 380 can extend through the base region 350 of the base 312 and can be secured to the knob 320 via a screw. A plate 390 can be attached to the base 312 so as to prevent the post 380 from being removed from the base 312. The post includes a flange 382 (see FIGS. 8 and 11), and the base 312 defines a resilient catch 362 (FIG. 10). When the knob 320 is pushed downwardly, the flange 382 of the post 380 bypasses the catch 362 and is held in place thereby. The knob 320, when in this position, is in an engaged or tightening state. When in this state, the pawls 322 of the knob 320 are engaged with the teeth 332 of the protrusion 330 of the cover 314.

With sufficient force, the knob 320 can be pulled outwardly so as to move the flange 382 of the post 380 upwardly past the catch 362. When in this position, the knob 320 is in the tension-release state, as the pawls 322 no longer engage the teeth 332 and the teeth 326 of the gear 324 of the knob 320 no longer engage the teeth 342 of the spool 340. The spool is thus free to rotate in a direction opposite of that used to tighten the tensioning line 304, and may do so, for example, until sufficient tension is released for the rotation to terminate.

The ratcheting device 300 thus permits rotation of the knob 320 in a single direction while limiting rotation of the knob 320 in the opposite rotation direction. Moreover, the ratcheting device 300 may allows incremental adjustments feature to tension in the line 304. A larger number of teeth 332 can allow for small increments of change in the tension. In various embodiments, the teeth can permit anywhere from 1 to 30 degrees of rotation, which can result in a small amount of change in tension in the tensioning line 304 with each step. Such capability of applying incremental amounts of tension in the tensioning line 304 may permit a user to tighten portions of the sockets 110, 120 incrementally, as needed or as desired, as portions of the residuum change size.

Figure 13:
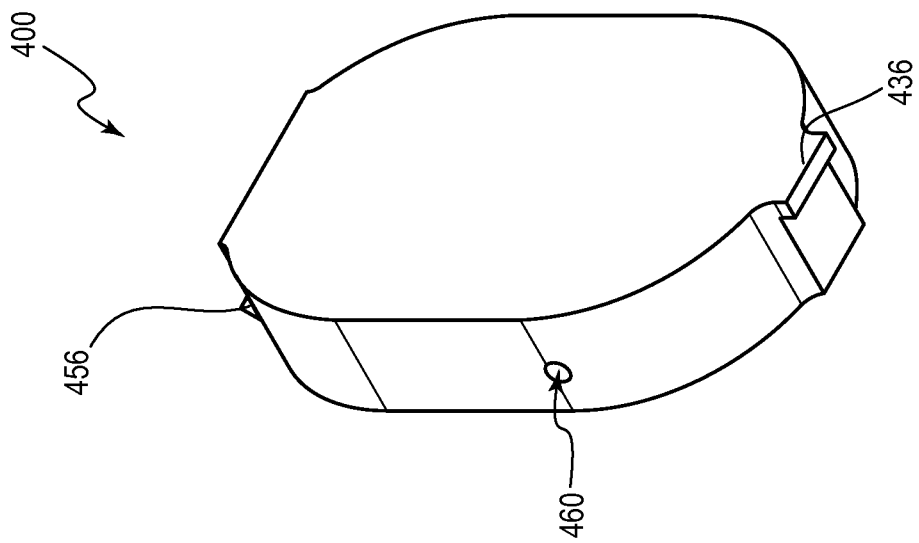
FIG. 13 is a lower rear perspective view of the template of FIG. 11.
Figure 12:
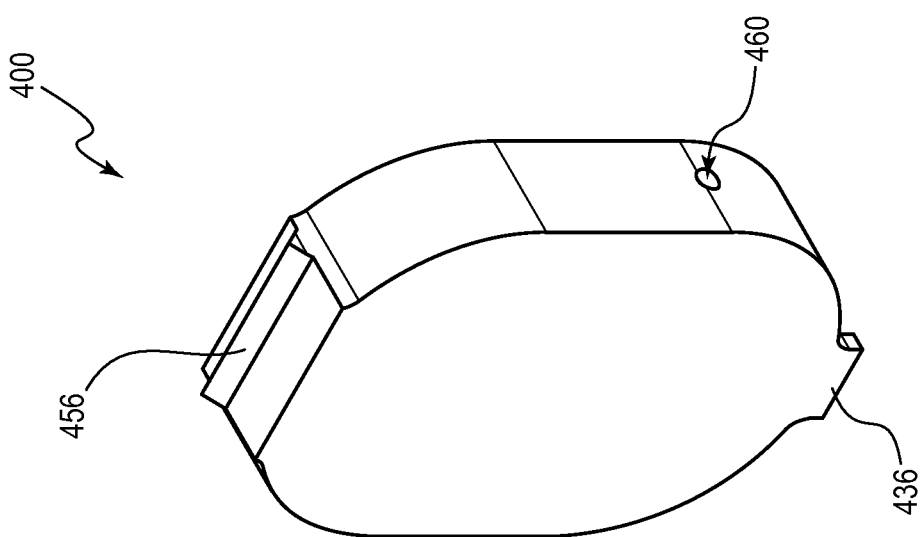
FIG. 12 is an upper rear perspective view of an embodiment of a template that is shaped to resemble a portion of the tightening mechanism of FIG. 7.

FIGS. 12 and 13 illustrate an embodiment of a dummy or template 400 that can be used in a lamination procedure. The template 400 can be used to form a cavity dimensioned to receive and secure the housing 310 of the ratcheting device 300. An outermost perimeter of the template can be the same size as or larger than an outermost perimeter of the base region 350 of the base 312 such that the cavity formed by the template within a wall structure material is sufficiently large to receive the base region 350 of the housing 310. The template 400 can further include features that correspond with those of the housing 310. In particular, the template 400 can define an upper ridge 456 and a lower protrusion 436 that can correspond in shape and/or size with the tabs 356, 336 of the housing, respectively.

The template 400 can define a channel 460 that can correspond in size to the openings 360 of the housing 310. A position of the channel 460 relative to the template 400 can correspond with a position of the openings 300 relative to the housing 310. The channel 460 can extend through at least a portion of the template 400 from either side thereof.

The template 400 can comprise any suitable material, and may be substantially rigid. The template 400 may be configured to readily release from a hardened resin material. In some embodiments, the template comprises a plastic, such as a thermoplastic (e.g., Delrin®).

FIGS. 14A-14J illustrate various stages of an illustrative method in which the template 400 can be used in the formation of a socket. Some portions of the procedures are known in the art, and thus will not be described in detail. It is also noted that many different materials and procedures are possible, and that the following discussion is merely illustrative of examples of the same.

Figure 14B:
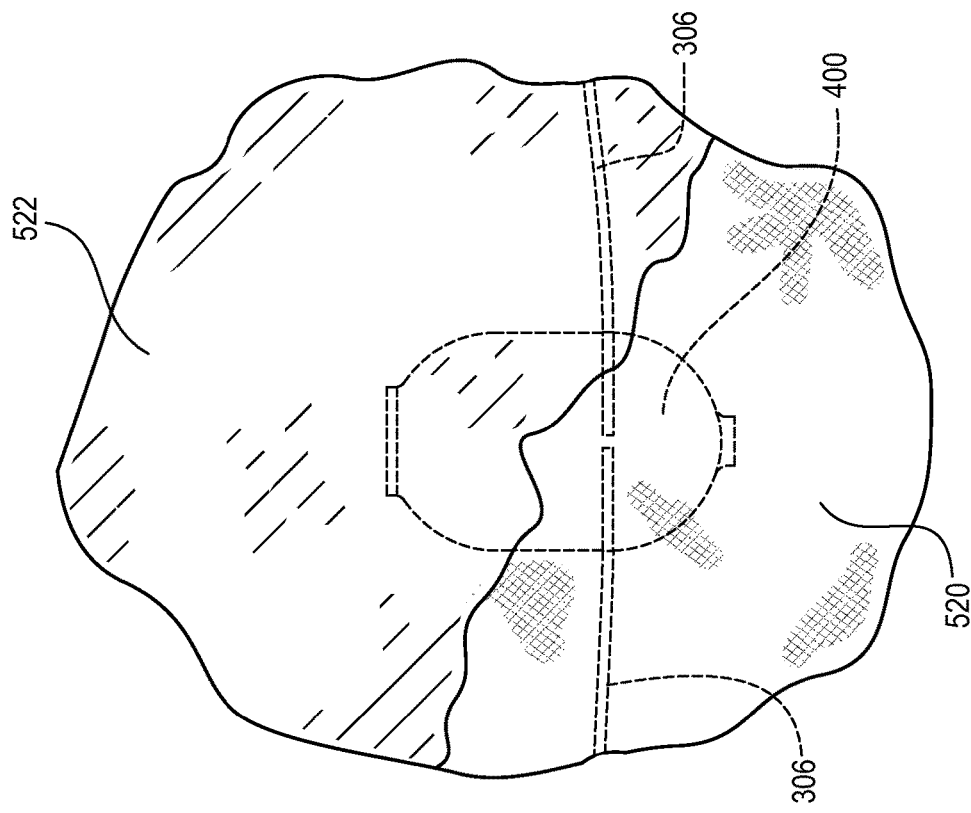
FIG. 14A-14J are schematic plan views of various stages of an illustrative method for manufacturing an embodiment of an adjustable socket.
Figure 14A:
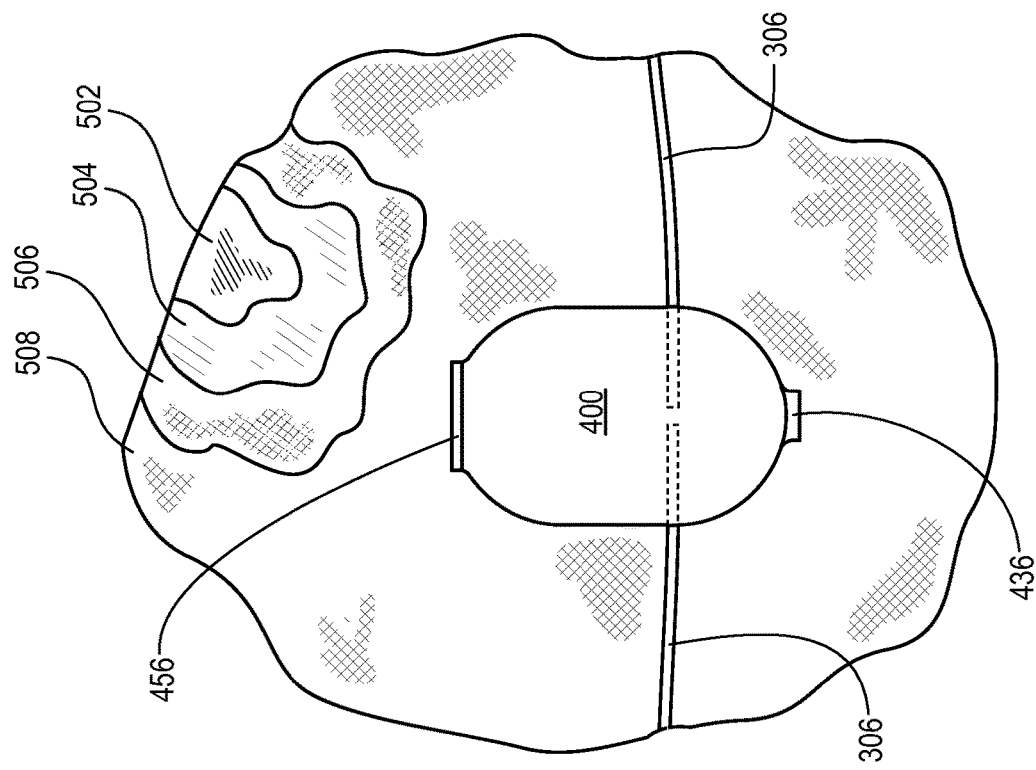

FIG. 14A illustrates placement of the template 400 and a guide 306 at a desired position during a lay-up procedure. Dried and hardened plaster mold 502 that represents the residuum is covered with a barrier layer 504 of flexible plastic or foam, such as a PVA bag. Another layer 506 of plastic, such as a PVA bag is positioned over the layer 504. These layers are covered by one or more layers of fibers and/or fabric, such as a carbon fiber layer 508. The template 400 may be attached to the layup in any suitable manner, such as by an adhesive. The guide 306 is routed about the plaster mold 502 in any desired guide path, such as, for example, those discussed above. Either end of the guide 306 is inserted deeply into the template 400 (i.e., into the channel 460). The guide 306 can form a tight fit with the channel 460 so as to prevent liquid resin from entering therein.

FIG. 14B shows that another layer 520 of one or more materials (e.g., fabric and or fibers) may be provided over the template 400 and the guide 306 such that these items are sandwiched therebetween. Another barrier layer 522 of plastic is provided over the layer 520.

Figure 14C:
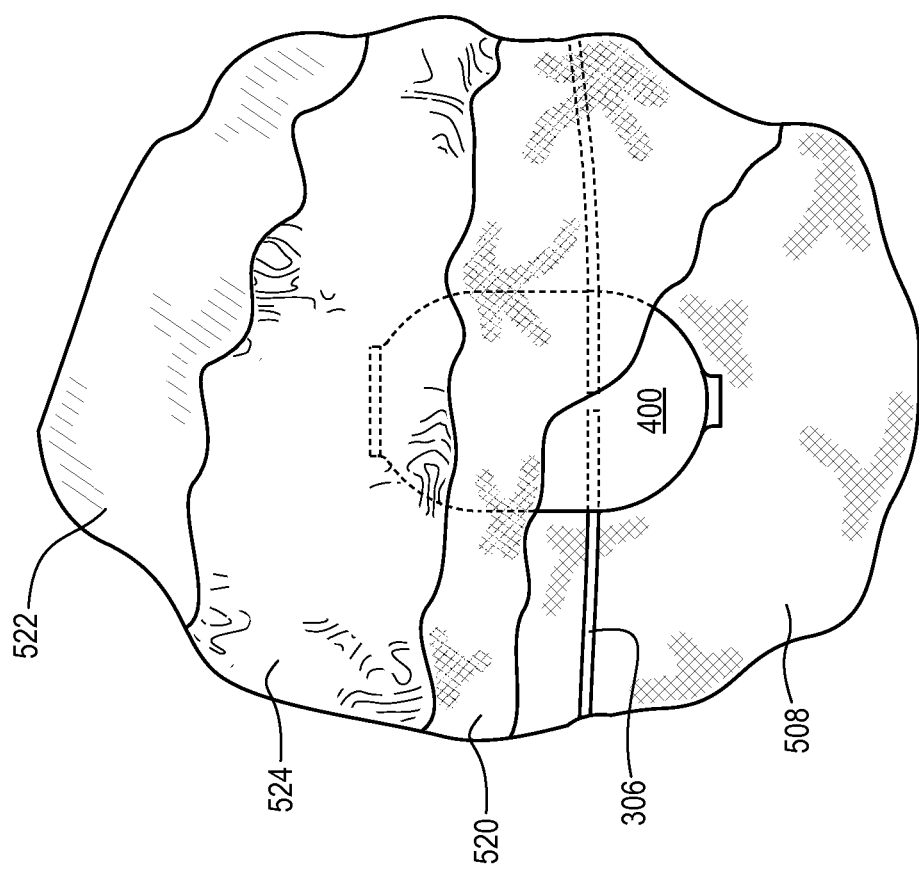

FIG. 14C illustrates the introduction of liquid resin 524 about the template 400 and the guide 306. The resin 524 can saturate the fabric layers 508, 520, and can be constrained by the barrier layers 506, 522.

Figure 14E:
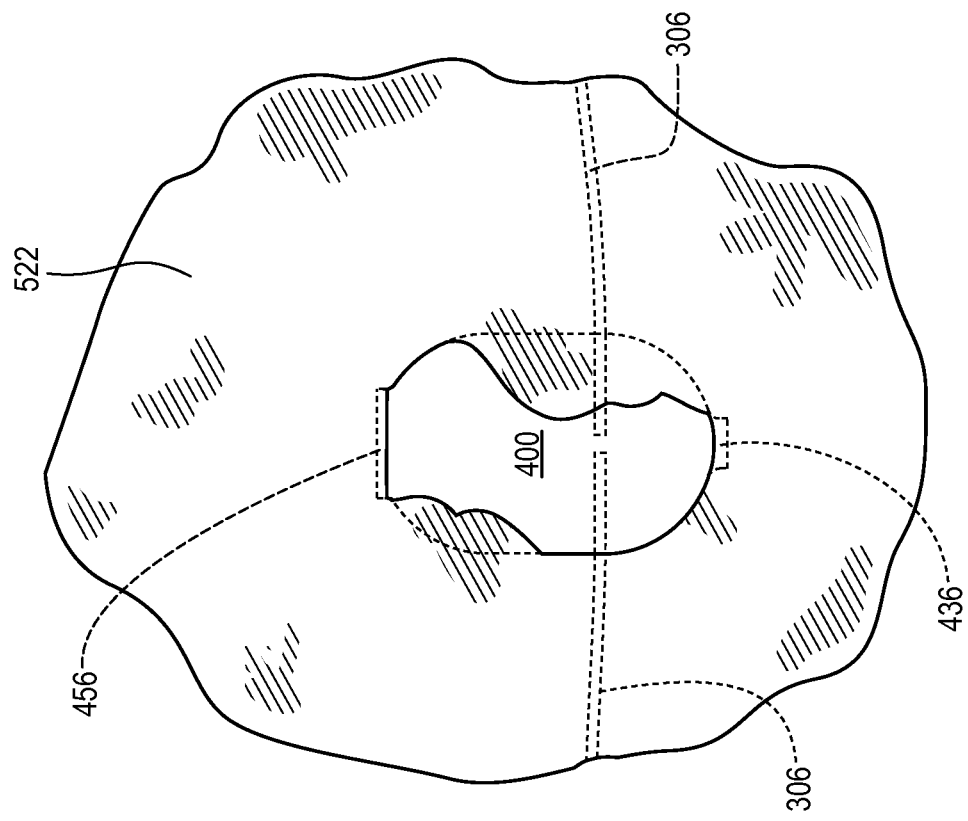
Figure 14D:
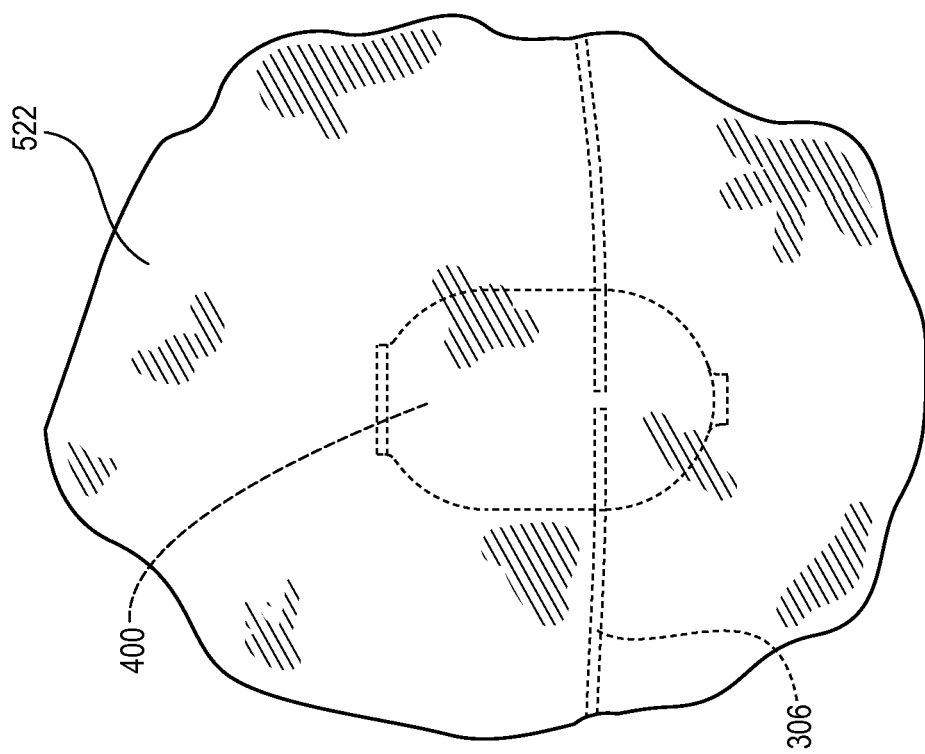

FIG. 14D shows the hardened or cured resin 522 and the barrier layers 506, 522 removed. The template 400 and the guide 306 are thus positioned within a single laminated layer.

FIG. 14E shows a portion of the resin 522 removed from above the template 400. The resin 522 can be removed in any suitable manner, such as by sanding or grinding. Caution may be used to grind the resin down only enough so as to expose the top surface of the template 400.

Figure 14G:
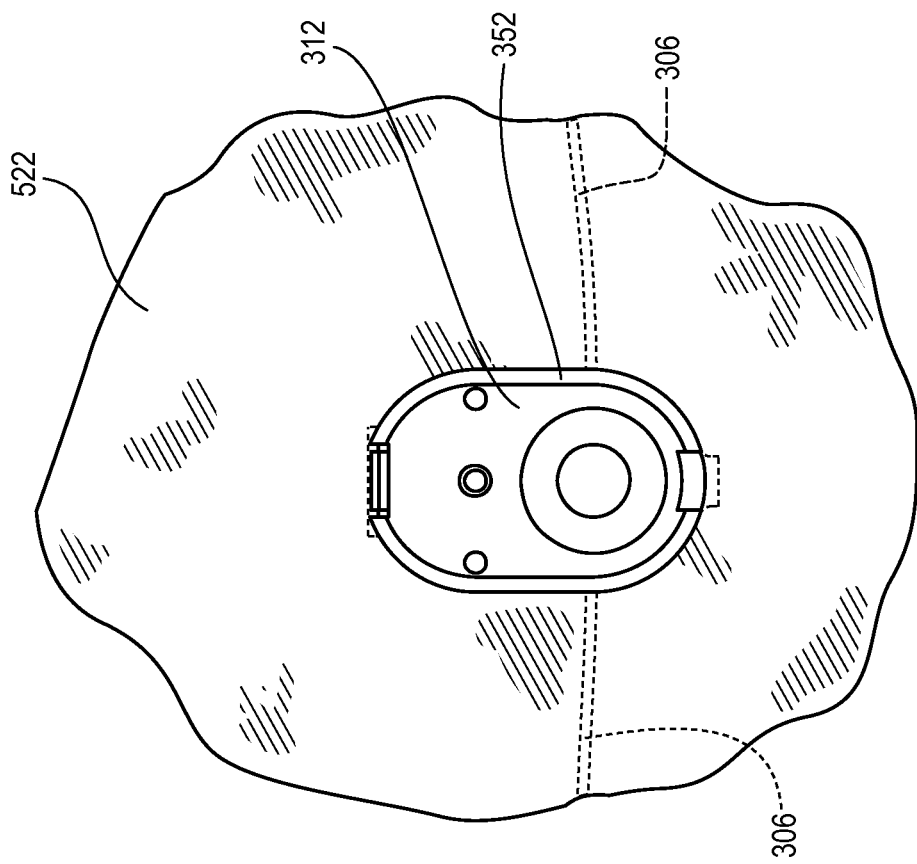
Figure 14F:
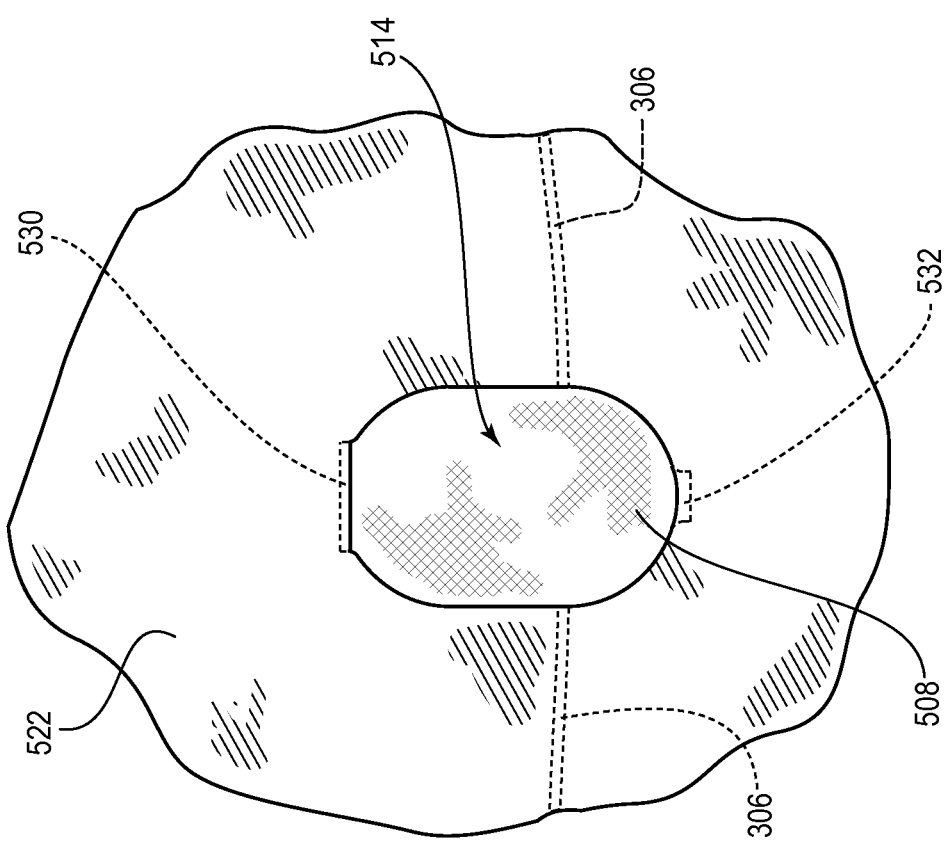

FIG. 14F shows a stage after removal of the template 400, which forms a void or cavity 514 in the laminated wall structure. The guide 306 remains on the original guide path that it defined during layup. An upper recess 530 and a lower recess 532 of the cavity 514 are shown. These recesses 530, 532 have been formed by the upper ridge 456 and a lower protrusion 436 of the template 400.

FIG. 14G shows the base 312 of the housing 310 inserted into the cavity 514.

Figure 14H:
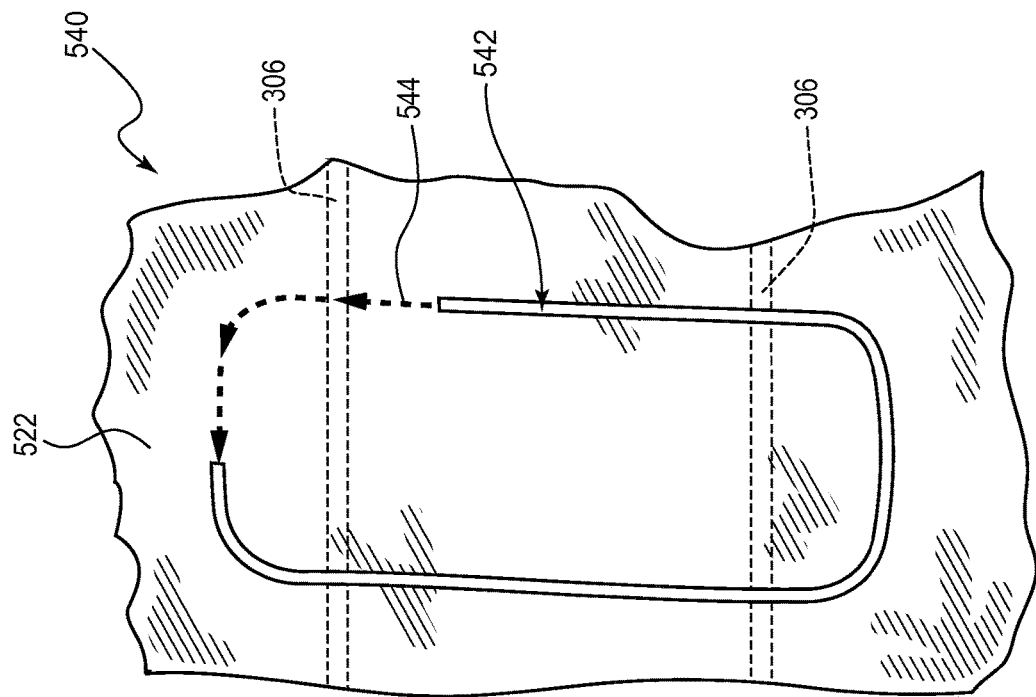

FIG. 14H shows another portion 540 of the laminated wall structure that is spaced from the base 312. The wall structure is cut along a cut path 544. The cut path 544 can have any desired pattern so as to form a panel of a desired shape. A gap 542 thus may be formed between the panel portion of the wall structure and a receptacle portion thereof. The cut path 544 can extend through the guide 306 such that the guide is cut during formation of the panel. Any suitable number of panels can be cut from other portions of the wall structure in the same manner.

In some embodiments, a substantially linear tool (not shown) may be used to create the cut path 544. In some embodiments, care may be taken to ensure that linear tool is oriented substantially perpendicular to a single plane during creation of the gap 542, which may facilitate movement of the panel relative to the surrounding region of the receptacle.

Figure 14J:
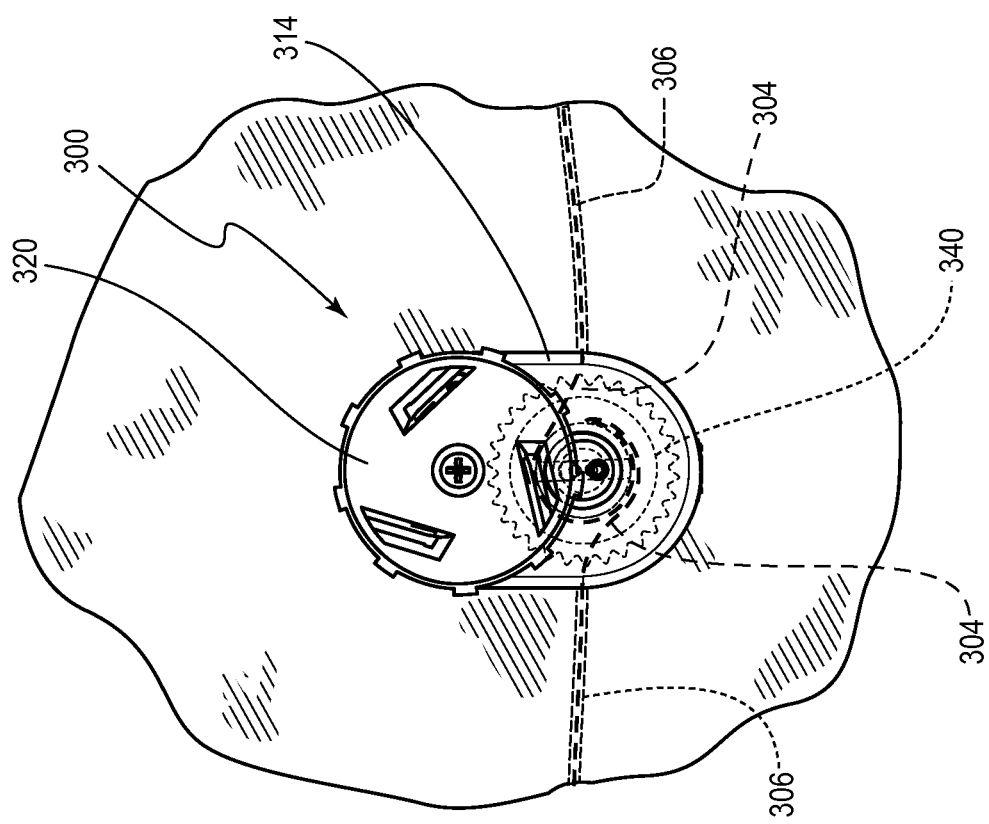
Figure 14I:
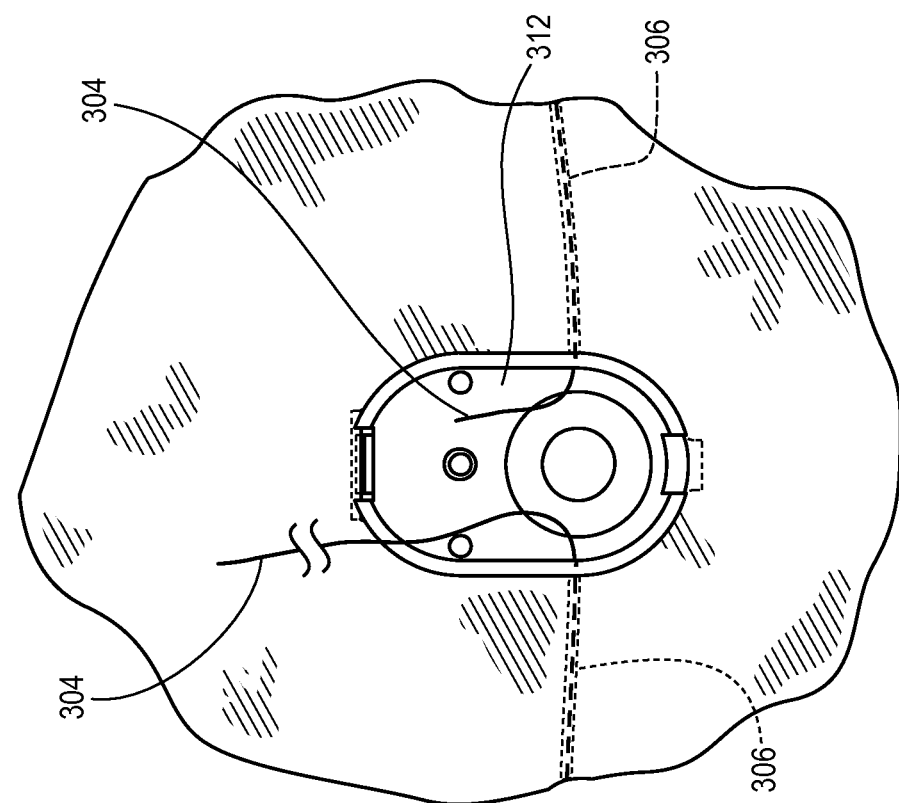

FIG. 14I shows that the tensioning line 304 has been threaded through the entire guide 306. In particular, the line 304 has been threaded through the receptacle portion of the wall structure and also through the cut panel portion thereof.

FIG. 14J shows that the tensioning line 304 has been secured to the spool 340 and the housing cover 314 has been secured to the base 312. The ratcheting device 300 thus can be secured in place by insertion of the tabs 356, 336 into the recesses 530, 532. Additional and/or other methods for securing the ratcheting device 300 also may be employed, such as the use of adhesives. The tensioning line 304 can be tightened by rotation of the knob 320.

The foregoing method is an example of a single-lamination method. In other methods, multiple laminations may be performed. For example, with reference to FIG. 14A, in some embodiments, the template 400 may originally be secured to a first, laminated layer, rather than to unlaminated materials. The template 400 can then form a cavity in a second lamination layer into which the ratcheting device 300 is received. The foregoing methods may also be used at other positions of a socket in order to create multiple independent adjustment zones, such as, for example, the distal and proximal zones 156, 158 discussed above.

Figure 15:
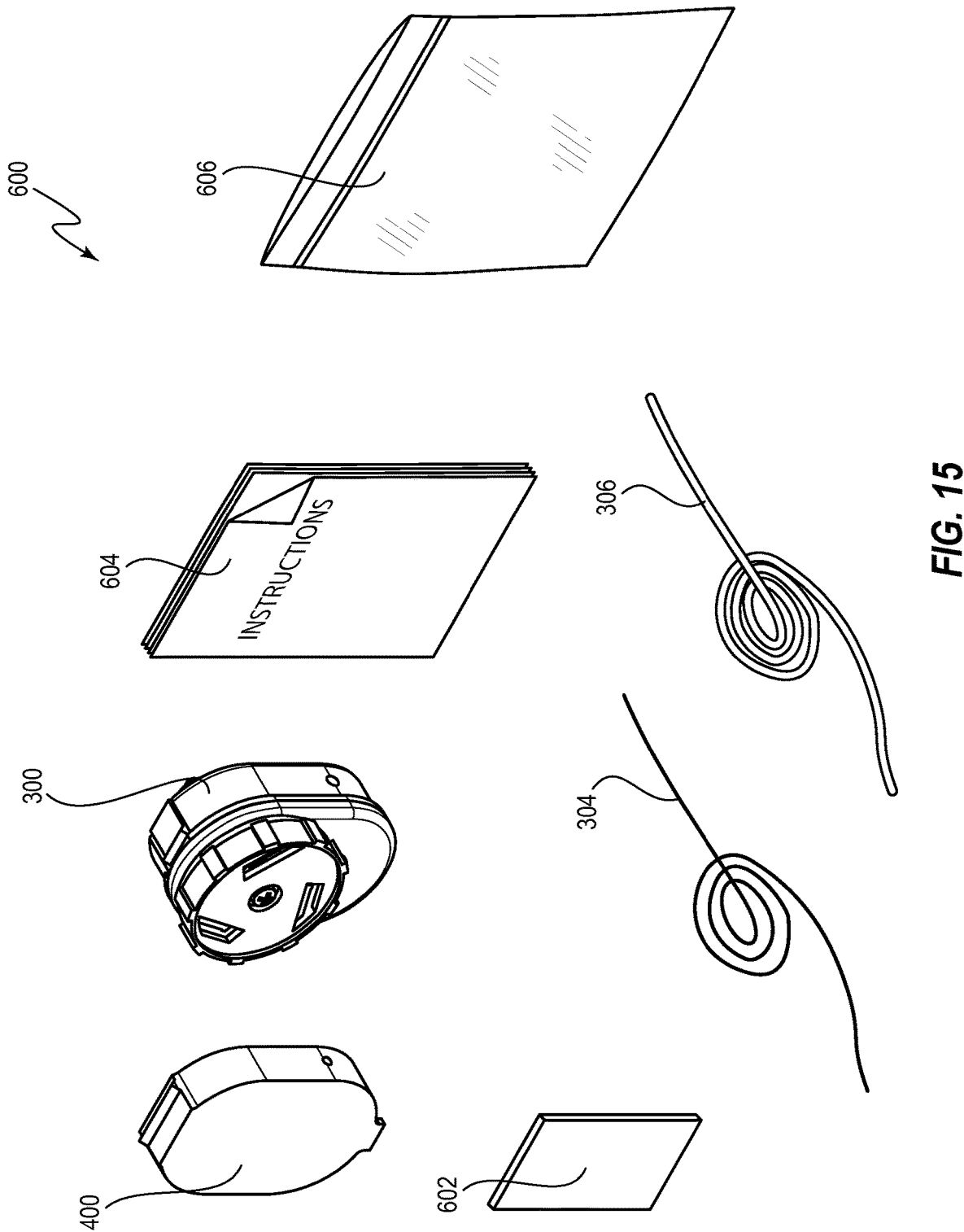
FIG. 15 is perspective view of an embodiment of a kit that is configured to be used in the manufacture of an adjustable socket.

FIG. 15 illustrates that a kit 600 may include materials that can be used in a lamination procedure, such as those just described. The kit 600 can include any suitable combination of the ratcheting device 300, the template 400, an adhesive 602 which can be used in placement of the template 400, the tensioning line 304, the guide 306, and instructions 604. Additional items may also be included in the kit 600. For example, in some embodiments, a pad (not shown) that can be attached to an inner surface of a panel that is formed from the laminated structure can also be included. The instructions 604 can include directions for performing any and/or all of the steps of a method for creating an adjustable socket, such as any of the procedures discussed above. In other or further embodiments, the instructions 604 may provide directions for accessing such directions. For example, the instructions may list a web address, a mailing address, and/or a telephone number that can be used to locate instructions for preparing a socket. One or more of the foregoing items can be included in and/or on (e.g., in the case of the instructions) the packaging 606.

Figure 16:
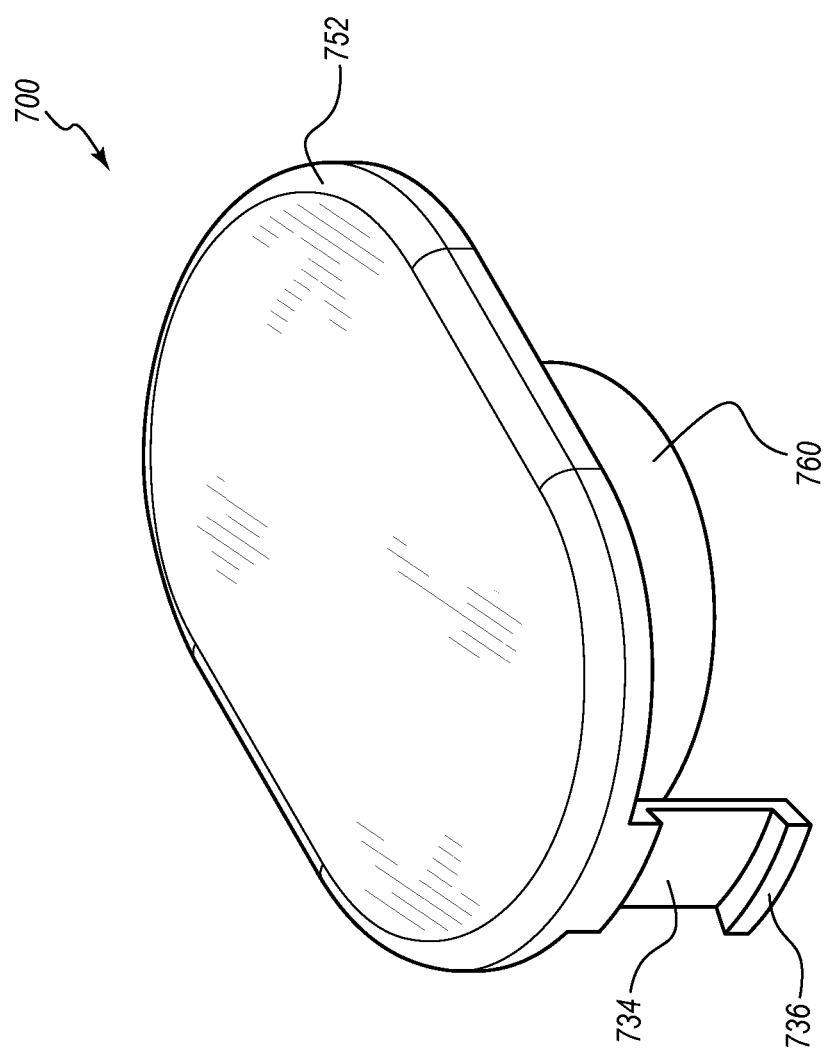
FIG. 16 is a perspective view of an embodiment of a cap template that is configured to be coupled with a base portion of the tightening mechanism of FIG. 7.

FIG. 16 illustrates an embodiment of another template 700 that can be used in a laminating procedure. The template 700 can serve as a cap to prevent liquid resin from entering the base 312 of the housing 310. In particular, with reference again to FIG. 14A, in some procedures, the base 312 and the template 700 can be joined together and can take the place of the template 400. Accordingly, the base 312 is laminated directly in place. The template 700 can include a protrusion 760 that extends into and fills the base 312. The template 700 can also include a flexible arm 734 and tab 736 that resemble the arm 334 and the tab 336 described above. As can be appreciated from the foregoing, other stages of procedures for using the template 700 in the creation of a wall structure can proceed in manners similar to or the same as those shown and discussed with respect to FIGS. 14B-14E (where the coupled base 312 and template 700 take the place of the template 400), and FIGS. 14G-14J. With particular reference to FIG. G, it can be appreciated that removal of the template 700 creates a void within the laminated structure, which void corresponds with the interior cavity of the base 312.

Figure 17:
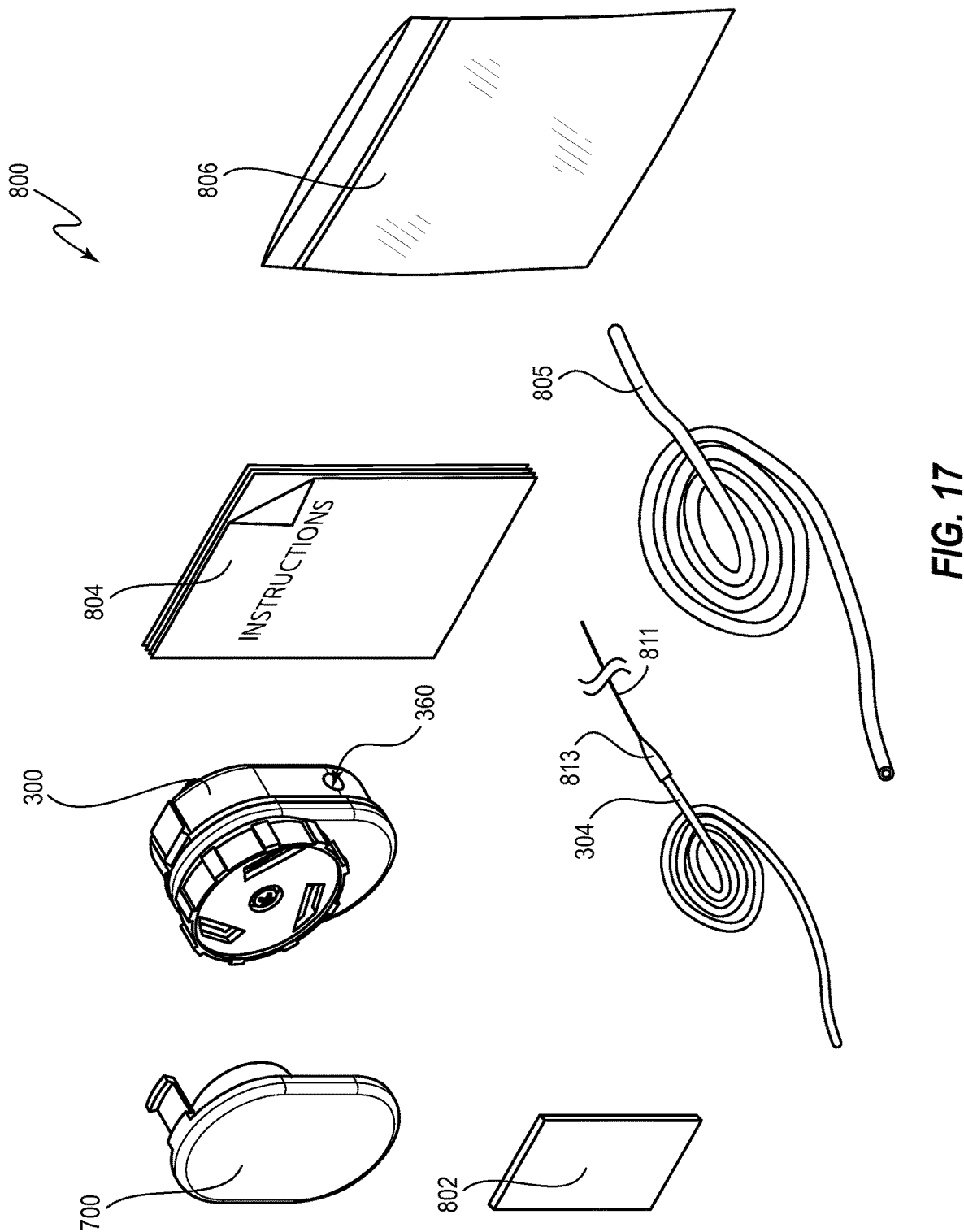
FIG. 17 is a perspective view of another embodiment of a kit that is configured to be used in the creation of an adjustable socket.

FIG. 17 illustrates another embodiment of a kit 800 that includes materials that can be used in a lamination procedure, such as those described above. The kit 800 can include any suitable combination of the ratcheting device 300, the template 700, an adhesive 802 which can be used in placement of the base 312, a tensioning line 304, a guide 805, and instructions 804, any or all of which can be contained in packaging 806. The illustrated ratcheting device 300 is a more heavy duty device. It includes a larger opening 360 and can be used with a different tensioning line 304 that may be wider and/or stronger. The tensioning line 304 may be a flexible material or cord that can benefit from a stiff threading wire 811 for threading through the guide 805. The threading wire 811 can be attached to the tensioning line 304 via any suitable connection 813. After threading of the tensioning line 304, the threading wire 811 and the connection 813 can be cut from the tensioning line 304.

Additional embodiments of adjustable prosthetic systems are discussed hereafter. In one example, a rotatable ratchet-type device is used in conjunction with a lace or cable member. The lace or cable member extends around a periphery, or at least a portion of a periphery, of the socket and is retained in place by a plurality of guide members. Rotation of the ratchet member collects a portion of the lace or cable member and applies tension in the lace or cable member that results in application of a compressive force to the socket and/or the patient's limb. In at least one example, the compressive forces are applied in the front-to-back direction (i.e., in either or both of the anterior and posterior directions). Application of such forces can reduce the distance between the anterior and posterior portions of the socket, thereby tightening those portions of the socket against the patient's limb to reduce a gap between the patient's limb and the socket that otherwise is present due to, for example, shrinkage of the limb during the course of a day.

In many prosthetic applications, in particular in transfemoral and transtibial prosthesis, maintaining contact between the residuum and the socket in the front-to-back direction has a greater impact on stability and comfort for the prosthesis as compared to such contact in the lateral (i.e., side-to-side) direction. In at least some arrangements, certain example adjustment systems and methods emphasize adjustability of the socket fit relative to the residuum in the front-to-back direction. In at least some examples, the adjustment systems and methods are configured to adjust the socket fit in the side-to-side direction.

Typically, a majority of the volume loss in a transtibial residuum is in the soft tissue, which primarily is composed of the gastrocnemius muscle. The gastrocnemius muscle is arranged mostly along the posterior portion of the residuum, thus making adjusting in the front-to-back direction sometimes of primary concern as compared to adjustment in the side-to-side direction. However, side-to-side adjustment can also be important to stabilize the knee joint and the bony portions (e.g., tibia and fibula bones) of the residuum.

In some example configurations, adjustment systems may be mounted to an exterior surface of the socket portion of a prosthesis. In other arrangements, at least portions of the adjustment system are incorporated integral within a portion of the socket, such as, for example, within a layer or subset below an outer, exterior surface of the socket. The socket may comprise a plurality of layers that each provide a separate function. For example, a portion of the adjustment systems, such as, a lace or cable member, may be positioned between layers of the socket and extend within and move relative to a pathway defined between the layers.

Although numbering of the drawings associated with the following text, while internally consistent, varies from that set forth in the foregoing disclosure, it should be understood that features that are named similarly or identically to the features described above can be similar to or the same as those described above.

FIGS. 18-23 illustrate another embodiment of an adjustable prosthetic system 900. The system 900 includes a prosthetic device 912, one or more tensioning lines 914, a plurality of guide members 918a-918g, and a tightening mechanism 916. The prosthetic device 912 includes a socket 920, a support or pylon 922, and an ankle-foot structure 924. The socket 920 defines a cavity 928 having an upper opening 930 that provides access to the cavity 928. The socket 920 also includes a support attachment 932 to which the support or pylon 922 is mounted. The socket 920 includes anterior and posterior portions or sides 934, 936, and lateral and medial portions or sides 938, 940. The cavity 928 is accessible at an upper end of the socket 920, and the support attachment 932 is positioned at a lower end thereof.

The tightening mechanism 916 includes a base 950 and a knob 952. Portions of the tensioning line 914 extend into the tightening mechanism 916. The tightening mechanism 916 is configured to collect portions of the tensioning line 914 within the tightening mechanism 916. In certain embodiments, rotation of the knob 952 draws the tensioning line 914 into the tightening mechanism 916 so as to wrap the tensioning line 914 about a spool member. For example, the tightening mechanism 916 can operate in a manner such as the ratcheting device 300 discussed above.

The tightening mechanism 916 is positioned along the posterior portion 936 of the socket 920. In certain embodiments, positioning the tightening mechanism 916 at this location can be advantageous for trying to conceal the tightening mechanism and positioning it at a location that is away from obstacles or other contact during normal use of the prosthetic device 912. Many other locations are possible for the tightening mechanism 916, such as, for example, any location along the other sides 934, 938, 940 and/or at any desired vertical or peripheral position.

A guide member 918a is positioned at the anterior portion 934 of the socket 920. First and second posterior guide members 918b, 918c are positioned along the posterior portion 936 of the socket 920 at positions that are vertically spaced from each other. Guide members 918d, 918e that are positioned on the opposing lateral and medial portions 938, 940, respectively, and are not configured to substantially change a direction of the tensioning line 914. Additional guide members 918f, 918g are also positioned on the lateral and medial portions 938, 940, and are configured to change a direction of the tensioning line 914. The guide members 918d, 918e are spaced vertically from the guide members 918f, 918g, and are slightly forward thereof.

The system 900 can apply a compressive force to the socket 920 at numerous locations. For example, compressive force can be applied at one or more positions along the posterior portion 936 of the socket 920. In particular, compression may arise at the position where the tensioning line 914 passes through the guide members 918b, 918c. The system 900 may also apply compressive force along the anterior portion 934 of the socket 920 at a position where the tensioning line 914 passes through the guide member 918a. Compressive forces may also be applied to the socket 920 at locations where the tensioning line 914 passes through any of the guide members 918d-918g, although these compressive forces may not effect as great a change of a configuration of the socket 920.

Various configurations of the guide members may be used in managing movement of the tensioning member 914 about an exterior of the socket 920. For example, the guide member 918a can maintain the tensioning line 914 in a crossed configuration. Accordingly, a single guide member 918a may be used to cross the tensioning line 914 at a single location. The guide members 918f, 918g are configured to change a direction of the tensioning line 914. For example, in the illustrated embodiment, the guide members 918f, 918g change a direction of the tensioning line 914 by approximately 180 degrees. Any of the guide members 918a-918g may be mounted directly to an exterior of the socket 920 using, for example, fasteners, such as rivets or screws. In other embodiments, the guide members 918a-918g may be formed into a layer of the socket 920 such as in the embodiment shown in FIGS. 24 and 25.

In some embodiments, the socket 920 comprises a laminated material (e.g., is formed via a lamination process). In other embodiments, the socket 920 comprises a vacuum-formed plastic. In either case, the guide members 918a-918g, or at least portions thereof, may be attached to the socket 920 during the formation of the socket 920 or subsequent thereto. For example, in some instances, the guide members 918a-918g can be attached after formation of the socket 920, and may be used to retrofit the socket 920. The tightening mechanism 916, or at least a portion thereof, likewise can be attached to the socket 920 during formation of the socket or at a time thereafter.

Figure 22:
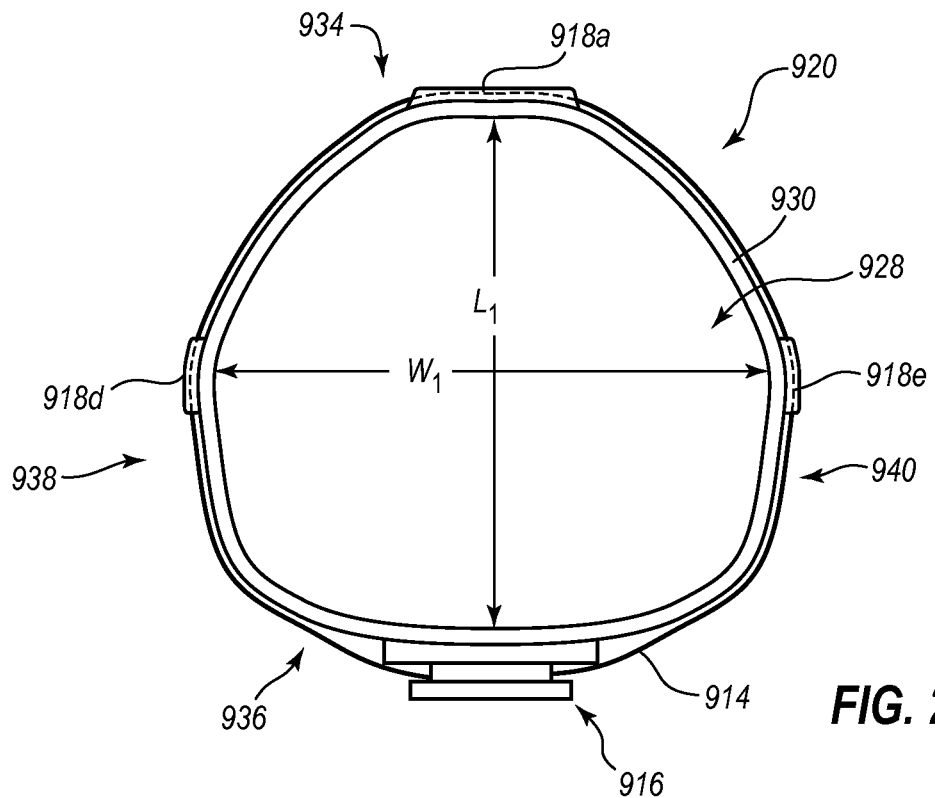
FIG. 22 is a top plan view of the adjustable prosthetic system of FIG. 18 showing the system in a first operational state.
Figure 23:
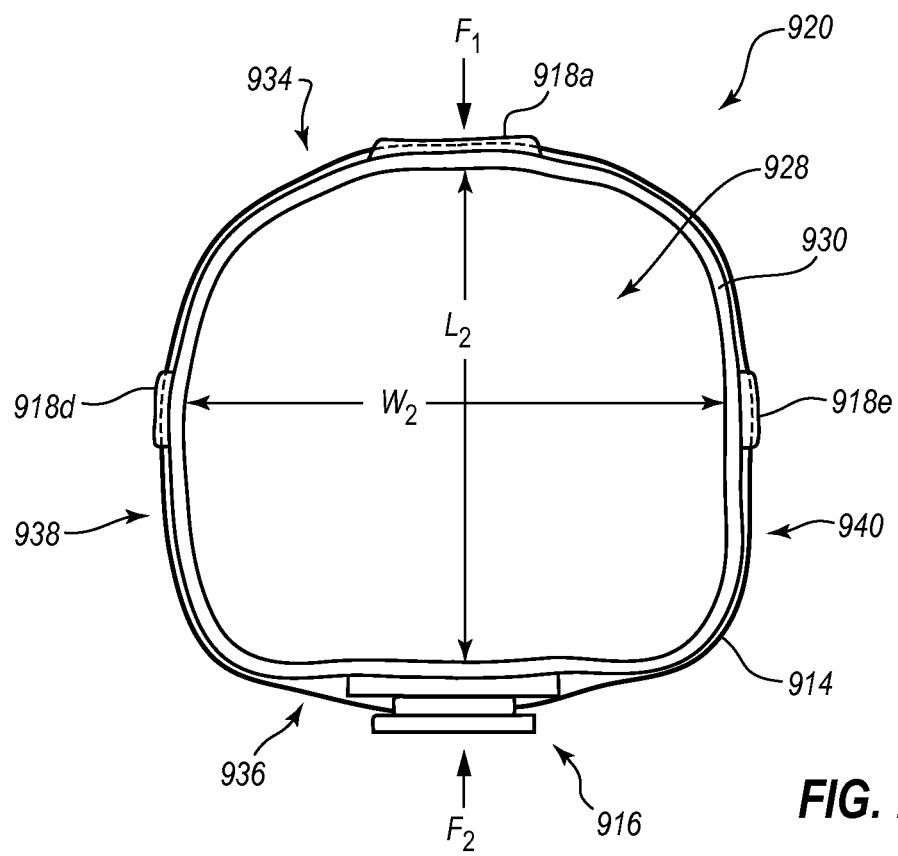
FIG. 23 is another top plan view of the adjustable prosthetic system of FIG. 18 showing the system in a second operational state.

FIGS. 22 and 23 illustrate a manner in which tightening of the tensioning line 914 with the tightening mechanism 916 may alter an interior shape of the socket 920. FIG. 22 illustrates the socket 920 in a rest state having a lateral width W1 and a length L1. Referring to FIG. 23, radially inward directed forces F1, F2 are applied at the anterior and posterior sides 934, 936, respectively, by tightening the tightening mechanism 916 to apply tension force in the tensioning line 914. This application of forces F1, F2 compresses the anterior and posterior sides 934, 936 toward each other to provide a length L2 that is less than the length of L1. A width W2 typically remains the same or decreases relative to the width W1 at the rest state shown in FIG. 22.

Figure 18:
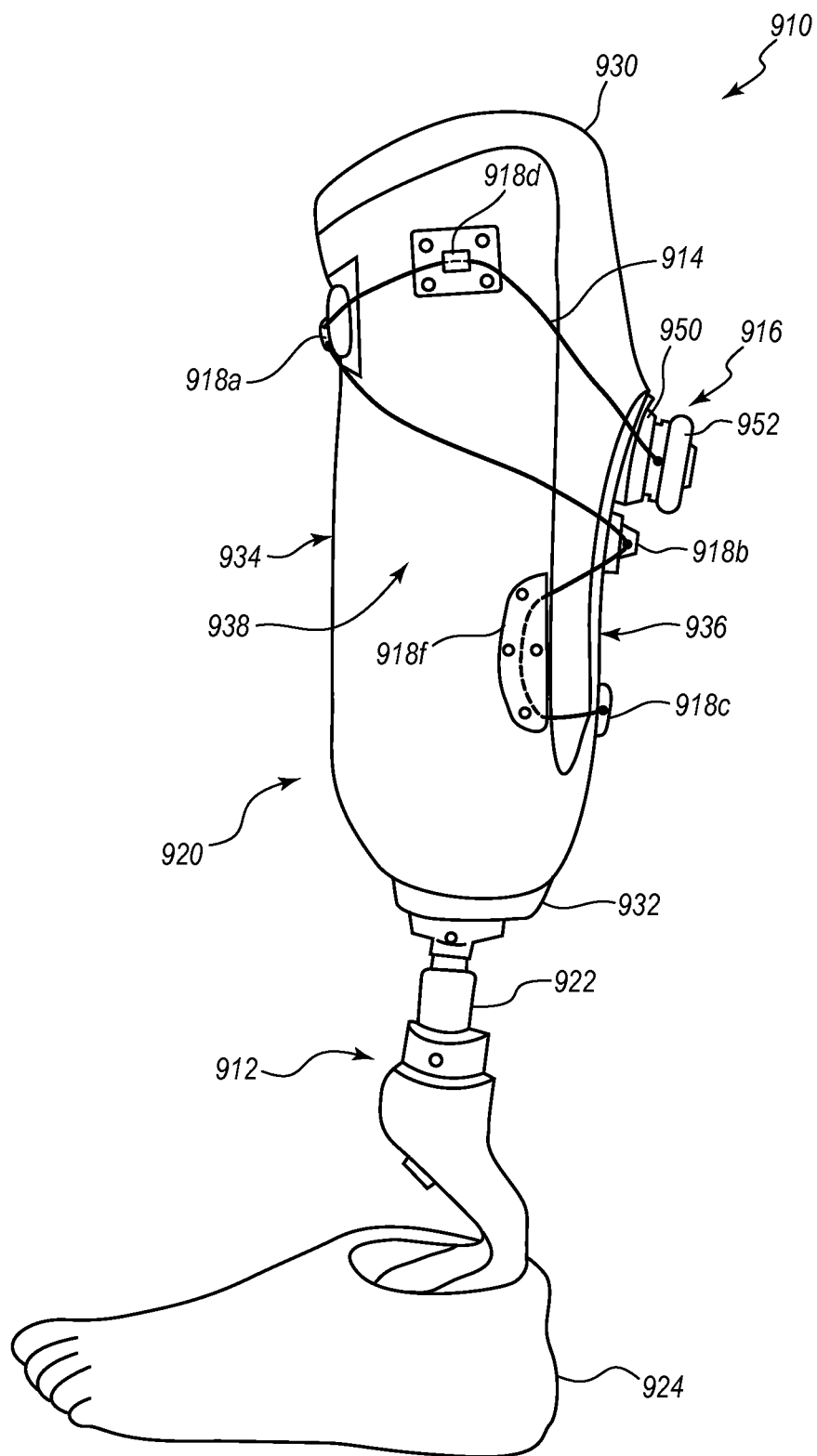
FIG. 18 is a left side elevation view of another embodiment of an adjustable prosthetic system.
Figure 19:
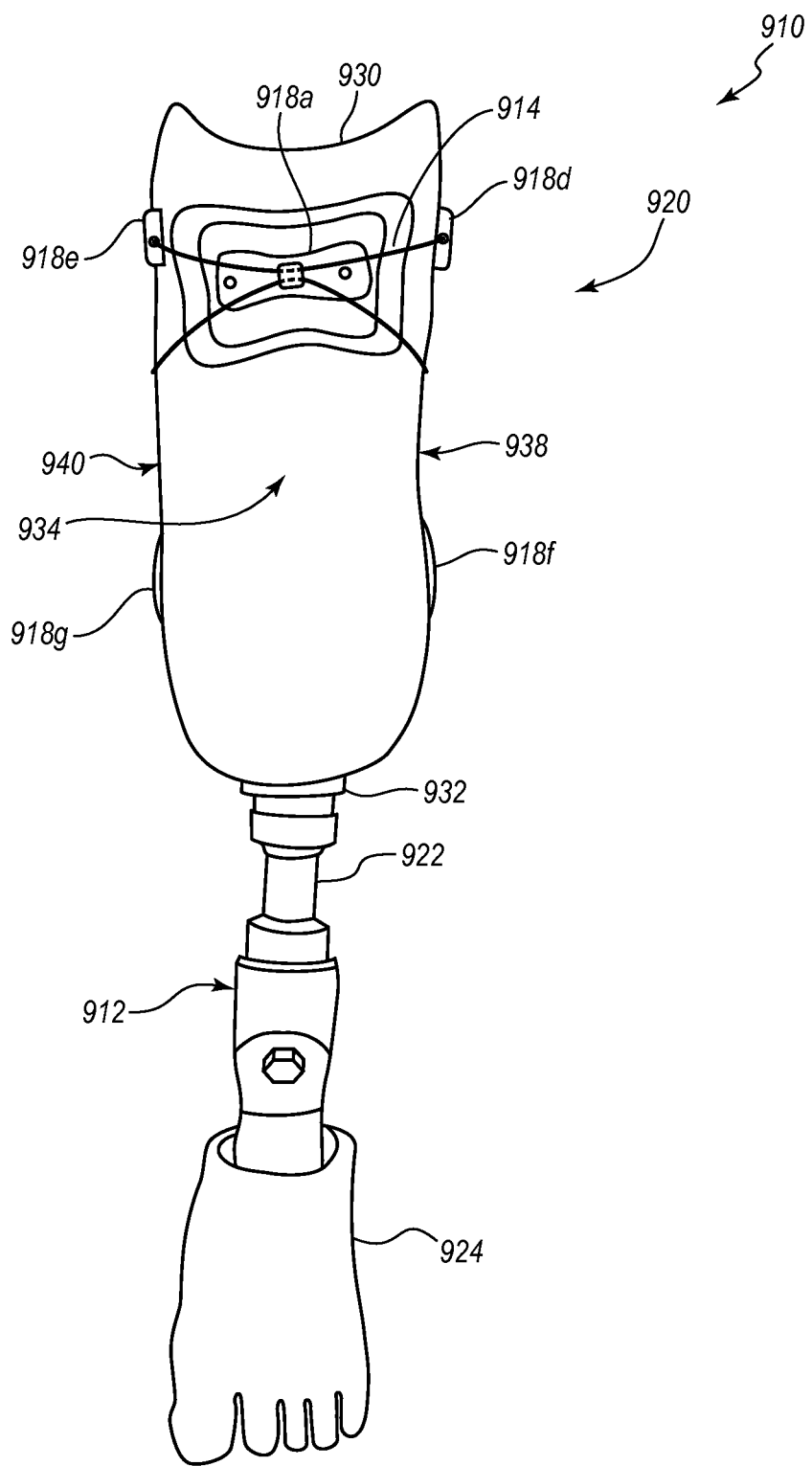
FIG. 19 is a front elevation view of the adjustable prosthetic system of FIG. 18.
Figure 20:
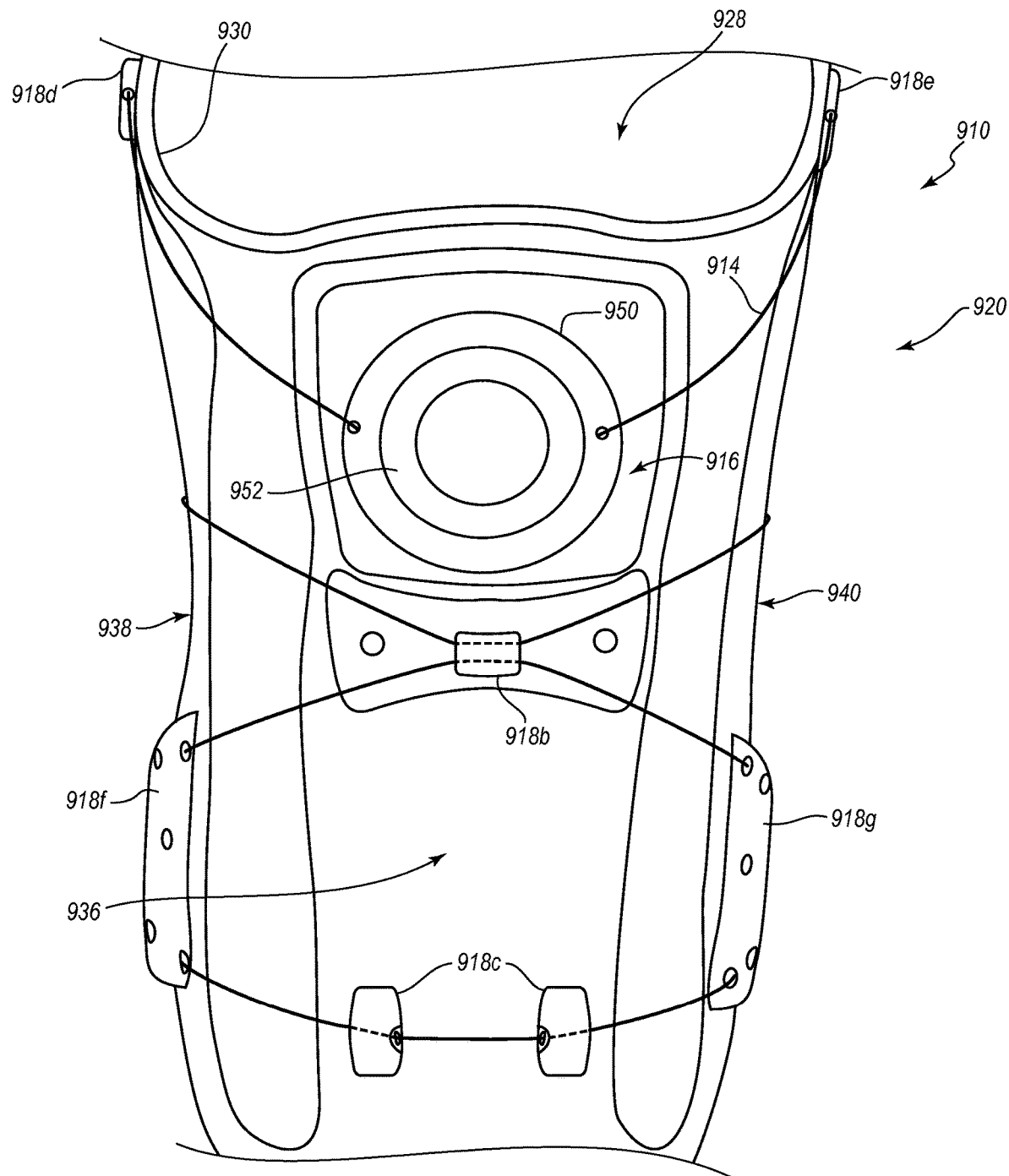
FIG. 20 is an enlarged partial rear elevation view of the adjustable prosthetic system of FIG. 18.
Figure 21:
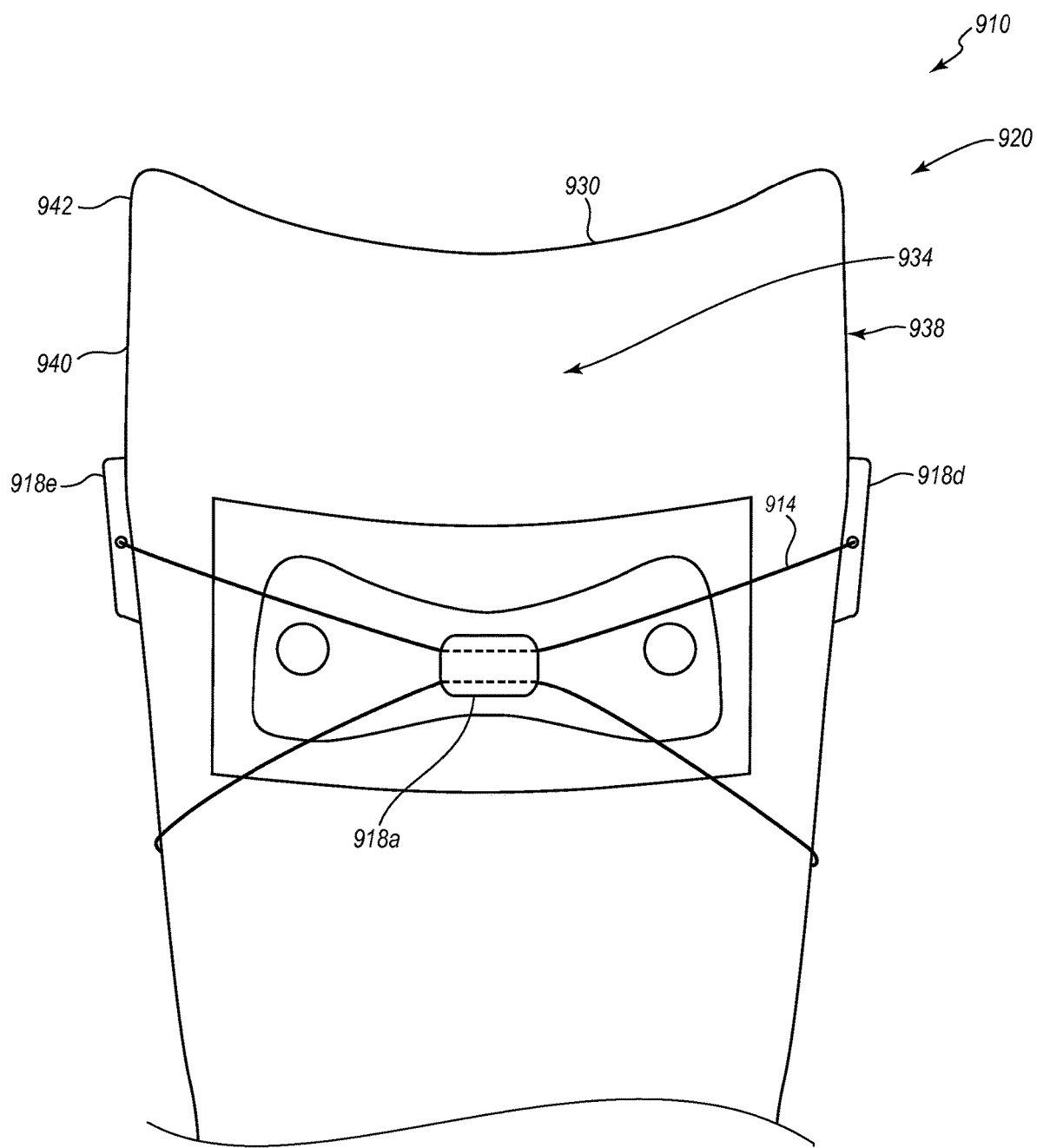
FIG. 21 is an enlarged partial front elevation view of the adjustable prosthetic system of FIG. 18.

In the illustrated embodiment, the anterior portion of the socket 920 may be viewed as a receptacle that is sized to receive at least a portion of a residuum, and the posterior side 936 of the socket 920 may be viewed as a movable panel. As shown in FIG. 18, the anterior and posterior portions of the socket 920 can be integrally attached to each other, and a lower end of the socket 920 thus can act as a hinge about which the posterior portion can rotate relative to the anterior portion.

Figure 24:
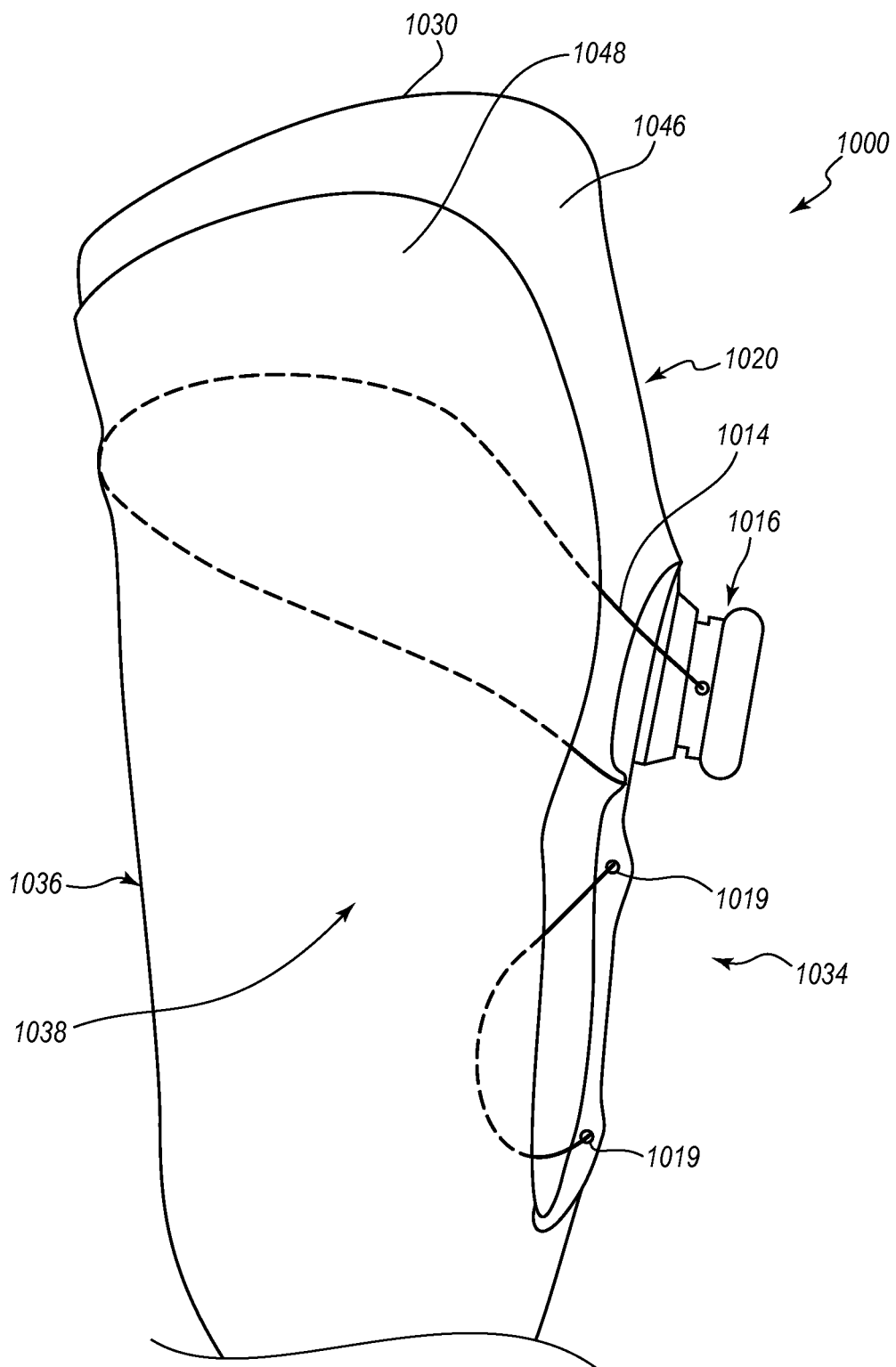
FIG. 24 is a partial left side elevation view of another embodiment of adjustable prosthetic system.
Figure 25:
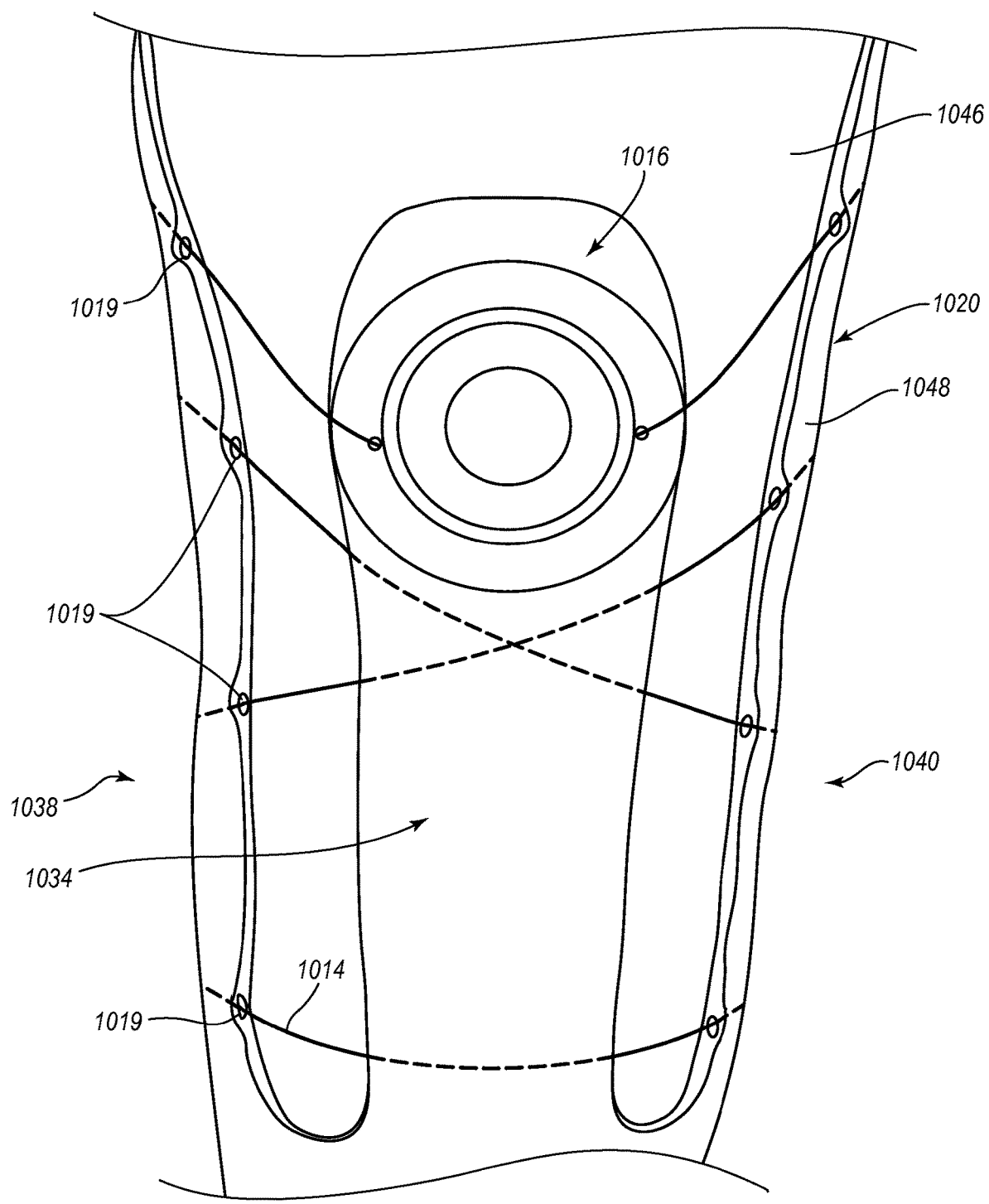
FIG. 25 is a partial rear elevation view of the adjustable prosthetic system of FIG. 24.

Referring now to FIGS. 24 and 25, a prosthetic adjustment system 1000 is shown and described. The prosthetic adjustment system 1000 includes a prosthetic device 1012, a tensioning line 1014, and a tightening mechanism 1016. The prosthetic device 1012 includes a socket 1020 having an upper opening 1030, anterior and posterior portions 1034, 1036, and lateral and medial portions 1038, 1040. The socket 1020 is defined by an inner layer 1046 and an outer layer 1048. The outer layer 1048 may comprise a different material than the inner layer 1046. The outer layer 1048 may extend around only a portion of the periphery of the socket 1020. For example, a portion of the outer layer 1048 may be positioned along the posterior portion 1036, and a gap may be provided between portions of the outer layer 1048 and certain areas at various positions about the periphery of the socket 1020.

In at least one embodiment, a guide path 1019 is defined within the outer layer 1048. Alternatively, the guide path 1019 may be defined between the outer layer 1048 and the inner layer 1046. The guide path 1019 may have a shape similar to that defined by guide members 918a-918g described above, and it can operate in a similar manner thereto. The guide path 1019 may comprise a channel through the material from which the outer layer 1048 is formed. The channel may be defined by the material itself or by another member that is embedded within the material, such as a tube.

The outer layer 1048 may have different physical characteristics than the inner layer 1046, such as, for example, a greater stiffness. The outer layer 1048 may provide additional characteristics that are optimal for certain areas along the socket 1020 to improve performance and/or comfort for the user. The outer layer 1048 may also be referred to as a shell.

Figure 26:
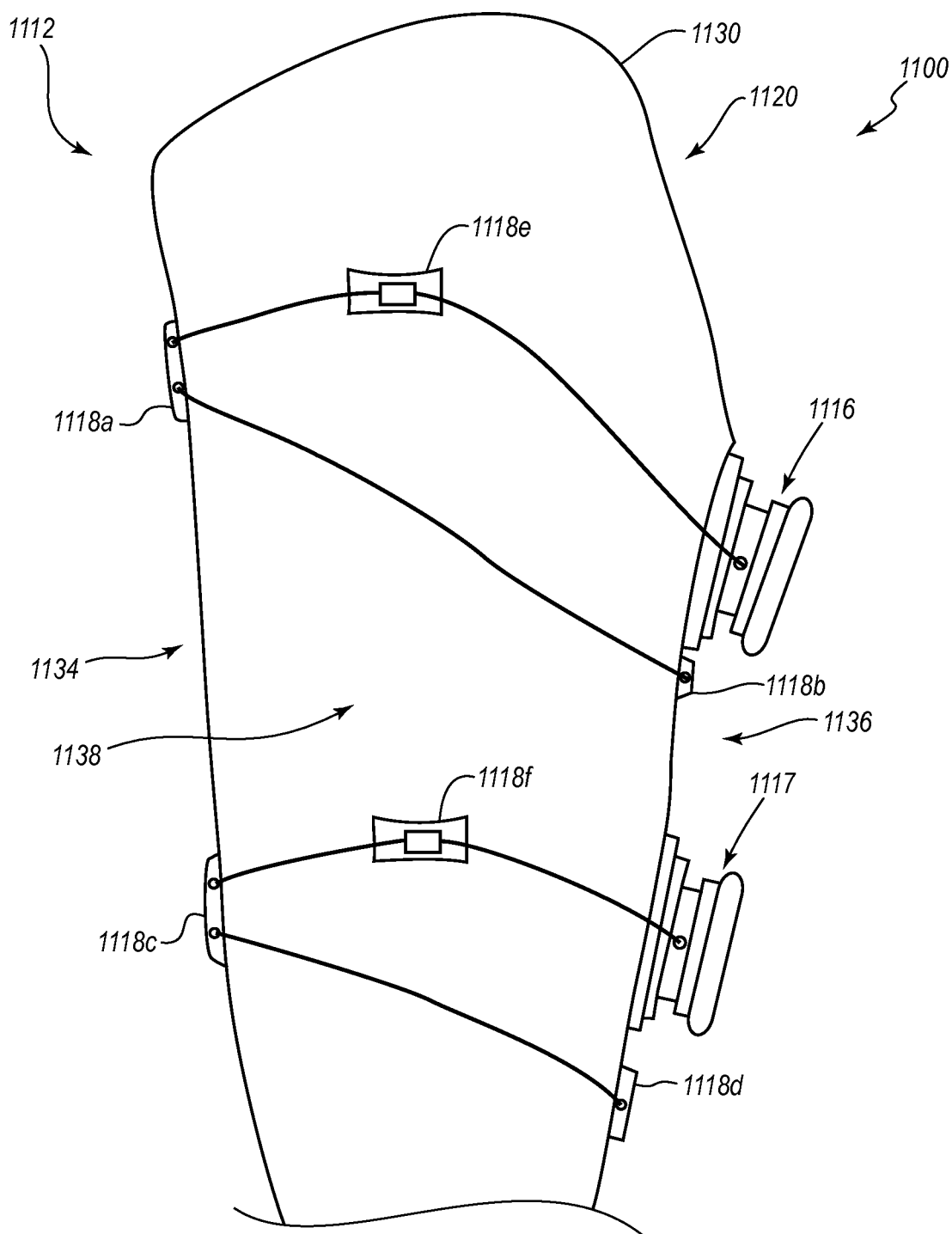
FIG. 26 is a partial left side elevation view of another embodiment of an adjustable prosthetic system.

FIG. 26 illustrates another embodiment of prosthetic adjustment system 1100. The prosthetic adjustment system 1100 includes a plurality of tightening mechanisms 1116, 1117 and tensioning lines 1114, 1115. The tightening mechanism 1116 is positioned vertically above the tightening mechanism 1117 and the tensioning line 1114 is positioned vertically above the tensioning line 1115. In particular, the upper and lower tensioning lines 1114, 1115 define paths that are vertically separated from each other and do not cross. In other examples, at least one of the tensioning lines 1114, 1115 at least partially overlap or bypass each other in the vertical direction. The socket 1120 may include an upper opening 1130 as well as anterior, posterior, lateral and medial portions.

The tightening mechanism 1116 in combination with the tensioning line 1114 and the tightening mechanism 1117 in combination with tensioning line 1115 can each provide a separate compression point or region on a socket 1120. In one example, the compression regions are along a posterior portion 1136 at the location of guide members 1118b, 1118d. More generally, a compression region may include both of the guide members 1118b, 1118d. In other arrangements, compression points may be provided at any of the guide members 1118a-1118f. It is noted that the positions of the guide members 1118a-1118f in the illustrated embodiment are similar to the positions of the guide members 918a-918f described above. In some embodiments, a compression region may have a thinner wall so as to be more flexible than surrounding regions of the socket 1120. In other or further embodiments, the compression region may be comprised of a different material than the surrounding portions of the socket 1120.

Figure 27:
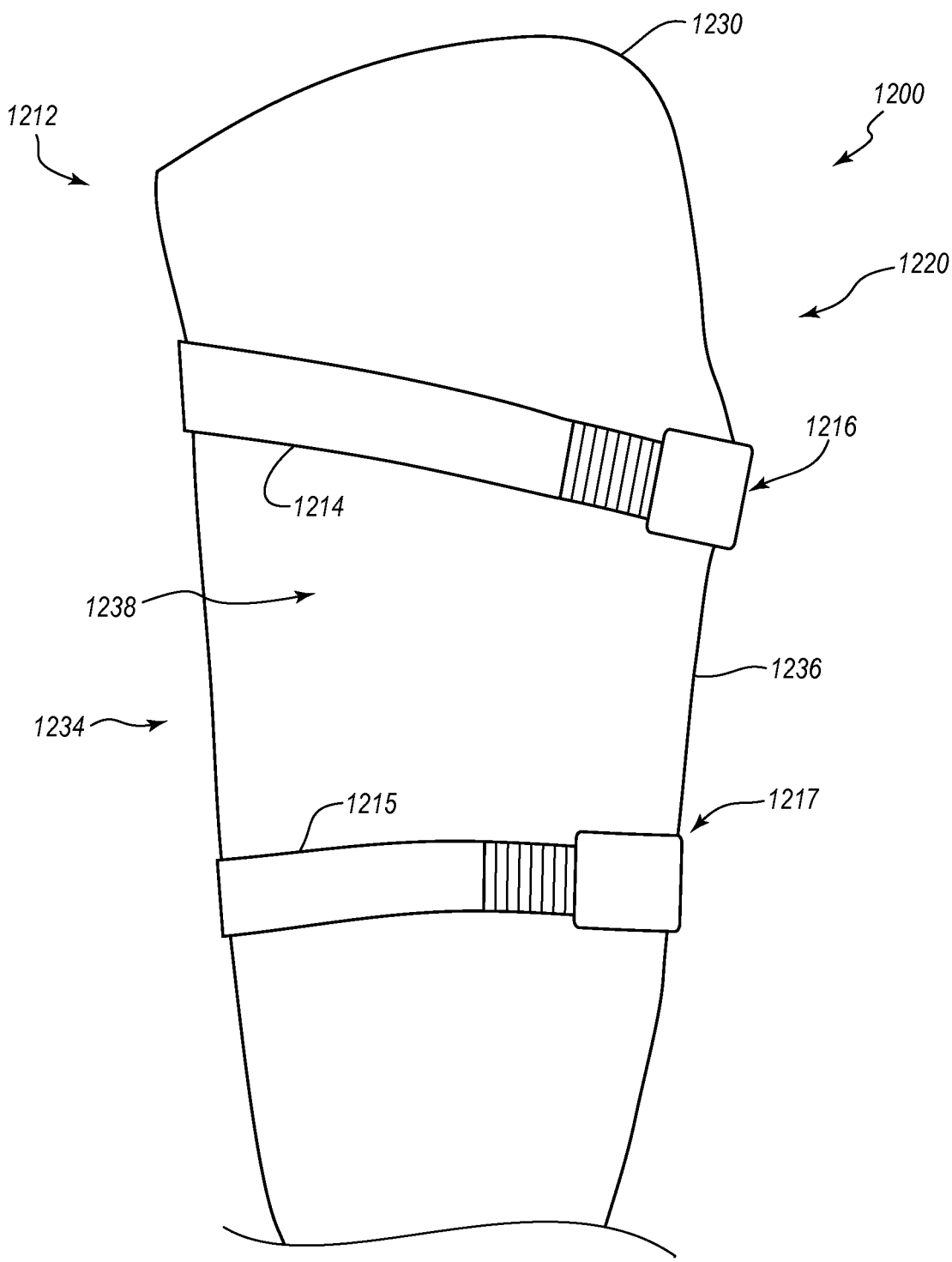
FIG. 27 is a partial left side elevation view of another embodiment of an adjustable prosthetic system.
Figure 28:
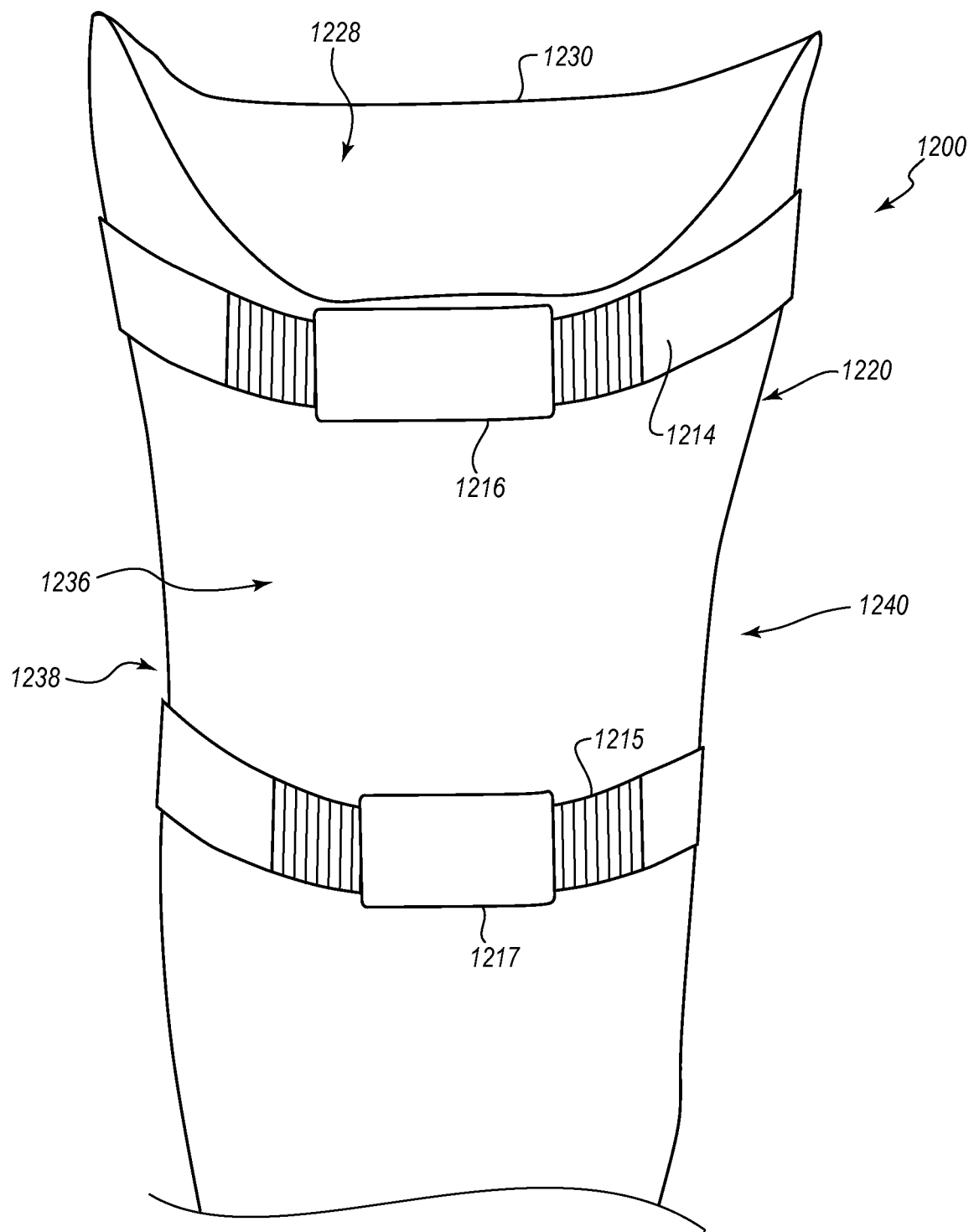
FIG. 28 is a partial rear elevation view of the adjustable prosthetic system of FIG. 27.
Figure 29:
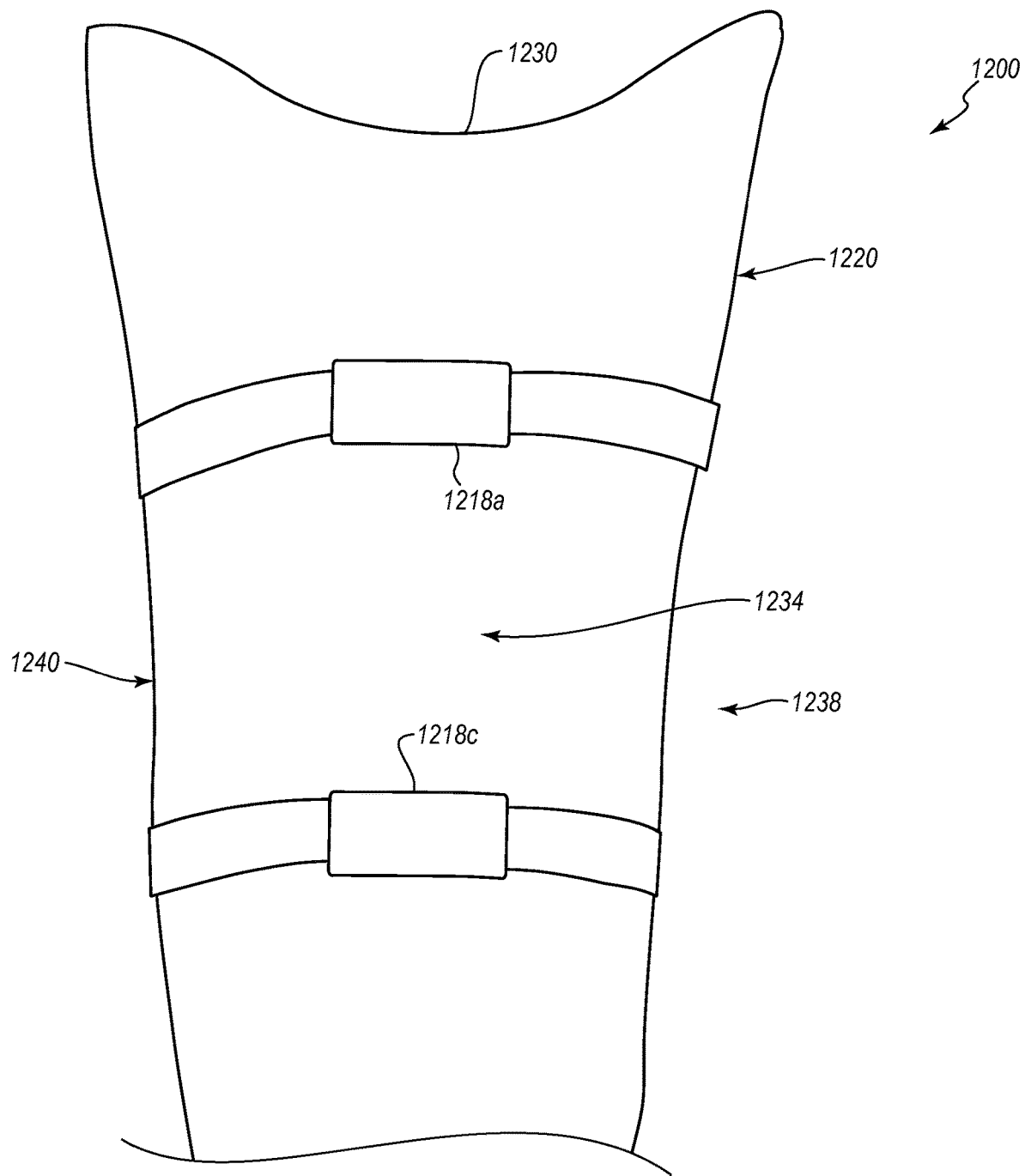
FIG. 29 is a partial front elevation view of the adjustable prosthetic system of FIG. 27.

FIGS. 27-29 illustrate another embodiment of an adjustable prosthetic system 1200. The prosthetic adjustment system 1200 includes a prosthetic device 1212, at least two tensioning lines 1214, 1215 (e.g., lace or strap members), and associated tightening mechanisms 1216, 1217. The prosthetic device 1212 includes a socket 1220 that defines a cavity 1228 that is accessible through an upper opening 1230. The socket 1220 includes anterior, posterior, lateral and medial portions 1234, 1236, 1238, 1240, respectively.

The tightening mechanisms 1216, 1217 are spaced vertically from each other. The tightening mechanisms 1216, 1217, in conjunction with the tensioning lines 1214, 1215, provide application of an adjustment or tightening force to the socket 1220. The tightening mechanisms 1216, 1217 may be a buckle-type mechanism. The buckle mechanism may be operable between a released position and a locked position. When in the released position the tensioning lines 1214, 1215 are able to move relative to the tightening mechanisms 1216, 1217, and when in the locked position the tensioning lines 1214, 1215 are in a fixed position. The tightening mechanisms 1216, 1217 may comprise a cam-type or lever-type member that apply a tension force in the tensioning lines 1214, 1215 when the tightening mechanisms are activated between the released and locked states.

In the embodiment shown in FIGS. 27-29, the tensioning lines 1214, 1215 extend fully about a periphery of the socket 1220, and thus may be configured to generally apply compressive pressure about the full periphery of the socket 1220. In other embodiments, the tensioning lines 1214, 1215 can pass through guides such as those discussed above, and the guides may be sized, positioned, or otherwise configured so as to apply pressure only at desired positions about the periphery of the socket 1220.

In other embodiments, the tensioning lines 1214, 1215 can extend about the full periphery of the socket 1220, as shown. However, rather than defining a substantially continuous periphery, such as that shown in FIGS. 27-29, the socket 1220 may have gaps that can be narrowed or closed upon application of the pressure. Such an arrangement can be similar to that depicted in FIGS. 18-21. In still other embodiments, the socket 1220 may have pressure members or panels that can extend outwardly relative to neighboring portions of the socket 1220. Such an arrangement can resemble that of the panels 122c, 122d in FIG. 1. A tensioning line 1215 can encircle the panels 122c, 122d. When the panels 122c, 122d are pushed outwardly due to the presence of a residuum within the socket 1220, the tensioning line 1215 can define a peripheral length. Tightening tensioning line 1215 via the tightening mechanism 1217 can reduce the peripheral length of the tensioning line 1215, which can force the panels 122c, 122d about which it extends to simultaneously be moved inwardly.

In still other embodiments, the tensioning lines 1214, 1215 and tightening mechanisms 1216, 1217 can be more localized. For example, where the socket 1220 includes panels 122c, 122d, such as those shown in FIG. 1, the tensioning line 1214 and tightening mechanism 1216 can be associated only with the panel 122c, and the tensioning line 1215 and tightening mechanism 1217 can be associated only with the panel 122d. Specifically, the tensioning line 1214 may be anchored to the socket 1220 at a position that is left of the panel 122c, can extend about an outer surface of the panel 122c, and can be connected to the tightening mechanism 1216 at a position that is right of the panel 122c. Similarly, the tensioning line 1215 may be anchored to the socket 1220 at a position that is to the right of the tightening mechanism 1216 and that is left of the panel 122d, can extend about an outer surface of the panel 122d, and can be connected to the tightening mechanism 1217 at a position that is right of the panel 122d. When the panels 122c, 122d extend outwardly from the portions of the socket 1220 that neighbor each panel, tightening of the tensioning lines 1214,1215 can force the panels 122c, 122d inwardly toward an interior of the socket 1220. The tensioning lines 1214, 1215 can be adjusted separately, or individually so as to move the panels 122c, 122d by different amounts, if desired.

The tightening mechanisms 1216, 1217 (as well as the other tightening mechanisms disclosed herein), which also may be referred to as locking mechanisms, may include any suitable tightening, locking, and/or securing mechanisms, such as any of those discussed above. The illustrated embodiment shows tightening or locking mechanisms such as buckles, latches, snaps, hook and loop fasteners, or the like. Further suitable tightening mechanisms are disclosed in U.S. Patent Application Publication No. 2008/0066272, which is incorporated herein in its entirety by this reference. U.S. Pat. No. 7,431,738 discloses additional adjustable buckles, latches, and associated strap members that can be used as the tightening mechanisms and tensioning lines disclosed herein. U.S. Pat. No. 7,431,738 is also incorporated herein in its entirety by this reference. Additional examples of suitable devices and systems include various embodiments of a cam assembly that advances or retracts a strap (e.g., a tensioning line), such as disclosed in U.S. Patent Application Publication No. 2009/0184189, which is incorporated herein in its entirety by this reference. Suitable tightening mechanisms are also disclosed in U.S. Pat. No. 7,293,373 and U.S. Patent Application Publication No. 2010/0139057, each of which is also incorporated herein in its entirety by this reference. The tightening mechanisms can include ratcheting systems such as discussed above, as well as those disclosed in U.S. Pat. No. 6,289,588, the entire contents of which are hereby incorporated by reference herein. Many other incremental tightening mechanisms having dialing and/or incremental tightening systems are available from Boa Technology of Denver, Colo. Where the tightening mechanism includes an actuator (e.g., the actuator 170 of the tightening mechanism 108), the actuator can comprise any suitable actuation interface, such as a knob, lever, button, etc. In various embodiments, the actuator can be actuated in any suitable manner, such as, for example, by any suitable movement (e.g., rotation, pushing, pulling, or sliding). It is also noted that the term "tightening" as used herein with respect to the tightening mechanism can refer to the development of increased tension in a tensioning line and/or a constriction or reduction of a perimeter defined by the tensioning line such that the tensioning line defines a tighter perimeter. The tightening mechanism may also be referred to as an adjustment mechanism.

In various embodiments disclosed herein, adjustment of the tightening mechanism may change an internal size or shape of the cavity of the prosthetic socket. In some embodiments, the adjustment of the size or shape of the internal cavity of the socket may be changed along only a portion of the socket rather than along an entire length of the socket.

Certain tensioning lines disclosed herein may be constructed as an elongate member having any desired cross-sectional shape, such as, for example, circular, oval, rectangular or triangular cross-sectional shape. The tensioning lines may be constructed as a strap member having a greater width than thickness. The tensioning lines may comprise any desired construction or feature that enhances operability and interface with the tightening mechanism. For example, at least a portion of the tensioning line may include a plurality of holes, grooves, protrusions and may have varying widths and thicknesses. In at least some of the embodiments disclosed herein, a single tensioning line may be used with a plurality of tightening mechanisms. Further, a single tightening mechanism can be used with a plurality of tensioning lines. A tensioning line may extend along a guide path, wherein the guide path is defined along any portion of the prosthetic socket. Further, the tightening mechanism can be positioned at any location on the socket, and in some instances in other locations on a prosthetic device, such as at a support pylon (e.g. the pylon 922 in FIG. 18).

FIGS. 30-34 illustrate another embodiment of an adjustable prosthetic system 1300. The prosthetic adjustment system 1300 includes a prosthetic device 1312, a pair of tensioning lines 1314, 1315, and a pair of tightening mechanisms 1316, 1317 associated with the tensioning lines 1314, 1315, respectively. The prosthetic adjustment system 1300 further includes a plurality of tensioning pads 1318a-1318h. The tensioning pads 1318a-1318h are arranged to apply a compressive force against a user's limb when tension is applied to the tensioning lines 1314, 1315 by the tightening mechanisms 1316, 1317. The tensioning pads 1318a-1318h can resemble the panels described above (e.g., the panels 122a-122f), and may also be referred to as compression members or pressure members.

The prosthetic device 1312 includes a socket 1320 that defines a cavity 1328 having an upper opening 1330. The socket 1320 also includes anterior and posterior portions 1334, 1336, and lateral and medial portions 1338, 1340. Socket 1320 also includes an inner layer or liner 1346 and an outer layer or shell 1348.

Figure 30:
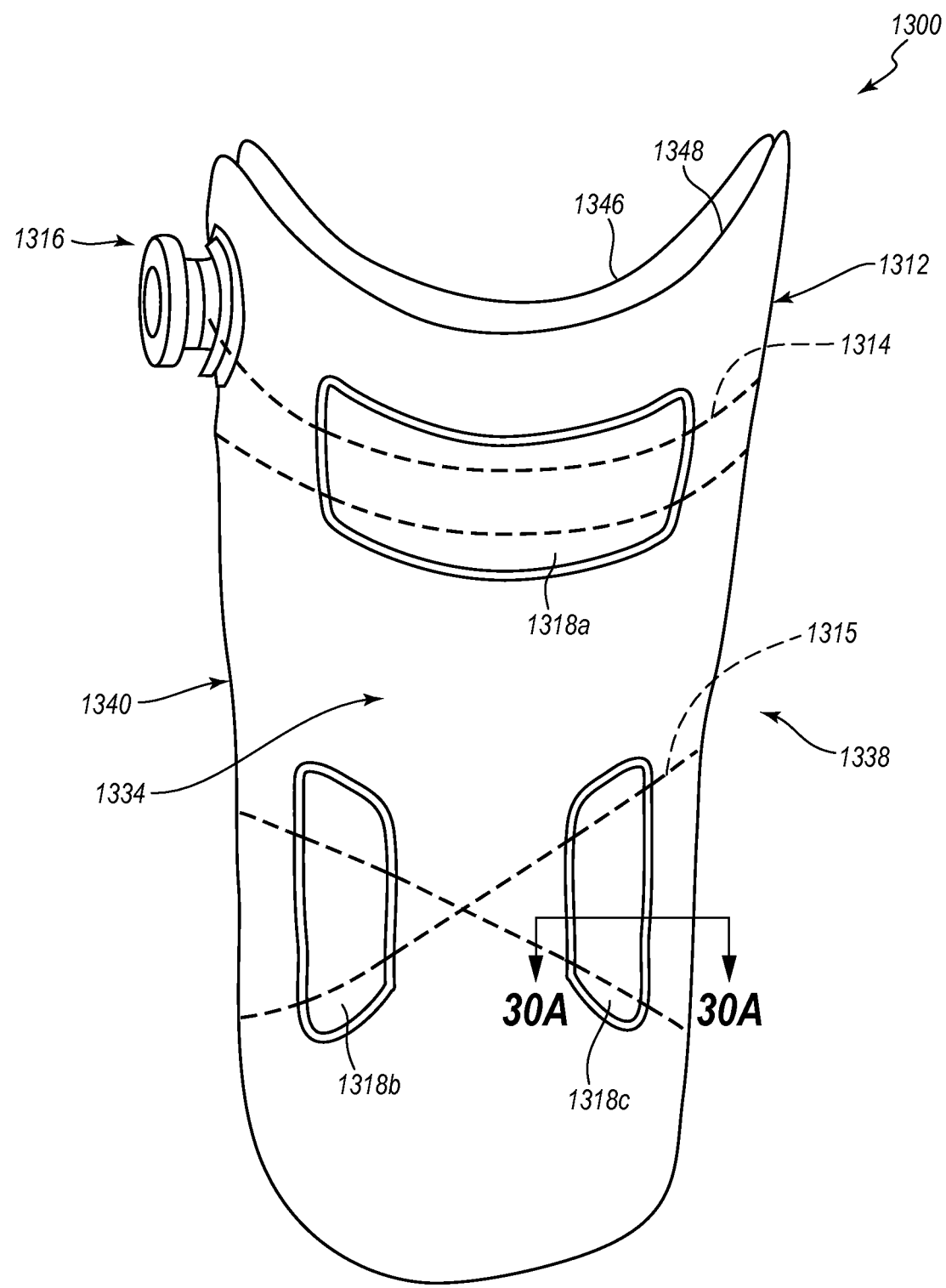
FIG. 30 is a front elevation view of another embodiment of an adjustable prosthetic system.
Figure 30A:
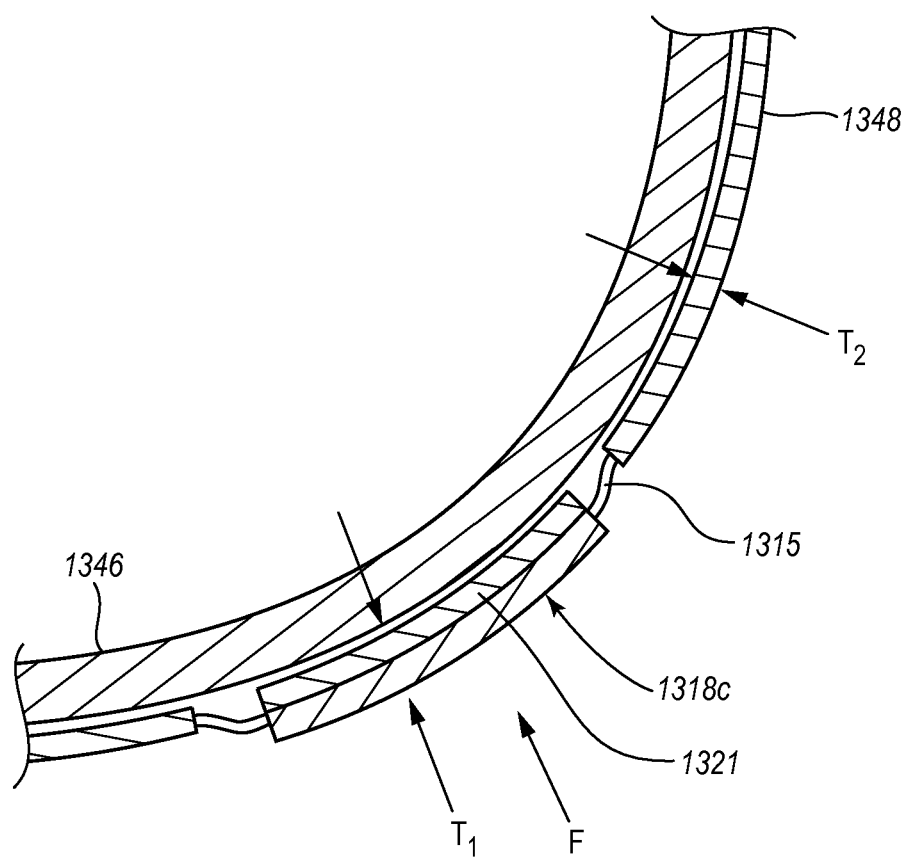
FIG. 30A is a cross-sectional view of a portion of the adjustable prosthetic system of FIG. 30.
Figure 31:
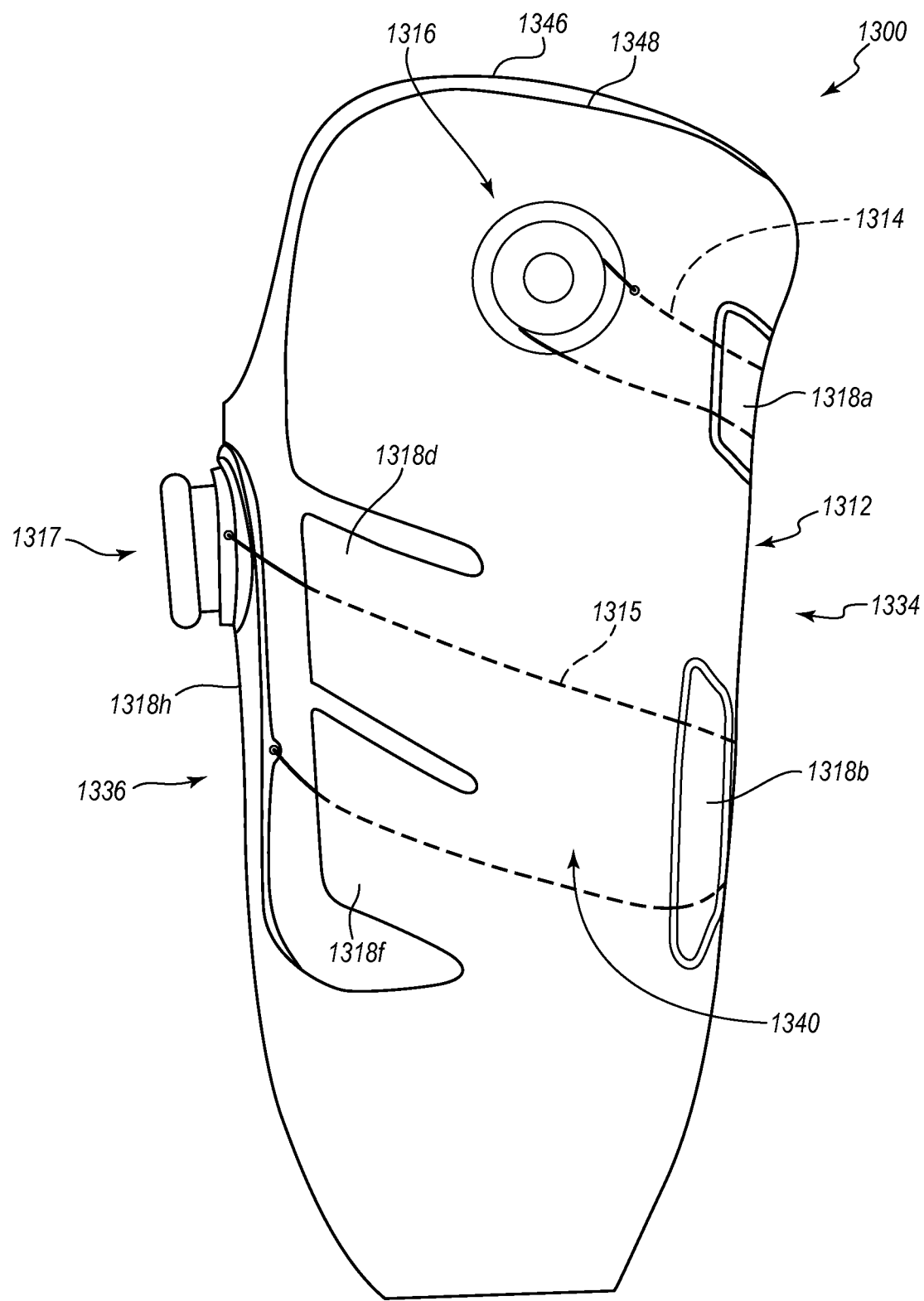
FIG. 31 is a right side elevation view of the adjustable prosthetic system of FIG. 30.
Figure 32:
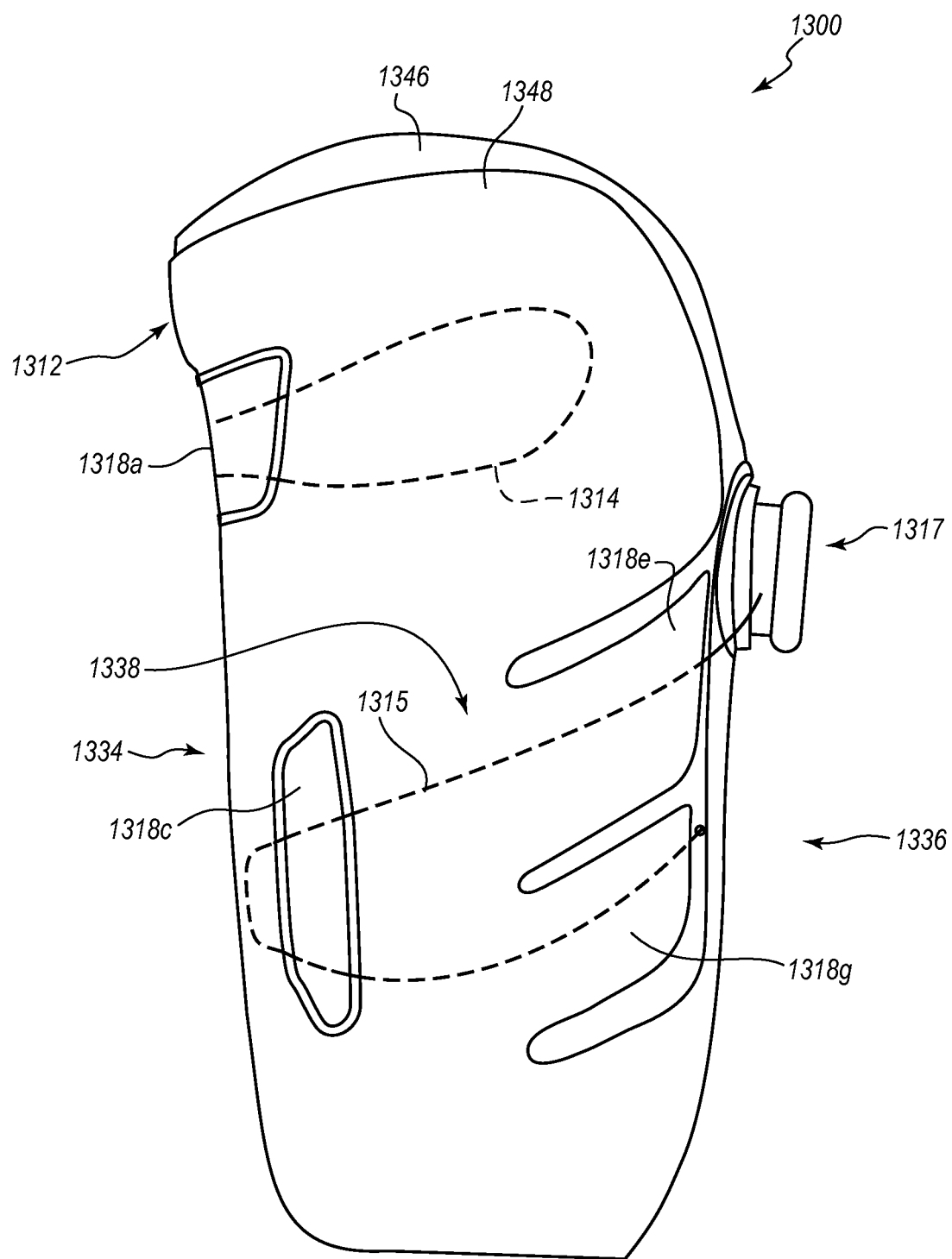
FIG. 32 is a left side elevation view of the adjustable prosthetic system of FIG. 30.
Figure 33:
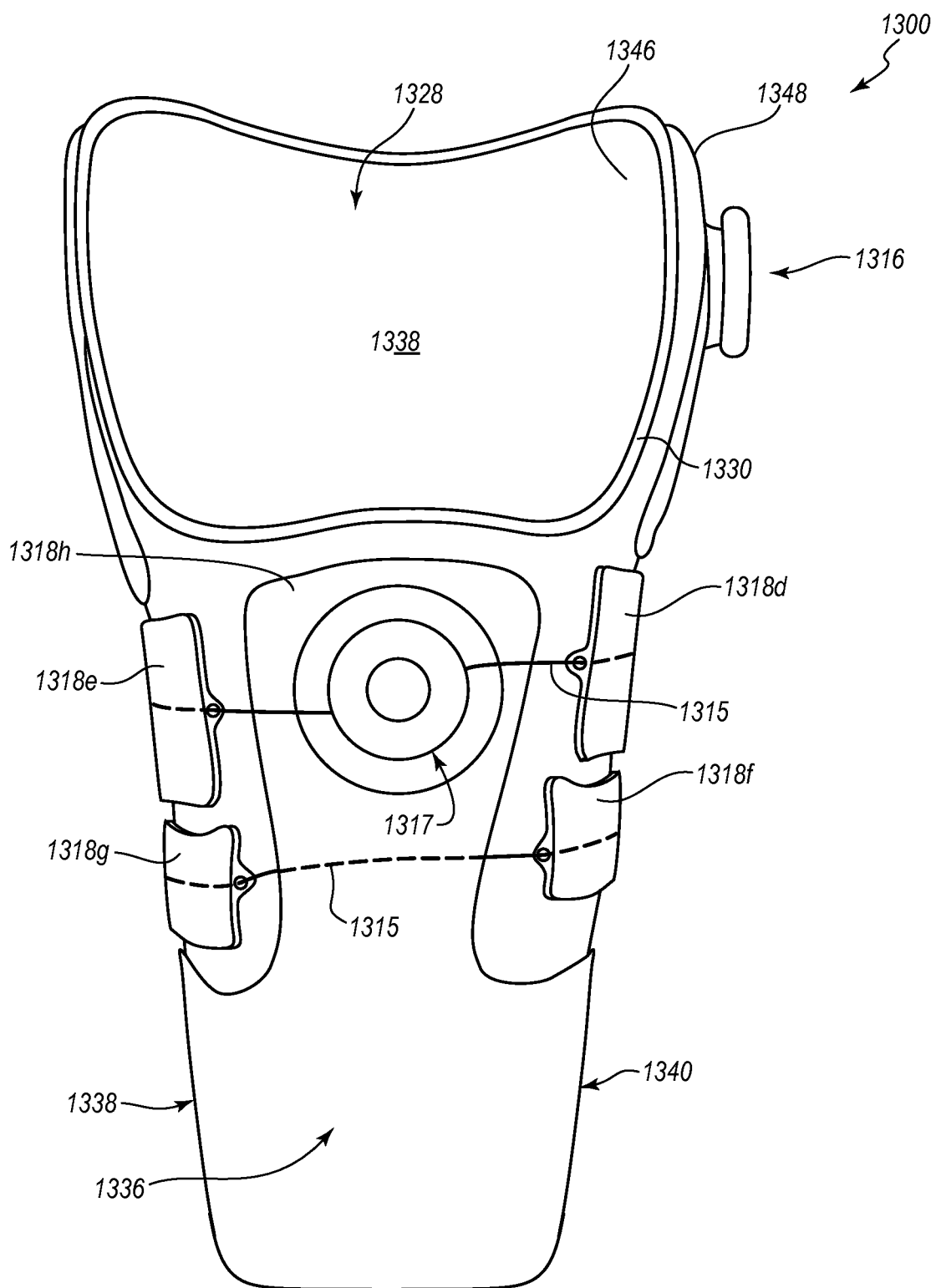
FIG. 33 is a rear elevation view of the adjustable prosthetic system of FIG. 30.
Figure 34:
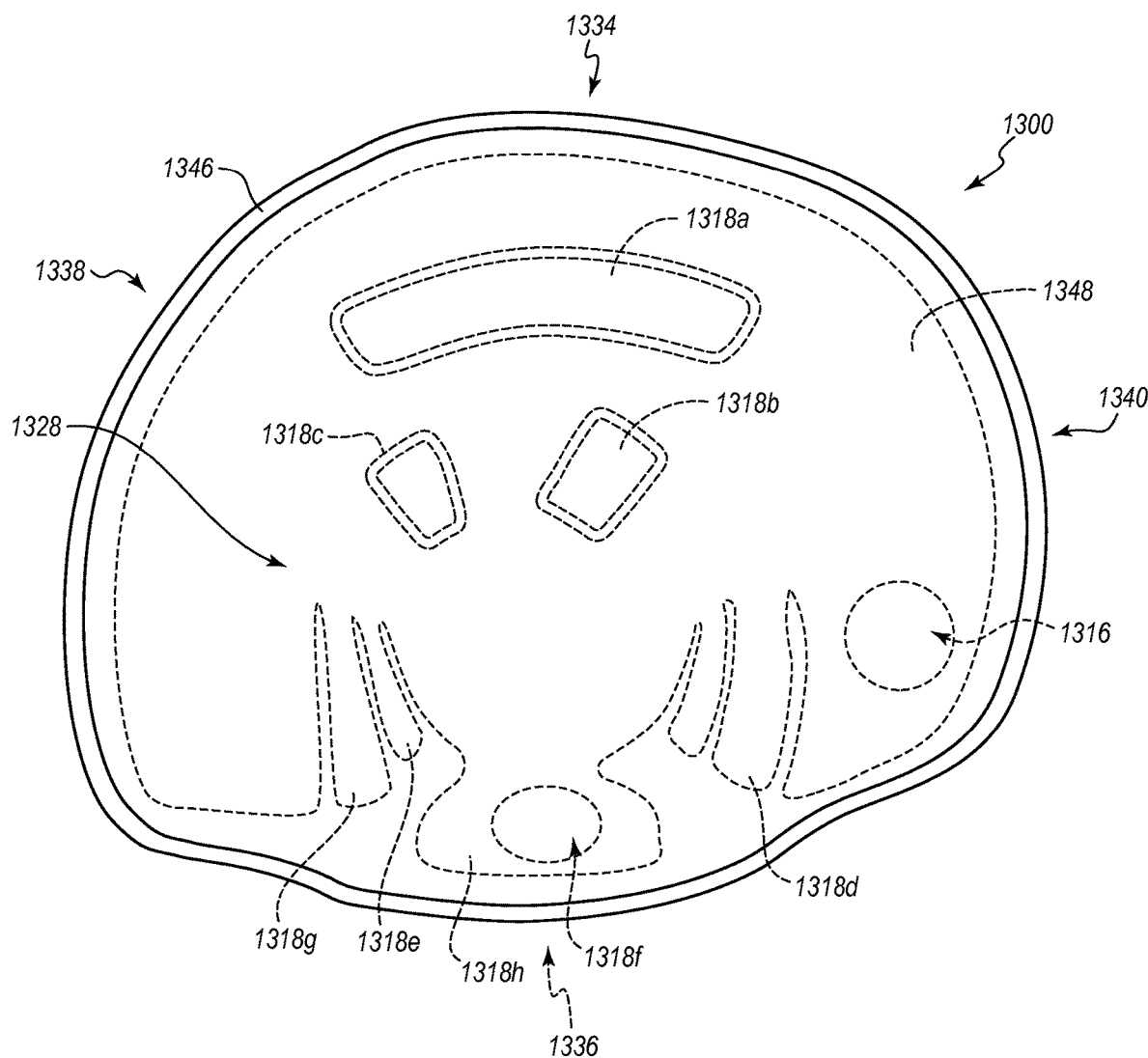
FIG. 34 is a top plan view of the adjustable prosthetic system of FIG. 30.

With reference to FIG. 30A, the shell 1348 can have a general thickness T2. A padding layer 1321 may be connected or coupled to the shell portion of the tensioning pads 1318a-1318h that causes the pads to have a total thickness T1, which can be greater than the thickness T2 of the surrounding region of the shell 1348. Consequently, the tensioning pads 1318a-1318h can be forced outwardly relative to the socket 1320 when a residuum is positioned therein. Applying a tension force in a tensioning lines 1314, 1315 urges the tensioning pads 1318a-1318h radially inward to apply a force F to the user's limb in the area of the tensioning pads 1318a-1318h.

In the illustrated embodiment, the padding layer 1321 is provided between the shall 1348 and the liner 1346 such that the liner is continuous in the region of the pads 1318a-1318h. In other or further embodiments, a padding layer 1321 may be applied to an inner and/or outer surface of the liner 1346, which can similarly force the shell portion of the tensioning pads 1318a-1318h outwardly when a residuum is within the socket 1320.

A tensioning pad 1318 may be completely disconnected from the outer shell 1348, as shown, for example, by the tensioning pads 1318a-1318c in FIG. 30. In other instances, at least a portion of a tensioning pad 1318 may be connected to or be integral with at least a portion of the outer shell 1348, as shown, for example, by the tensioning pads 1318d-1818h in FIGS. 31-33. Typically, at least a portion of each tensioning pad 1318a-1318h is moveable relative to the remaining portions of the outer shell 1348 in a radial direction.

The tensioning pads 1318a-1318h may be arranged at any location around the periphery on the prosthetic 1312 and have any shape, size, or number of placements to provide the desired application of force to the user's limb. The size and shape as well as the orientation of each of each of the tensioning pads 1318a-1318h relative to the user's limb may serve a different purpose in providing the particular amount and direction of force at the interface of a given anatomical feature.

Figure 35:
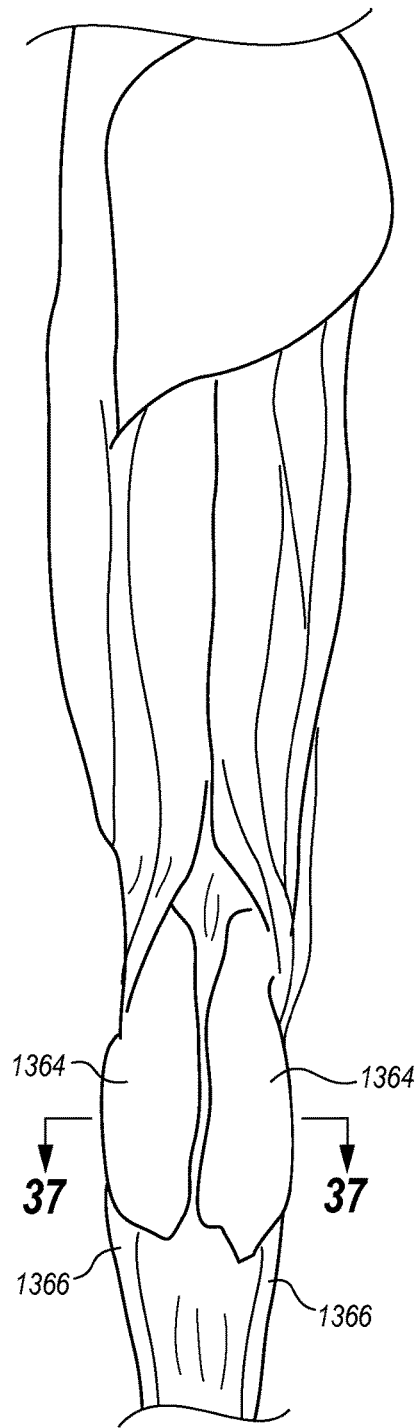
FIG. 35 is a rear elevation view of the anatomy of a human left leg.
Figure 36:
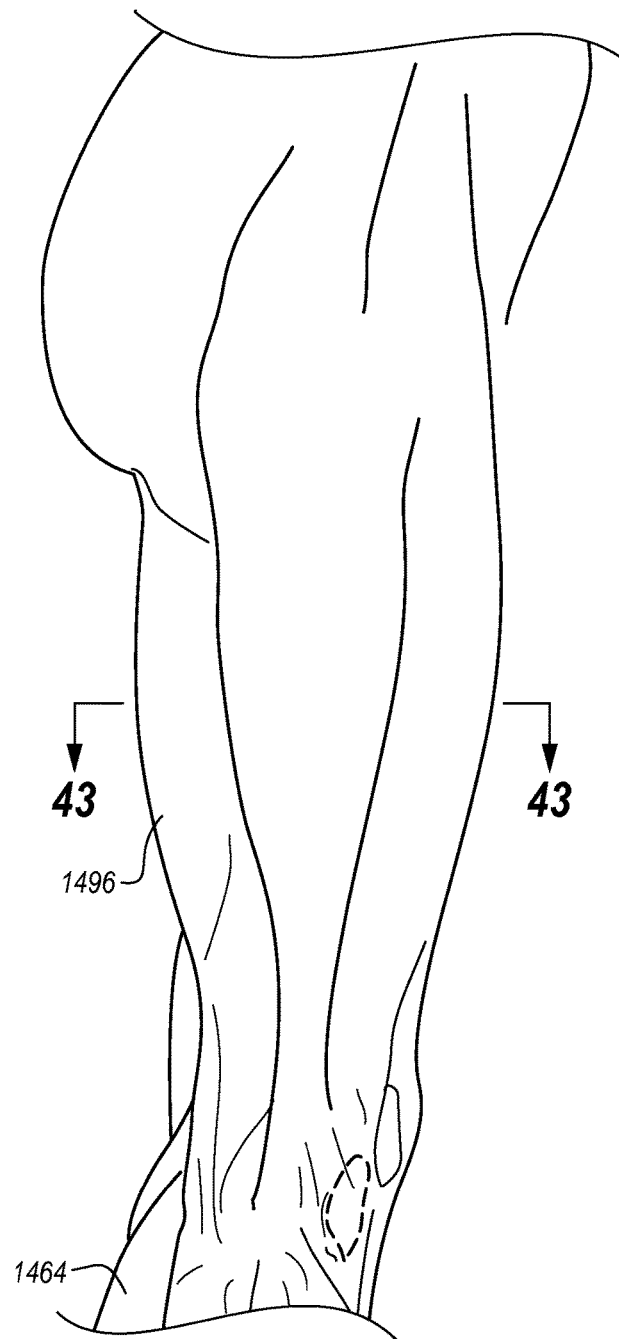
FIG. 36 is a right side elevation view of the anatomy of a human right leg.
Figure 37:
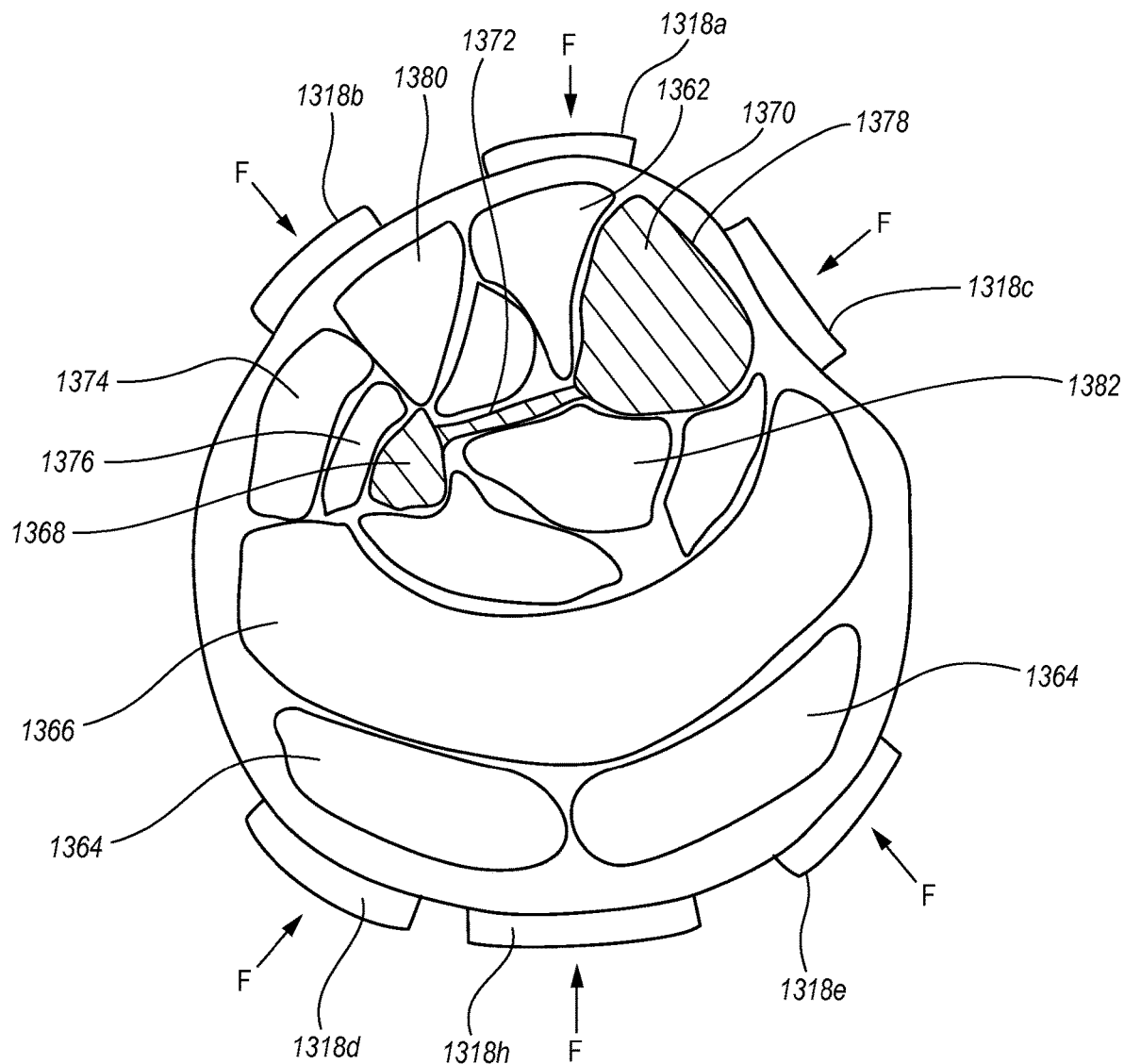
FIG. 37 is a schematic cross-sectional view of the human leg taken along the view line 37-37 in FIG. 35 and illustrating directions in which forces are applied by the adjustable prosthetic system of FIG. 30.
Figure 38:
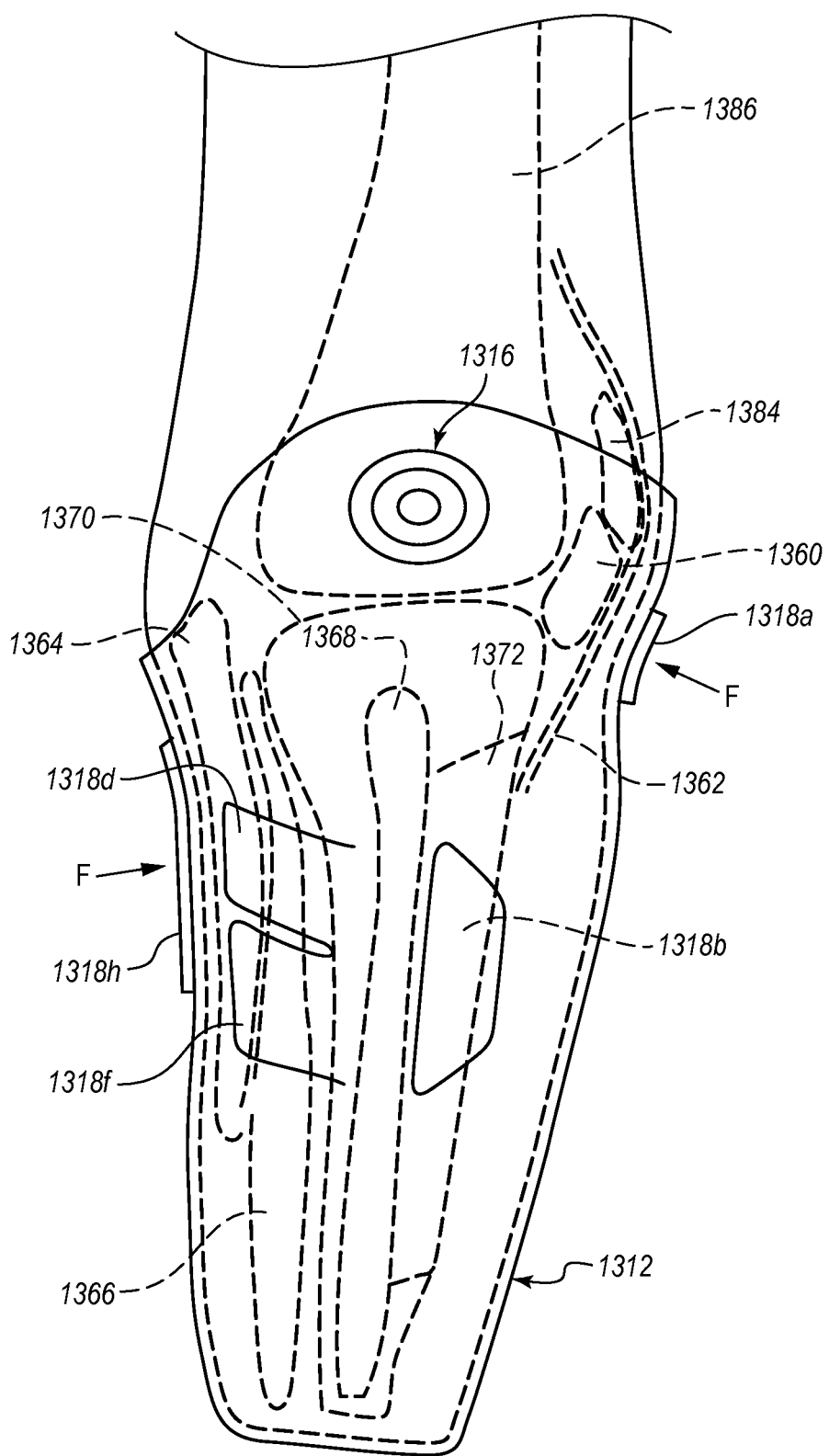
FIG. 38 is a schematic side elevation view of a residuum of a human leg within the adjustable prosthetic system of FIG. 30.
Figure 39:
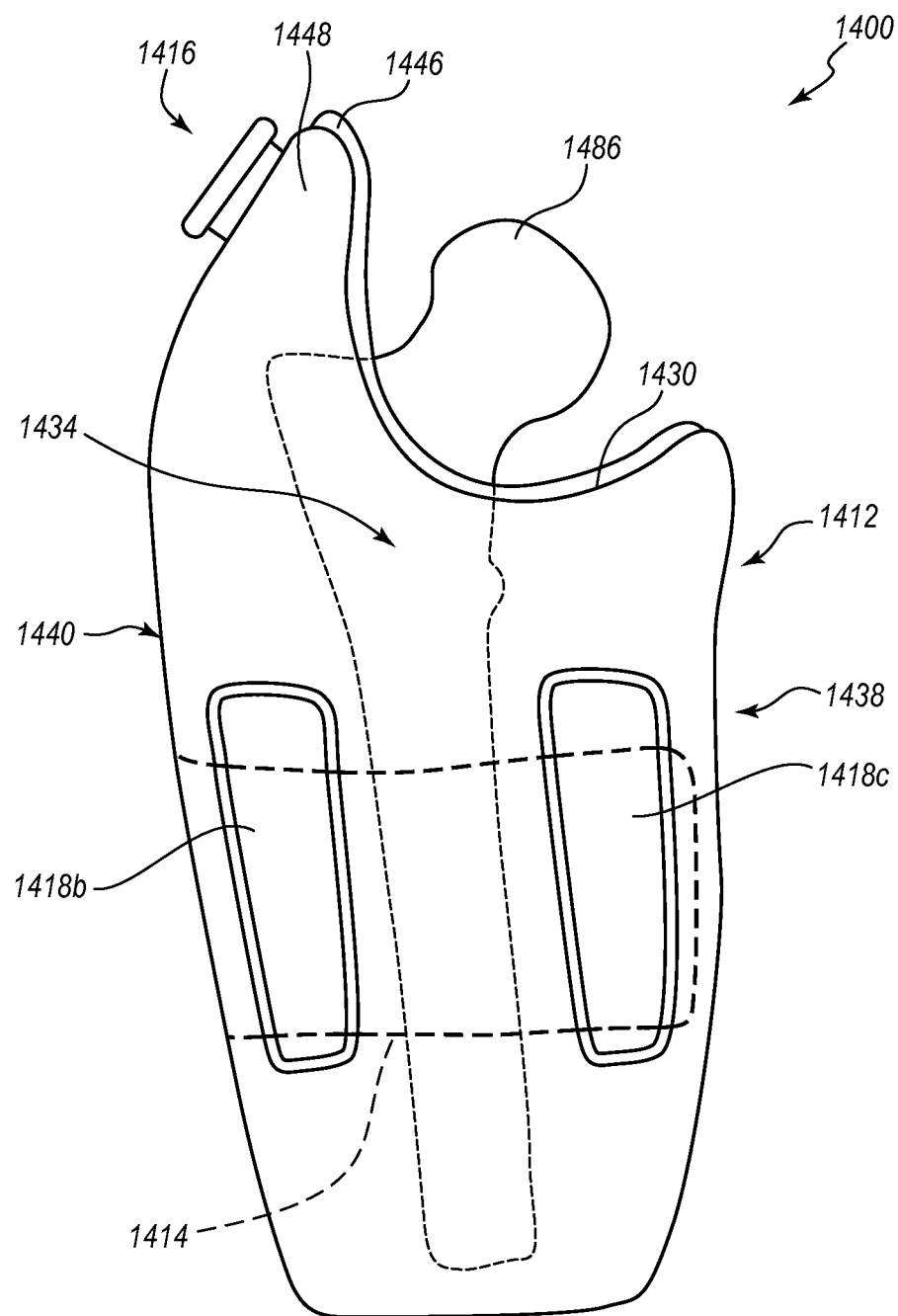
FIG. 39 is a front elevation view of another embodiment of an adjustable prosthetic system schematically showing an intended position of a portion of a femur therein.
Figure 40:
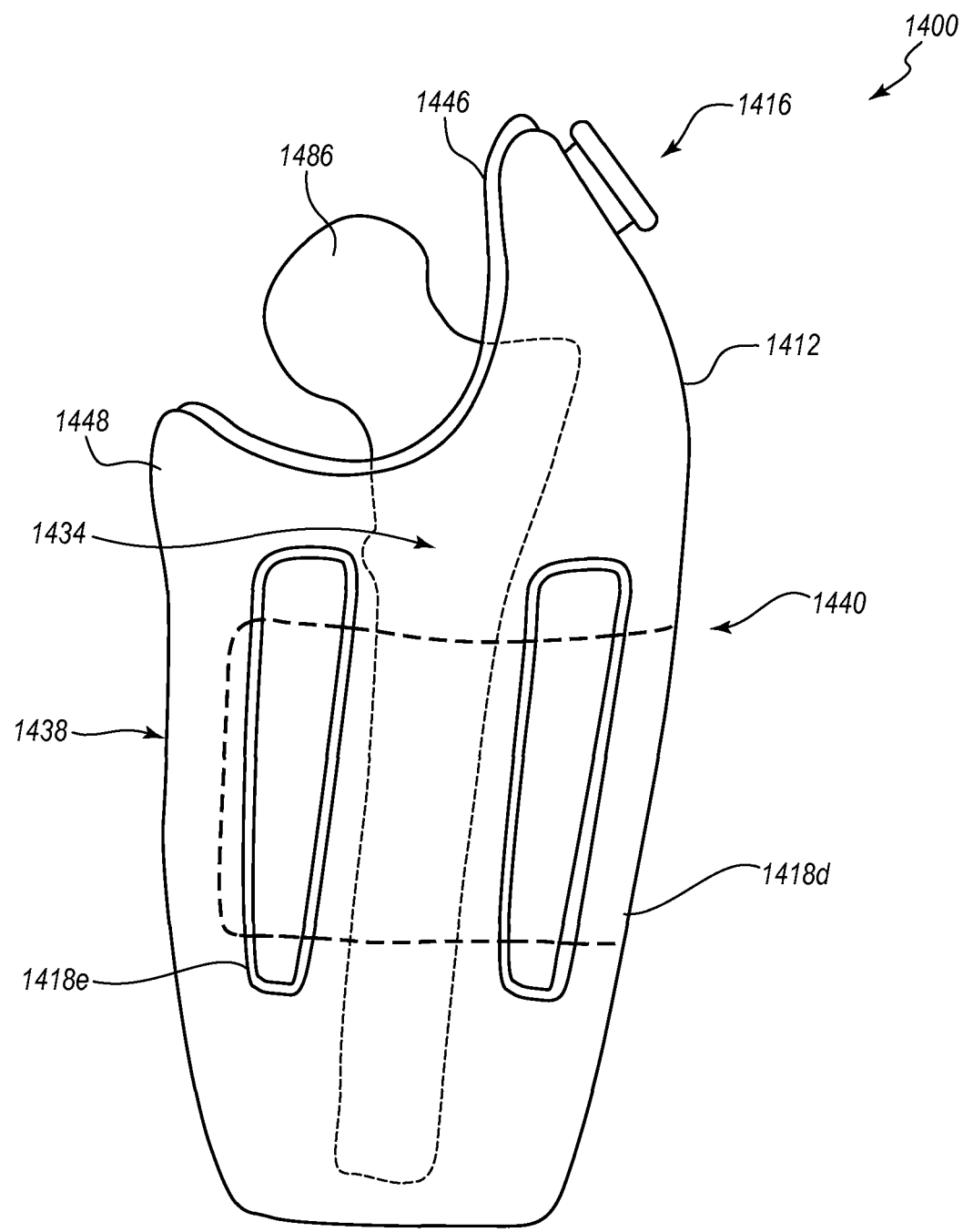
FIG. 40 is a rear elevation view of the adjustable prosthetic system of FIG. 40.
Figure 41:
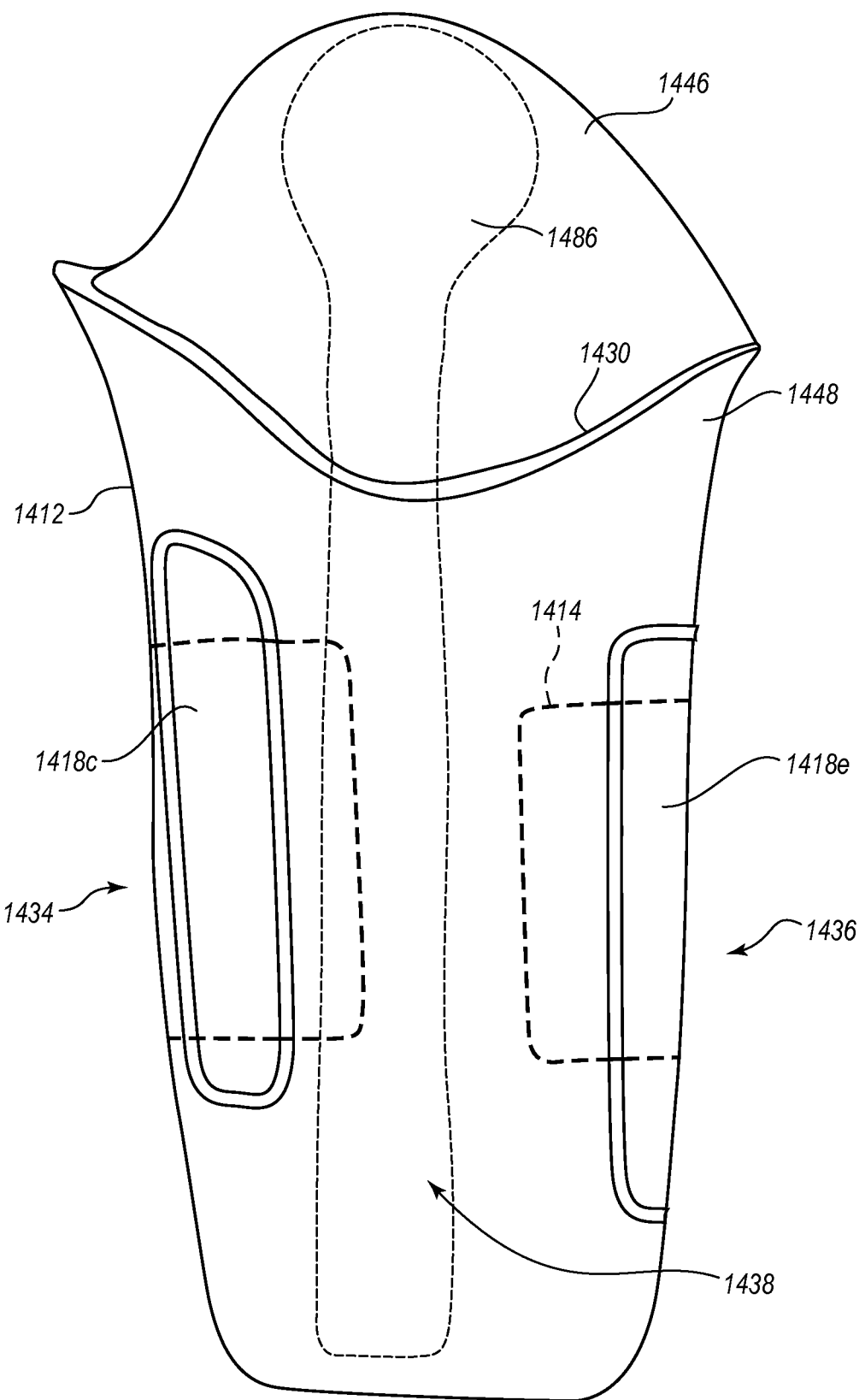
FIG. 41 is a right side elevation view of the adjustable prosthetic system of FIG. 40.
Figure 42:
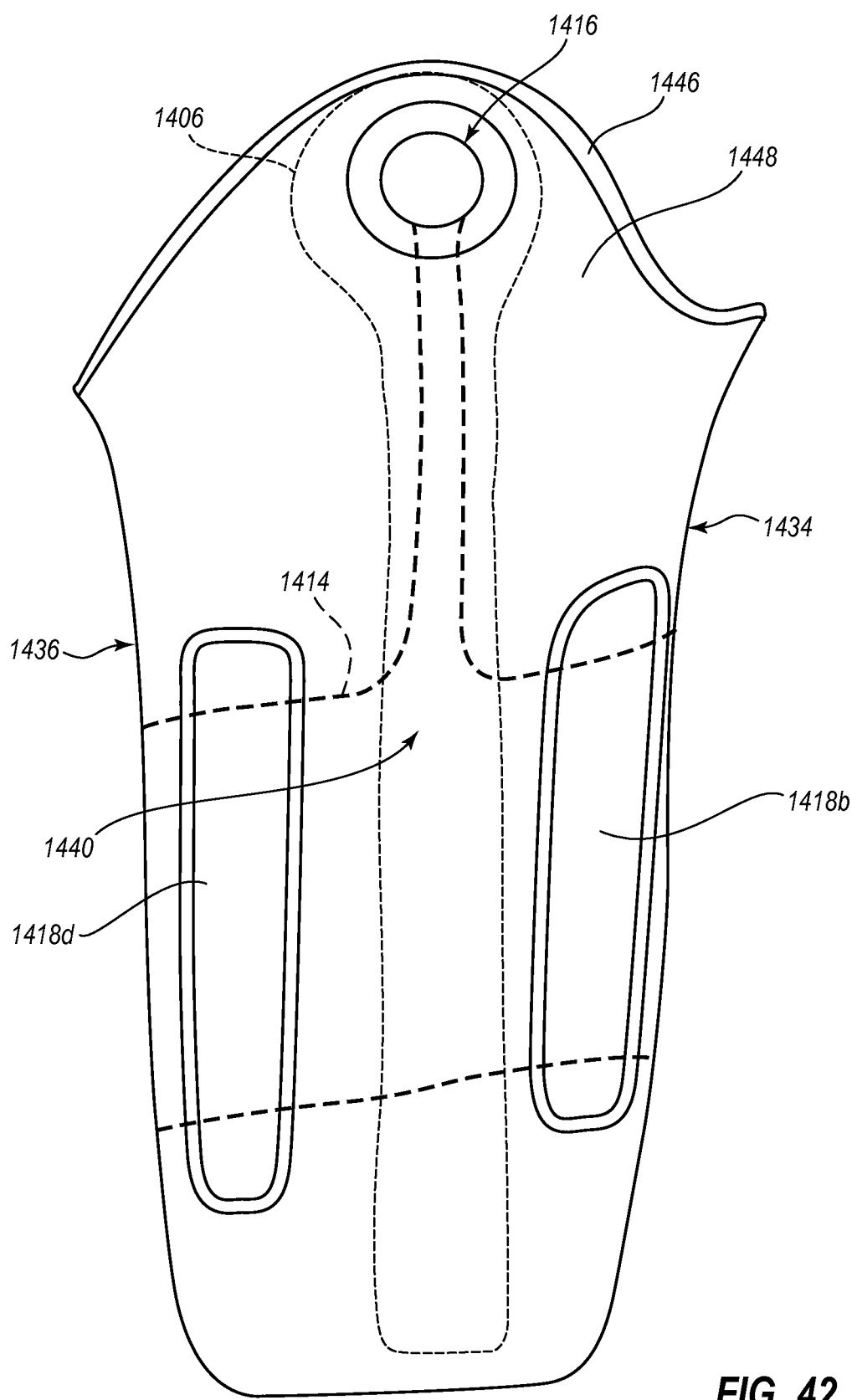
FIG. 42 is a left side elevation view of the adjustable prosthetic system of FIG. 40.
Figure 43:
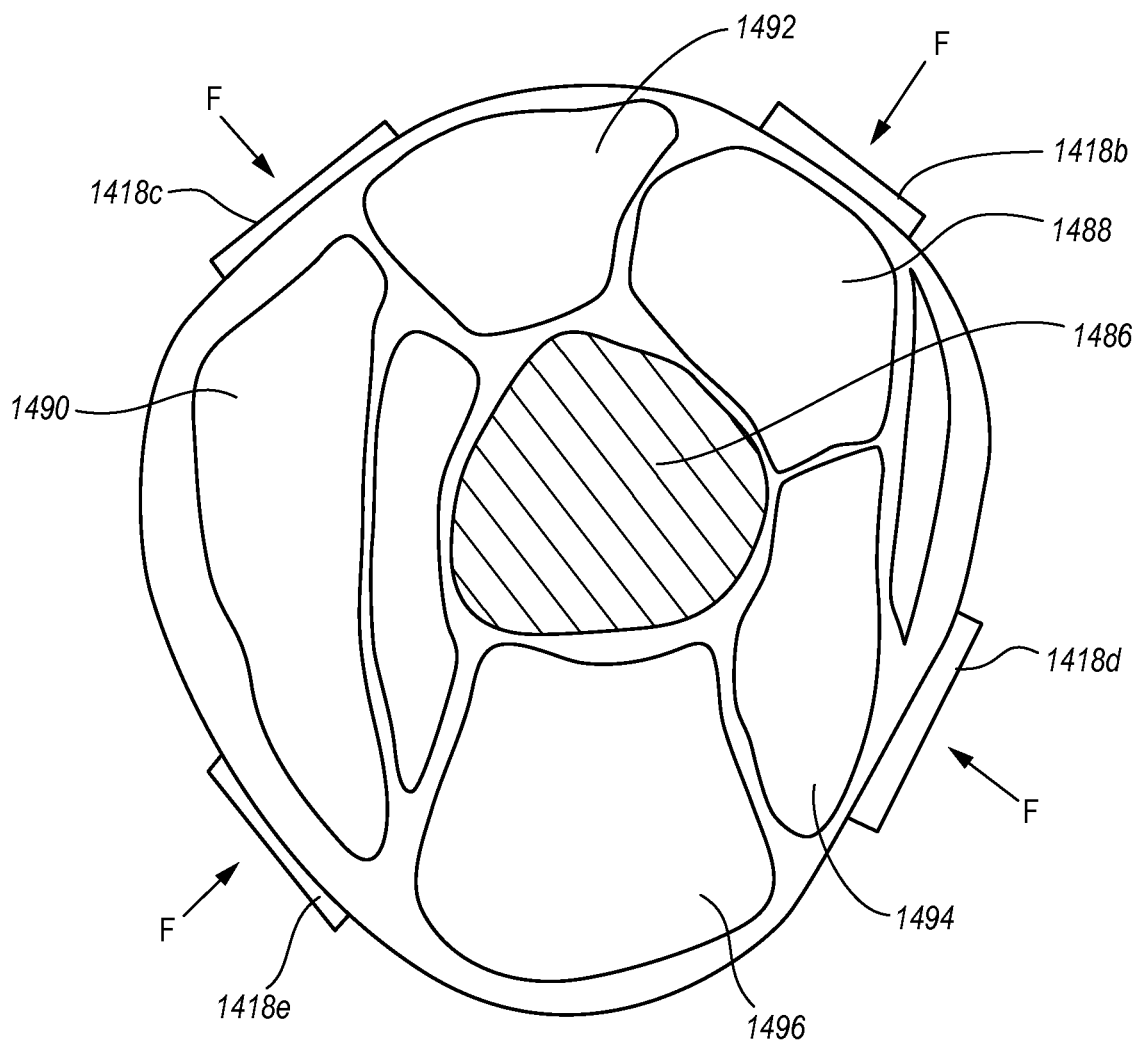
FIG. 43 is a schematic cross-sectional view of the human leg taken along the view line 43-43 in FIG. 36 and illustrating directions in which forces are applied by the adjustable prosthetic system of FIG. 40

Referring to FIGS. 35 and 36 (FIG. 35 showing a left leg having features that are a mirror image of those features shown in the right leg of FIG. 36), the tensioning pads 1318a-1318h are described for the prosthetic adjustment system 1300 shown in FIGS. 30-34. Tensioning pad 1318a may be referred to as an interior patellar panel or tensioning pad. The tensioning pad 1318a is arranged to apply pressure to a patellar tendon 1362. The tensioning pad 1318a may also be arranged to apply pressure to an infrapatellar panel or pad 1360 (see FIG. 38). The tensioning pad 1318b may be referred to as an anterior lateral panel or tensioning pad. The tensioning pad 1318b may be arranged to apply pressure on a tibialis muscle 1382. The tensioning pad 1318b may also be arranged to apply pressure on a extensor muscle 1380. In at least some arrangements, the tensioning pad 1318b may be arranged to ultimately apply pressure on an interosseous membrane 1372 that extends between a fibula bone 1368 and a tibia bone 1370.

The tensioning pad 1318c may be referred to as an anterior medial panel or tensioning pad. The tensioning pad 1318c may be arranged to apply pressure on a medial aspect 1378 of the tibia bone 1370. The tensioning pads 1318d and 1318f may be referred to as lateral posterior panels or tensioning pads. The tensioning pads 1318d, 1318f may be arranged and configured to apply pressure on a gastrocnemius muscle 1364. The tensioning pads 1318d, 1318f may also be arranged and configured to apply pressure on a soleus muscle 1366 as well as a fibularis longus muscle 1374 and a fibularis brevis muscle 1376.

Tensioning pads 1318e, 1318g may be referred to as posterior medial panels or tensioning pads. The tensioning pads 1318e, 1318g may be arranged to apply pressure on the gastrocnemius and soleus muscles 1364, 1366. A tensioning panel 1318h may be referred to as a posterior panel or tensioning pad that is arranged to apply pressure on the gastrocnemius and soleus muscles 1364, 1366.

In at least some arrangements, all of the tensioning pads 1318a-1318h are interconnected with a single tensioning line that has tension adjusted in the tensioning line by a single tightening mechanism. In other arrangements, such as the one shown in FIGS. 13 17, the tensioning pads 1318a-1318h are divided into separate groups of tensioning pads that are interconnected with separate tensioning lines 1314, 1315. The tensioning lines 1314, 1315 are adjusted in tension using separate tightening mechanisms 1316, 1317, respectively. In still further arrangements, more than two tensioning lines and more than two tightening mechanisms may be used to apply force to the tensioning pads 1318a-1318h to create radially inward directed forces upon the user's limb.

Separating the various tensioning pads 1318a-1318h into different zones (i.e., upper, lower, medial and lateral zones) and providing separate tightening mechanisms for each zone may enhance the user's ability to adjust the amount of tightening or "locking in" at different regions in the interface between the prosthetic adjustment system 1300 and the user's limb. The prosthetic adjustment system 1300 may provide both enhanced adjustability as to the amount of incremental adjustment, as well as increased flexibility in the location in which a tightening or radially inward directed forces are applied relative to the user's limb.

The tensioning pads 1318a-1318h may be constructed as separate pieces that comprise a unique material composition, thickness, shape and size distinct from any features of the prosthetic 1312. In other arrangements, at least some of the tensioning pads 1318a-1318h are formed from portions of the prosthetic 1312 such as, for example, from portions of the outer shell 1348. For example, in some embodiments (such as described above), the tensioning pads 1318a-1318h are cut or otherwise formed at least in part from the outer shell 1348.

In some arrangements, at least some of the tensioning pads 1318a-1318h are completely disconnected from the outer shell 1348. In other arrangements, at least portions of at least some of the tensioning pads 1318a-1318h are interconnected and integral with the outer shell 1348. Typically, at least a portion of each of the tensioning pads 1318a-1318h is moveable radially inward and outward relative to the remaining portions of the outer shell 1348. Usually, the outer shell 1348 maintains a generally rigid, fixed shape and size while the tensioning pads 1318a-1318h are moveable radially inward and outward to adjust a radially inward directed force relative to the user's limb. This adjustment and application of radially inward directed force by the tensioning pads 1318a-1318h can resolve or otherwise make up a space or gap that may exist between the user's limb and an interior surface of the prosthetic device 1312 caused by, for example, shrinkage of the limb due to water distribution over the course of a day, loss of weight, and/or other reasons.

In some arrangements, at least some of the tensioning pads 1318a-1318h are mounted directly to an outer surface of the inner liner 1346. In other arrangements, portions of the inner liner 1346 are removed in the area around the tensioning pads 1318a-1318h such as, for example, in the area radially spaced inward from the tensioning pads 1318a-1318h. In still further arrangements, the inner liner 1346 is completely removed from the prosthetic device 1312 such that the user's limb directly contacts the inner surface of the outer shell 1348.

The outer shell 1348 also can provide a relatively rigid base or foundational structure that resists deformation upon application of the tension force in the tensioning lines 1314, 1315 and provides a stable base or foundation for the tightening mechanisms. The tensioning lines may be mounted to an exterior surface of the outer shell 1348 such as, for example, using the attachment arrangement shown with reference to FIGS. 18-23. In other arrangements, the tensioning lines 1314, 1315 may be at least partially embedded within the outer shell 1348 such as described above with reference to the embodiment of FIGS. 24 and 25. A tensioning line can pass through or otherwise be coupled to one or more of the tensioning pads 1318a-1318h at least once, or in some arrangements, at least twice. In some embodiments, the outer shell 1348 comprises a carbon fiber or composite material in the guide path (i.e., the pathway for the tensioning lines 1314, 1315) within the outer shell 1348 as defined by a tubular structure. The tubular structure may remain in place within the outer shell 1348. Alternatively, the tubular structure may be removable. The tubular structure may comprise a material that is resistant to degradation when forming the carbon or composition outer shell 1348 such as, for example, Teflon or nylon.

The tightening mechanism 1316, 1317 may comprise a ratchet device, spool, and other features that provide incremental adjustment of tension in the associated tensioning line 1314, 1315. Many types of tightening mechanisms are possible, each of which provides a different function or possible advantage. Some example tightening mechanisms are shown and described above.

While the examples illustrated in FIGS. 30-38 are made primarily to transtibial prosthetic prosthesis, the same principals related to adjustment systems and methods may be equally applicable to other types of prosthesis, such as above the knee (transfemoral), above the elbow (transhumeral), and below the elbow (transradial).

Referring now to FIGS. 36 and 39-43, another example of prosthetic adjustment system 1400 is shown and described. The prosthetic adjustment system 1400 is configured for use with a transfemoral (i.e., above the knee) residuum, and includes a prosthetic device 1412, at least one tensioning line 1414, at least one tightening mechanism 1416, and a plurality of tensioning pads 1418b-1418e.

The prosthetic device 1412 includes a socket 1420 defining a cavity 1428 and having an upper opening 1430, anterior and posterior portions 1434, 1436, and lateral and medial portions 1438, 1440. The prosthetic device 1412 may further include an inner liner 1446 and an outer shell 1448.

The tensioning pads 1418b-1418e may be arranged around a periphery of the prosthetic device 1412 and at any desired vertical position. The size, shape, orientation, and number of tensioning pads 1418b-1418e may provide any desired amount of pressure and radially inward directed forces on the user's limb so as to adjust for improper interfaces (e.g., gaps or spaces) between the prosthetic device 1412 and the user's limb, such as may result from varying water retention, etc. In at least some arrangements, the tensioning pads 1418b-1418e have a greater thickness than a thickness of the outer shell 1448. Consequently, applying a tension force in the tensioning lines 1414 passing through the tightening pads 1418b-1418e applies an inwardly directed force on the user's limb.

The tensioning pad 1418b may be referred to as an anterior lateral panel or tensioning pad. The tensioning pad 1418c may be referred to as an anterior medial panel or tensioning pad. The tensioning pad 1418d may be referred to as a posterior lateral panel or tensioning pad. The tensioning pad 1418e may be referred to as a posterior medial panel or tensioning pad.

Each of the tensioning pads 1418b-1418e may be arranged to contact a given feature or combination of features of the user's limb. The user's upper leg may include a femur 1486, a vastus lateralis 1488, a vastus medialis 1490, a vastus intemdius 1492, a biceps femorous 1494, and an adductor magnus 1496 (see FIG. 43). The tensioning pads 1418b-1418e may be arranged to contact any one or combination of these anatomical features of the user's upper leg.

Each of the tensioning pads 1418b-1418e may be completely disconnected from surrounding portions of the outer shell 1448, and may be referred to as free floating pads or panels. In other arrangements, at least some of the tensioning pads 1418b-1418e may be connected to the outer shell 448, such as being integrally formed and continuous with the outer shell 448.

A single tensioning line 1414 and tiny mechanism 1416 are shown and described with reference to the embodiment of FIGS. 39-42 to move the tensioning pads 1418b-1418e. The tightening mechanism 1416 is shown positioned near the upper opening 1430 along the lateral portion 1440 of the prosthetic device 1412. This position and location for the tightening mechanism 1416 may promote easier access by the user and may, in some circumstances, be positioned to provide less obstruction or damage by inadvertent contact. The tightening mechanism 1416 may be positioned at any location on the prosthetic device 1412.

In other arrangements, multiple tightening mechanisms and multiple tensioning lines may be used to apply the desired forces to tensioning pads 1418b-1418e. The tensioning pads 1418b-1418e may be separated into different zones, such as, for example, upper or lower zones, anterior, posterior, lateral, or medial zones, wherein one or more of the zones are associated with a single tightening mechanism and single tensioning line. Providing multiple zones and multiple tightening mechanisms may improve the flexibility available to the user for incrementally and specifically adjusting and tightening the inwardly directed forces on the user's limb via the tensioning pads 1418b-1418e.

As with the other embodiments disclosed herein, the tensioning line 1414 may be positioned at least partially on an exterior surface of the outer shell 1448 and/or embedded within the outer shell 1448. Further, the inner liner 1446 may be completely or partially removed at various locations as described with reference to the other embodiments above.

The various prosthetic adjustment system features and functions described herein can reduce the amount of soft tissue interface between the user's limb and the prosthetic device. In some arrangements, the prosthetic adjustment system tends to more completely and solidly engage with the bony portions of the user's limb, such as along the length of the bone shaft, whether solid or semi-solid portion of the user's limb.

Figure 44:
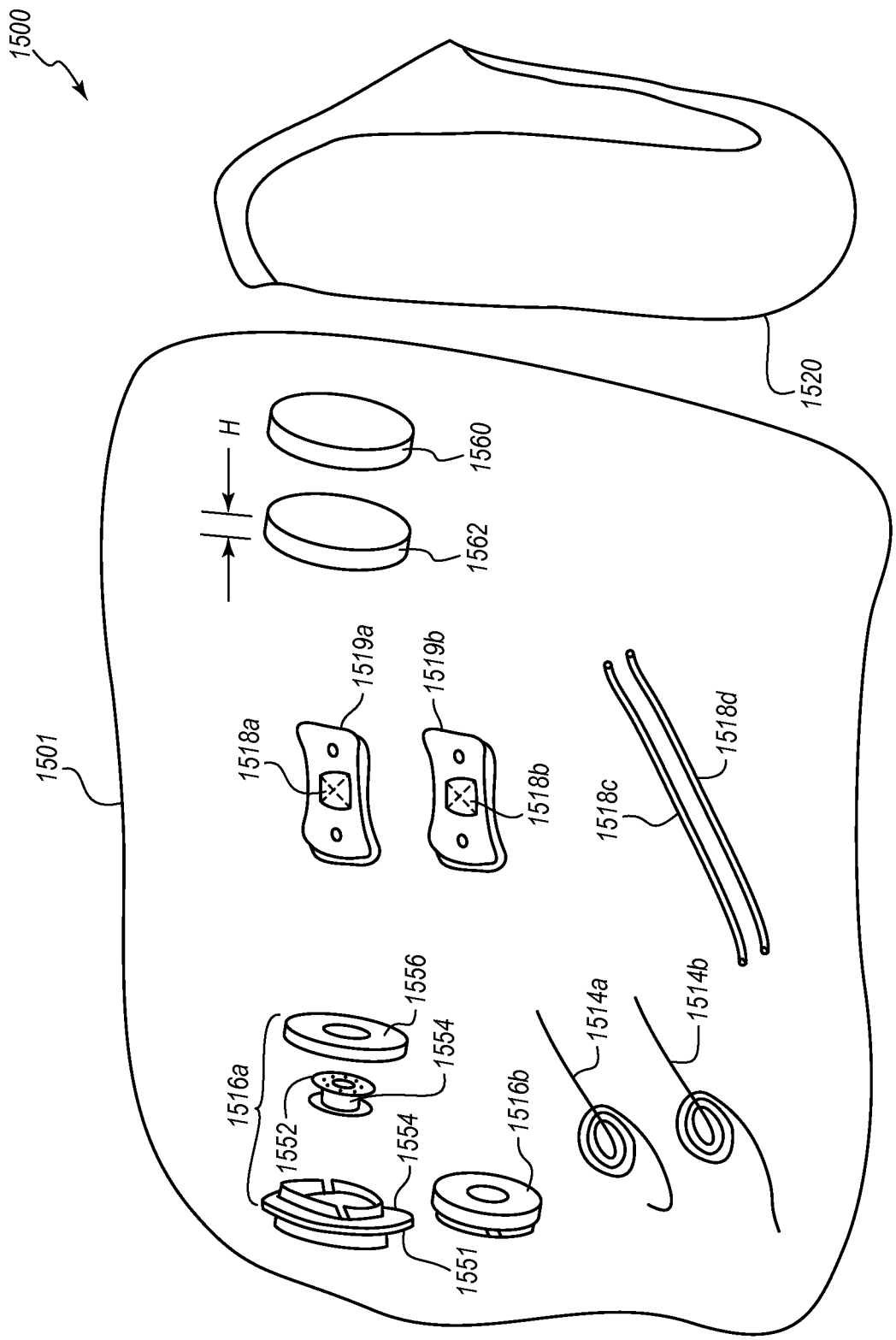
FIG. 44 is a perspective view of an embodiment of a kit that is configured to be used in the creation of an adjustable socket.

Referring now to FIG. 44, an example kit 1500 is shown comprising certain components for creating a prosthetic adjustment system. The kit 1500 includes a package 1501 within which is included a plurality of tensioning lines 1514b, 1514b, a plurality of tightening mechanisms 1516a, 1516b, a plurality of guide members 1518a, 1518b (e.g., constructed as bracket members) and 1518c, 1518d (e.g., constructed as conduit or tube members), and a plurality of tensioning members 1519a, 1519b. The tightening mechanisms 1516a, 1516b include a base 1550, a ratchet member 1552, a spool 1554, and a turning knob 1556. The tensioning lines 1514a, 1514b are collected on the spool 1554 upon rotation of the ratchet member 1552.

The kit 1500 may be used either for retrofitting an existing socket 1520 or for creating a new socket. For example, the bracket-like guide members 1518a, 1518b may be used with an existing socket 1520 and may be mounted to an exterior of the socket 1520. In some instances, one or more moveable panels may be cut in the socket 1520, and one or more guide members 1518a can be mounted to each of the panels. One or more additional guide members 1518b can be mounted to a remaining receptacle portion of the socket 1520, and a tensioning line 1514a can be strung through the guide members 1518a, 1518b and connected with the tightening mechanism 1516a. In use, the modified socket 1520 can allow for adjustment of the newly created panel relative to the receptacle portion of the socket. In some instances it can be desirable to add padding to an interior of the newly created panels. Accordingly, in some instances, the kit 1500 can include padding that can be applied at an interior of the newly formed panels. In some embodiments, the kit 1500 can include mounting hardware, adhesives, and or attachment devices of any suitable variety by which the guide members 1518a, 1518b and/or by which the padding may be attached to the panels.

The guide members 1518c, 1518d of the tube variety may be used, for example, in the creation of a new socket, such as in methods discussed above. Further embodiments of the kit 1500 may be directed primarily to one use or another, whether for retrofitting or for original manufacture of a socket. Accordingly, various kits may have more or fewer items than those depicted in the illustrated embodiment. Moreover, in some embodiments, the kit 1500 can include instructions, such as those discussed above. The instructions can provide information regarding any suitable method for constructing an adjustable prosthetic system.

In various embodiments, the kit 1500 may include a dummy 1560, 1562 for use in formation of a socket. In some instances, a dummy may be used in a vacuum forming technique. In other instances, a dummy may be used in a lamination technique. In one example, a lamination dummy is constructed as a lid to seal off the inner portions of the tightening mechanism 1516a, 1516b to protect them during the lamination process. A flange or skirt portion 1551 of the base 1550 of the tightening mechanism 1516a, 1516b may laminated between layers in the socket 1520. In one example, the flange portion 1551 is extends radially outward about 0.25 inches to about 0.375 inches from the base 1550. The flange portion 1551 can be laminated directly between layers of a wall structure of the socket.

In other embodiments, the flange portion 1551 of the base 1550 may function as a stop lip on vacuum formed socket. The flange portion 1551 can permit increased tension applied on an outer surface of the socket without pulling the tightening mechanism 616a, 616b out of the socket.

The ratchet member 1552, spool 1554 and knob 1556 may be removed before laminating and replaced with a positive dummy 1560 to seal closed the tightening mechanism 1516a, 1516b so as not to fill with resin during lamination. Thereafter, the top of the dummy 1560 is ground down and removed, and the ratchet member 1552, spool 1554 and knob 1556 are assembled on the base 1550, and further forming steps can be performed.

In another example, a vacuum forming dummy 1562 may be used in place of the tightening mechanism 1516a, 1516b to help form an aperture in the socket. The dummy 1562 may comprise, for example, Delron or similar polymeric material. The dummy 1562 may comprise the same profile (e.g., circumference and/or diameter) as the tightening mechanism 1516a, 1516b. In one arrangement, the dummy 1562 has a height H of about 0.25 inches to about 1 inches, and in some embodiments, can be about 0.375 inches. The dummy may be placed on the patient mold (i.e., the mold representing the patient's residuum) before vacuum forming. After vacuum forming, the portion of the socket covering the dummy can be ground down, and the dummy can then be removed. When the dummy is removed from the socket, an aperture remains that is sized for insertion of the tightening mechanism 1516a, 1516b.

The example adjustment systems disclosed herein may be particularly useful for applying a compressive force to a socket portion of a prosthetic at a single location, such as, for example, an anterior patellar tendon bar or a posterior gastrocnemius location. There may be advantages of some of the example adjustment systems and methods disclosed herein related to application of a compressive force to the socket at two or more locations. There may be advantages related to application of a compressive force at three or more locations by the example adjustment systems and methods disclosed herein. The ability to customize the example adjustment systems disclosed herein for application of compressive forces at certain locations on a socket can be desirable in many instances.

The particular location of the compressive force applied by, for example, increasing tension in a tensioning line using a tightening mechanism having incremental adjustment capabilities can be an advantageous property of certain embodiments disclosed herein. Another advantage may relate to adjusting an internal dimension of a socket cavity of a prosthetic device using floating panels or other structure that is movable relative to a rigid portion of the cavity.

Certain principles that are described above with reference to lower limb prosthetic adjustment systems could also be applied to upper limb prosthetic adjustment systems such as those systems needed for above and below the elbow. Further, while wire tensioning systems have been discussed, other tensioning systems may be applicable. For example, air or other fluid bladders may be used, alone or in combination with the wire tensioning systems disclosed herein, along an inner surface of a prosthetic device to apply the desired amount of pressure and/or fill space between the patient's limb and the prosthetic device.

As is apparent from the foregoing disclosure, in some embodiments, a prosthetic adjustment system includes a socket member, at least one tensioning member, at least one tensioning line, and at least one tightening mechanism. The socket member defines a cavity sized to receive a portion of a human limb, wherein the socket portion has an anterior portion and a posterior portion. The at least one tensioning member is arranged to move radially inward relative to the socket member. The at least one tensioning line is connected to the tensioning member. The at least one tightening mechanism is positioned on the socket portion and configured to adjust tension in the tensioning line to move the tensioning member relative to the socket.

In various embodiments, the socket has a single piece structure that is form-fit to the shape and size of the residuum. In other embodiments, the socket can include multiple pieces, such as a double piece structure with a flexible inner interface and rigid exterior socket. In at least some examples, the socket is generally continuous around its circumference and from the top to bottom of the socket. In other examples, the socket is discontinuous around its periphery at some locations along a length of the socket. The socket may include a plurality of openings, cut out portions, and flexible or cantilevered portions that assist in tightening the socket about the limb.

In some embodiments, a prosthetic adjustment kit can be configured for use with an existing prosthetic socket and/or in the formation of a new socket. Some kits may include a package, at least one mechanical tightening mechanism positioned in the package, at least one tensioning line positioned in the package, and at least one tensioning member. The tensioning line can ultimately be connected to the tensioning member. Applying tension in the tensioning line with the tightening mechanism moves the tensioning member relative to the prosthetic socket. The kit may also include at least one lace or tensioning line guide in the package. The lace guide may be used to secure the tensioning line to the socket and/or tensioning member. The kit may further include at least one laminating dummy the package for use in forming the socket.

In some embodiments, a method of adjusting a fit between a socket portion of a prosthetic device and a patient's limb can include providing a prosthetic adjustment system having at least one tensioning line, wherein at least one tensioning member, and at least one tightening mechanism, at least partially wrapping the at least one tensioning line around the prosthetic device, and adjusting the at least one tightening mechanism to change tension in the at least one tensioning line. Increasing tension in the at least one tensioning line changes moves the tensioning member relative to the socket portion of the prosthetic device to tighten the socket portion about the person's limb.

In certain embodiments, a prosthetic device can includes a rigid socket member defining a cavity sized to receive a portion of a person's limb, and at least one panel member positioned at a location around a periphery of the socket member. The at least one panel member is movable into the cavity. The device further includes an adjustment mechanism configured to move the at least one panel member relative to the cavity to apply a force to the person's limb positioned in the cavity.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on. Similarly, for the second claim set that begins with independent 15, claim 17 can depend from either of claims 15 and 16, with these separate dependencies yielding two distinct embodiments; claim 18 can depend from any one of claim 15, 16, or 17, with these separate dependencies yielding three distinct embodiments; claim 19 can depend from any one of claim 15, 16, 17, or 18 with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112 ¶6. Embodiments of the invention in which an exclusive property or privilege is claimed are defined as follows.

The invention claimed is:

1. A system for interfacing a residual limb with a prosthetic device, the system comprising:
   a socket member that is configured to be connected to a prosthetic device, the socket member comprising a receptacle portion that defines a cavity sized to receive at least a portion of a residual limb therein;
   a tensioning line extending through a tubular guide, the tubular guide disposed within a wall of the socket member; and
   a tightening mechanism that comprises an actuator and a base, the base comprising an opening through which the tensioning line can enter the tightening mechanism, wherein an end of the tubular guide terminates at the opening of the base, the end of the tubular guide being disposed within the wall of the socket member, and wherein the tightening mechanism is coupled with the tensioning line such that actuation of the actuator effects movement of the tensioning line, and wherein movement of the tensioning line in a first direction due to actuation of the actuator is configured to tighten a fit between the socket member and the residual limb.

2. The system of claim 1, wherein the actuator comprises at least one of a knob, a lever, or a button.

3. The system of claim 2, wherein the actuator comprises a button.

4. The system of claim 3, wherein the actuator is actuated by pushing the button.

5. The system of claim 1, wherein actuation of the actuator is manual.

6. The system of claim 1, wherein the tightening mechanism is positioned on the socket.

7. The system of claim 1, wherein the tightening mechanism is configured to be coupled to the prosthetic device.

8. The system of claim 1, wherein the tensioning line comprises a lace.

9. A prosthetic adjustment system, comprising:
a receptacle that is configured to be connected to a prosthetic device, the receptacle defining a cavity sized to receive at least a portion of a residual limb therein;
a tensioning line extending through a guide path that is disposed within a wall of the receptacle; and
a tightening mechanism that is configured to adjust tension in the tensioning line so as to fit the receptacle on the residual limb, wherein the tightening mechanism comprises an opening through which the tensioning line can enter the tightening mechanism, wherein an end of the guide path terminates at the opening of the tightening mechanism, the end of the guide path being disposed within the wall of the receptacle such that the tensioning line is interior to a plane defined by an outer surface of the receptacle as the tensioning line passes from the guide path to the tightening mechanism.

10. The prosthetic adjustment system of claim 9, wherein the tightening mechanism comprises an actuator, and wherein actuation of the actuator effects movement of the tensioning line.

11. The prosthetic adjustment system of claim 10, wherein the actuator comprises at least one of a knob, a lever, or a button.

12. The prosthetic adjustment system of claim 11, wherein the actuator comprises a button.

13. The prosthetic adjustment system of claim 12, wherein the actuator is actuated by pushing the button.

14. The prosthetic adjustment system of claim 10, wherein actuation of the actuator is manual.

15. The prosthetic adjustment system of claim 9, wherein the tightening mechanism is positioned on the receptacle.

16. The prosthetic adjustment system of claim 9, wherein the tightening mechanism is configured to be coupled to the prosthetic device.

* * * * *